US011872161B2

(12) United States Patent
Buck et al.

(10) Patent No.: US 11,872,161 B2
(45) Date of Patent: Jan. 16, 2024

(54) OPHTHALMIC SURGERY LASER SYSTEM AND METHOD FOR UTILIZING SAME FOR OPHTHALMIC SURGERY

(71) Applicant: Drake Precision Optics, Inc., Escondido, CA (US)

(72) Inventors: Jesse Buck, Escondido, CA (US); Michael Hager, Escondido, CA (US)

(73) Assignee: DRAKE PRECISION OPTICS, INC., Escondido, CA (US)

( * ) Notice: Subject to any disclaimer, the term of this patent is extended or adjusted under 35 U.S.C. 154(b) by 177 days.

(21) Appl. No.: 16/712,754

(22) Filed: Dec. 12, 2019

(65) Prior Publication Data

US 2020/0188166 A1    Jun. 18, 2020

Related U.S. Application Data

(60) Provisional application No. 62/826,381, filed on Mar. 29, 2019, provisional application No. 62/814,682, filed on Mar. 6, 2019, provisional application No. 62/778,839, filed on Dec. 12, 2018.

(51) Int. Cl.
*A61F 9/008* (2006.01)
*A61B 18/20* (2006.01)

(52) U.S. Cl.
CPC .... *A61F 9/008* (2013.01); *A61B 2018/20353* (2017.05); *A61B 2018/20359* (2017.05); *A61F 2009/00872* (2013.01); *A61F 2009/00897* (2013.01)

(58) Field of Classification Search
CPC ................................ A61F 9/008; A61B 18/20
See application file for complete search history.

(56) References Cited

U.S. PATENT DOCUMENTS

| | | | | |
|---|---|---|---|---|
| 6,162,211 | A * | 12/2000 | Tankovich | A61B 18/203 606/9 |
| 6,312,423 | B1 * | 11/2001 | Ota | A61F 9/008 351/206 |
| 8,679,100 | B2 | 3/2014 | Raksi et al. | |
| 2001/0056276 | A1 * | 12/2001 | LaHaye | A61B 18/20 606/5 |
| 2002/0165525 | A1 * | 11/2002 | Nakamura | A61B 18/22 606/4 |

(Continued)

OTHER PUBLICATIONS

Patent Cooperation Treaty, International Search Report issued in PCT/US2019/066039, dated Apr. 8, 2020, pp. 11-14.

(Continued)

*Primary Examiner* — Lynsey C Eiseman
(74) *Attorney, Agent, or Firm* — Pillsbury Winthro

(57) ABSTRACT

An ophthalmic surgery laser system and method of laser delivery for an ophthalmic surgery laser system are disclosed herein. Embodiments of the system and method are directed to an ophthalmic surgery laser system including a laser engine, a laser guide, and a laser shaper. Embodiments of the system and method are directed to a laser delivery system for an ophthalmic surgery laser system. Embodiments of the system and method are directed to an ophthalmic surgery laser system including additional functionality such as laser scanning confocal microscopy, 3D laser scanning, and laser beam diagnostics. Embodiments further include the use of a lower power illumination source.

15 Claims, 37 Drawing Sheets

(56) References Cited

U.S. PATENT DOCUMENTS

| | | |
|---|---|---|
| 2004/0024485 A1 | 2/2004 | McCoy |
| 2006/0118263 A1* | 6/2006 | Silvestrini .............. G02C 7/165 |
| | | 164/46 |
| 2007/0106285 A1 | 5/2007 | Raksi |
| 2008/0186551 A1* | 8/2008 | Hanft .................. G02B 26/105 |
| | | 359/205.1 |
| 2009/0122819 A1 | 5/2009 | Dantus et al. |
| 2009/0247996 A1* | 10/2009 | Abe ........................ A61F 9/008 |
| | | 606/4 |
| 2010/0290007 A1* | 11/2010 | Van de Velde ...... A61B 3/1025 |
| | | 351/221 |
| 2011/0028952 A1* | 2/2011 | Raksi .................. A61F 9/00825 |
| | | 606/4 |
| 2011/0218523 A1* | 9/2011 | Robl ....................... A61F 9/008 |
| | | 606/4 |
| 2011/0276042 A1* | 11/2011 | Dick .................. A61F 9/00814 |
| | | 606/5 |
| 2012/0016352 A1* | 1/2012 | Dick ....................... A61F 9/008 |
| | | 606/4 |
| 2012/0123444 A1* | 5/2012 | Verhagen ................ B26B 21/56 |
| | | 30/357 |
| 2013/0131652 A1* | 5/2013 | Dick ....................... A61B 18/20 |
| | | 606/4 |
| 2014/0058367 A1 | 2/2014 | Dantus |
| 2014/0079686 A1* | 3/2014 | Barman .................. A61K 8/69 |
| | | 424/94.67 |
| 2014/0098345 A1 | 4/2014 | Cai et al. |
| 2014/0151529 A1* | 6/2014 | Steiner .................... H01J 43/20 |
| | | 250/207 |
| 2014/0236135 A1* | 8/2014 | Donitzky ............ A61F 9/00836 |
| | | 606/5 |
| 2014/0316389 A1* | 10/2014 | Schuele .............. A61F 9/00802 |
| | | 606/5 |
| 2015/0148786 A1* | 5/2015 | Plunkett .................. F21V 14/04 |
| | | 606/4 |
| 2016/0235588 A1* | 8/2016 | Hart ...................... A61F 9/00838 |
| 2016/0249989 A1* | 9/2016 | Devam ................... H04L 67/60 |
| | | 345/633 |
| 2017/0087011 A1* | 3/2017 | Asakura .................. A61F 9/008 |
| 2018/0078418 A1* | 3/2018 | Berezhnyy .......... A61F 9/00804 |
| 2018/0085257 A1* | 3/2018 | Horvath .............. A61F 9/00834 |
| 2018/0250163 A1* | 9/2018 | Lee ........................ A61F 9/0084 |
| 2018/0353068 A1 | 12/2018 | Gray et al. |
| 2019/0282404 A1 | 9/2019 | Bor |

OTHER PUBLICATIONS

Photonics Marketplace, "Beam Diagnostics: Meeting the Need for High Quality", accessed at https ://www.photonics.com/Article/Beam Diagnostics Meeting the Need for High/a25162, Jan. 25, 2023, pp. 1-7.

Auksorius et al., "In vivo imaging of human cornea with high speed and high-resolution Fourier-domain full-field optical coherence tomography", Mar. 28, 2020, pp. 1-16.

* cited by examiner

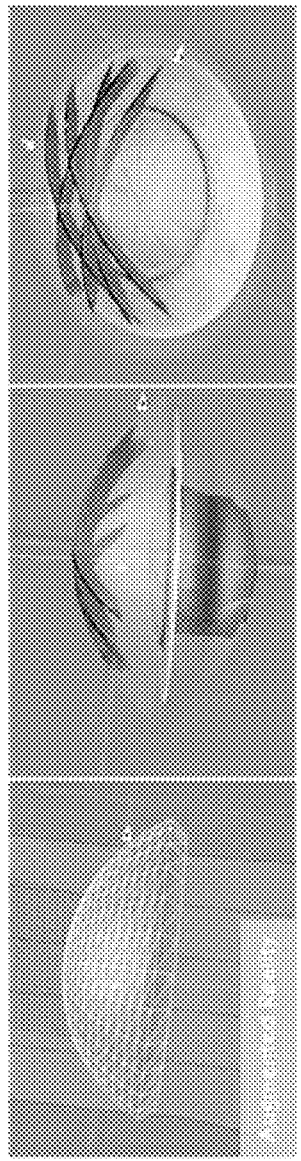
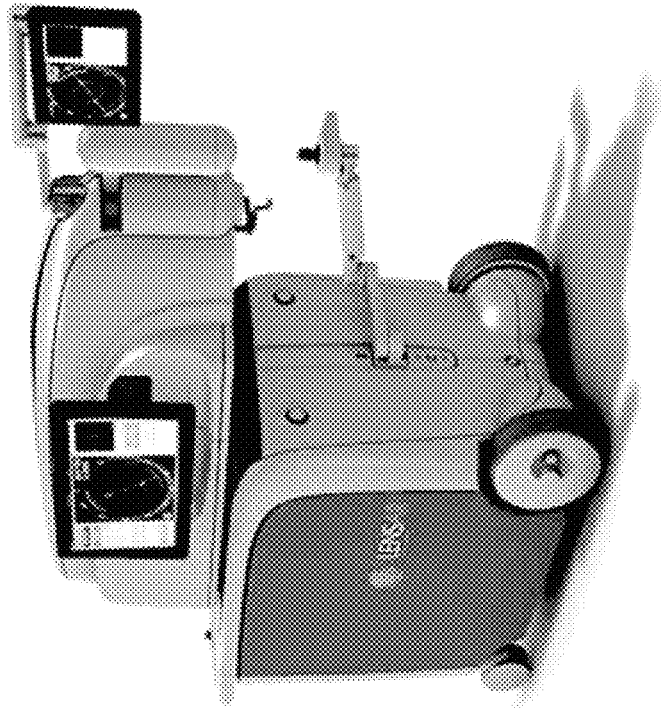
FIG. 4
(Prior Art)

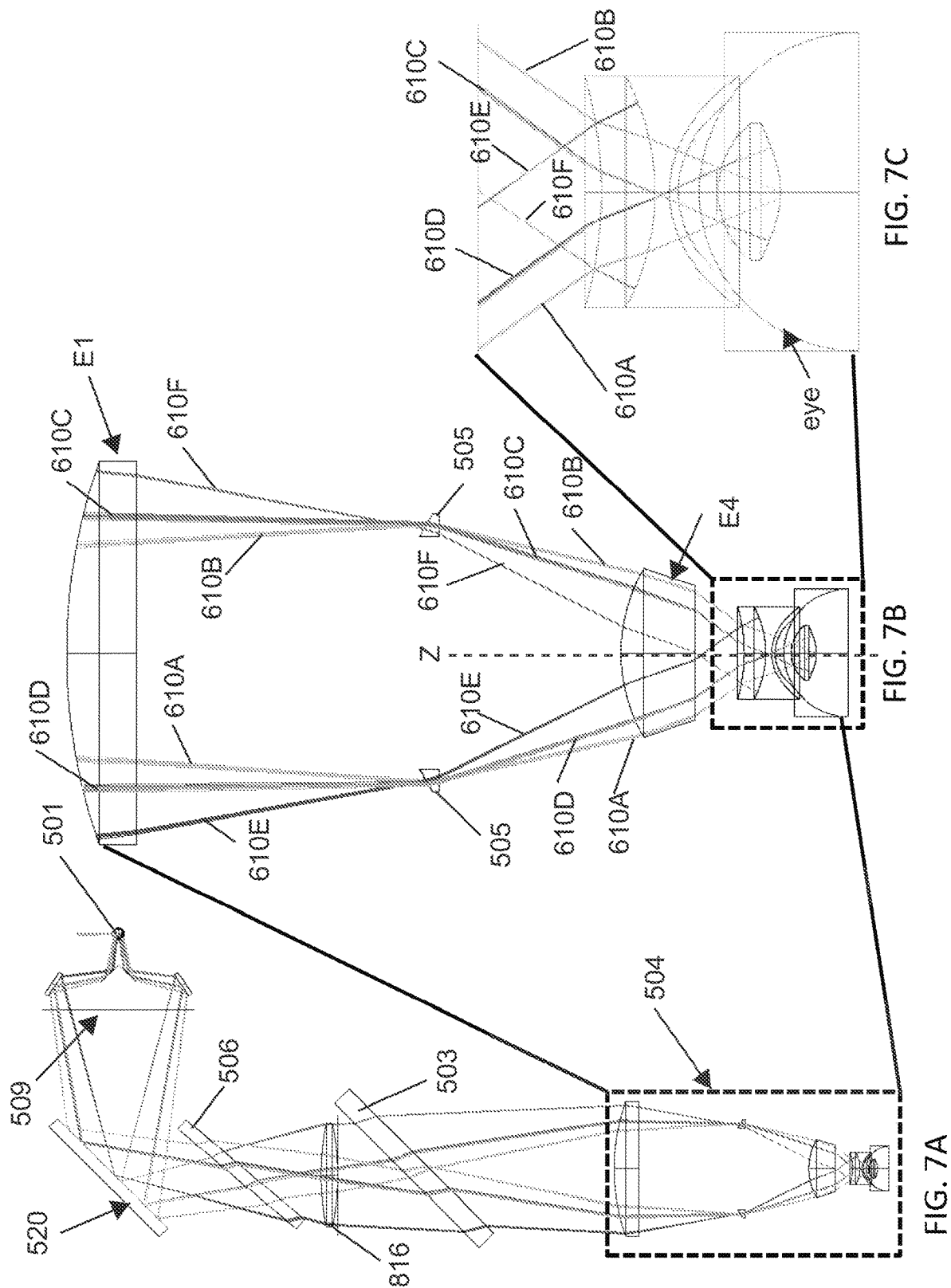

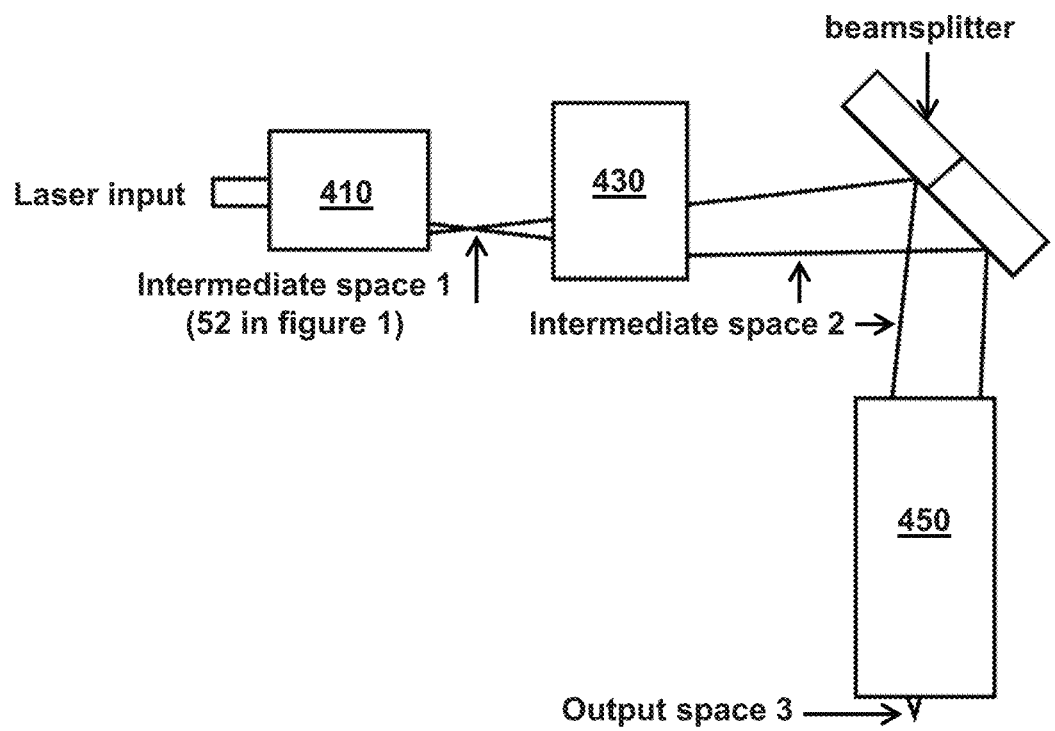
Not-corrected (aberrated)
Infinity corrected (ideal)
FIG. 10A

OPHTHALMIC SURGERY LASER SYSTEM AND METHOD FOR UTILIZING SAME FOR OPHTHALMIC SURGERY

CROSS-REFERENCE TO RELATED APPLICATIONS

This application claims priority to: U.S. provisional patent application 62/778,839, filed Dec. 12, 2018, U.S. provisional patent application 62/814,682, filed Mar. 6, 2019, and U.S. provisional patent application 62/826,381, filed Mar. 29, 2019, the entire contents of each of which are herein incorporated by reference in their entireties.

BACKGROUND

Technical Field

The present disclosure generally pertains to an ophthalmic laser system and a method for delivering a laser for ophthalmic surgery or other high precision 3D laser processing applications.

Description of Related Art

In the field of laser surgery, the eye is a particularly beneficial area of endeavor. In the field of anterior segment ophthalmology, the measurement of cornea and lens topology (CLT) is of primary importance. The cornea and lens are nearly transparent tissues. Thus, optical methods of measurement are advantageous to employ, the major categories being confocal microscopy, optical coherence tomography, and structured light measurements.

Examples of structured light include the ubiquitous slit lamp which projects a ribbon of light at an angle through the eye, and 3D laser scanning in which a narrow laser beam is rapidly scanned on a lateral path to effectively create a sheet of light that may be scanned across the material under test to find the X, Y, and Z coordinates of the surface(s) or other scattering regions of the material under test. A CCD camera is typically focused on the material under test so that the scanned stripe of light can be observed with a digital image. In order to have the Z information present in the image, the only requirement is to create an angle "A" between the axis of the light source and the optical axis of the camera, in which case the axis in the image which is co-planar with the axis of the light source will have a component of the Z axis proportional to the sine of the angle A. This approach is often referred to as laser triangulation. The angle A is often referred to as the disparity angle.

Instruments such as the Oculus Pentacam™ diagnostic and the LENSAR femtosecond laser have been popular 3D scanning instruments used on the market. These devices employ the standard approach to create an angle between the camera and the scanning beam, in which the light beam is coming straight into the eye, while the camera is located off to the side and the camera can be mechanically scanned in azimuth around the axis of the light beam. The camera's azimuthal position is controlled so its optical axis will face the wide axis of the light ribbon or scanning light sheet in order to have the best resolution in the image. The continuous rotation of the light ribbon axis allows every position in the field of view to be illuminated by the corresponding choice of the ribbon angle. With the exception of the origin which is illuminated for all choices of ribbon angle, each point can be illuminated for one and only one choice of ribbon angle, thus there is no multiplicity of perspective angles available for any point in the field of view except for the origin with the Pentacam™.

Another advantage of moving the camera's azimuth position in a full circle is that the disparity angle will be distributed over all clock positions, thus providing the most detailed geometric information. Rotating the camera position creates an advantage of multiple perspective measurements contained in an entire measurement run.

The transparency of the tissue of the cornea and lens allows for image guided scanning of a laser focal spot over a 3-dimensional volume with many surgical opportunities available. In the usual case of non-transparent tissue, the laser scanning is essentially 2-dimensional over the surface of the tissue being treated, such as in dermatology. Surgery of the eye to treat cataracts is the highest volume surgical procedure in the world in terms of number of procedures per year; however, the high cost of an eye surgery laser system has been an obstacle, which prevents all but the top tier of surgeons from owning an advanced ophthalmic laser surgery system (e.g., such as an anterior segment femtosecond eye surgery laser).

Advanced ophthalmic laser surgery systems require accurate in-vivo measurement functions to account for individual eye geometry and other characteristics. Typically, Optical Coherence Tomography (OCT) is used for this purpose and is considered high precision. The inclusion of OCT into a laser surgery system will significantly increase the overall system complexity, and results in the addition of costly components such as spectrometers and wide band light sources.

However, laser scanning confocal microscopy is another technique in use which is generally considered to have higher precision than OCT. Generally, a laser scanning confocal microscope ("LSCM"), is a microscope where illumination is brought to a focus at the view point. By only lighting up the area of interest, improved resolution may be achieved. In some cases, femtosecond laser surgery systems use their cutting laser at a lower power setting to provide illumination. Femtosecond surgery lasers are pulsed (e.g., <1 picosecond), which concentrates the peak power far above the average power.

Such femtosecond laser surgery systems are typically larger and more costly to produce and use. Traditional laser surgery systems and laser delivery systems are bulky, and expensive and difficult to produce and use. A laser delivery system with a deep focus range, such as for ophthalmic surgery, is typically a complex optical design, which is expensive and difficult to produce. Moreover, the complex optical designs for a laser delivery system and associated optical measurement subsystems are costly to manufacture, and comprise a major cost driver of these laser surgery systems, second only to the laser engine which provides the source of femtosecond laser pulses. This high degree of complexity results in large part from applying the standard approach for the optical design of imaging systems to the application of high precision laser surgery, in which case the RMS wavefront error is the merit function to be minimized in the design process, and furthermore the 2 or more modules (groups of lenses in a single housing) in the laser delivery system are typically designed to be infinity corrected.

U.S. Pat. No. 8,262,647, issued to Raksi, et al., shows an optical system for ophthalmic surgical laser, according to the prior art.

SUMMARY

It is an aspect of this disclosure to provide an ophthalmic 3D laser scanning system configured to be integrated into a femtosecond laser surgery system. This system includes: a light source configured to provide a beam of light that is configured to be scanned and a plurality of reflective and refractive devices configured to direct the beam of light from the light source at a variety of angles along a structured path to an objective. The objective is configured to direct the beam of light from the light source at an object in a viewing region of the objective. The system further includes a camera with imaging optics for capturing images of object topography. The camera has a viewing axis along a Z-axis, and the beam of light is positioned at an angle to the Z-axis as it impinges on the object. The object is configured to reflect at least a portion of the beam of light back into the system, and the imaging optics are configured to receive images of the object illuminated by the beam of light such that the received images are subsequently analyzed to calculate geometric dimensions of the object.

Another aspect provides an ophthalmic 3D laser system including: a laser engine capable of generating a laser beam; a laser delivery system in optical communication with the laser engine further including: a laser beam shaper; and a laser guide having a scanning module and a focus module. The scanning module has a receiving end and a transmitting end, and the receiving end receives the generated laser beam and brings the generated laser beam into focus thereby creating a focused beam that is transmitted from the transmitting end into the focus module. The focus module is configured to receive the focused beam from the scanning module and revert the focused beam into a parallel light stream and further direct the parallel light stream into an objective module. The objective module is configured to direct the parallel light stream into a focal point within a three dimensional target space.

Yet another aspect provides an ophthalmic 3D laser system including: a femtosecond laser engine capable of generating a laser beam for surgical procedure; a laser source, with substantially the same wavelength as the femtosecond laser engine, for delivering a low peak power laser beam; a laser beam shaper; a laser beam guide configured to focus a received laser beam for output; and a reconfigurable optical device. The reconfigurable optical device is configured for positioning in a first position and in a second position in order to selectively engage either the generated femtosecond laser beam of the femtosecond laser engine or the low peak power laser beam of the laser source. The first position of the reconfigurable optical device is configured such that the reconfigurable optical device optically engages with the generated femtosecond laser beam such that it may be in line with a path of the generated femtosecond laser beam generated by the femtosecond laser engine which is configured to direct the generated laser beam into the laser beam guide. The reconfigurable optical device is also configured to deny entry of the low peak power laser beam of the laser source into the laser beam guide in the first position. The second position of the reconfigurable optical device is configured such that the reconfigurable optical device is out of alignment with the generated femtosecond laser beam and thus the generated femtosecond laser beam is denied entry into the laser beam guide and wherein the low peak power laser beam is directed into the laser beam guide.

Other aspects, features, and advantages of the present disclosure will become apparent from the following detailed description, the accompanying drawings, and the appended claims.

BRIEF DESCRIPTION OF THE DRAWINGS

FIG. 4 illustrates a commercially available LENSAR system.

FIGS. 7A to 7C further illustrate details of various 3D scanner light paths in accordance with an embodiment.

FIG. 10A illustrates an aspect of focusing the laser at the system output and at an intermediate space, in accordance with an embodiment.

DETAILED DESCRIPTION OF THE PREFERRED EMBODIMENT(S)

Figure 1:
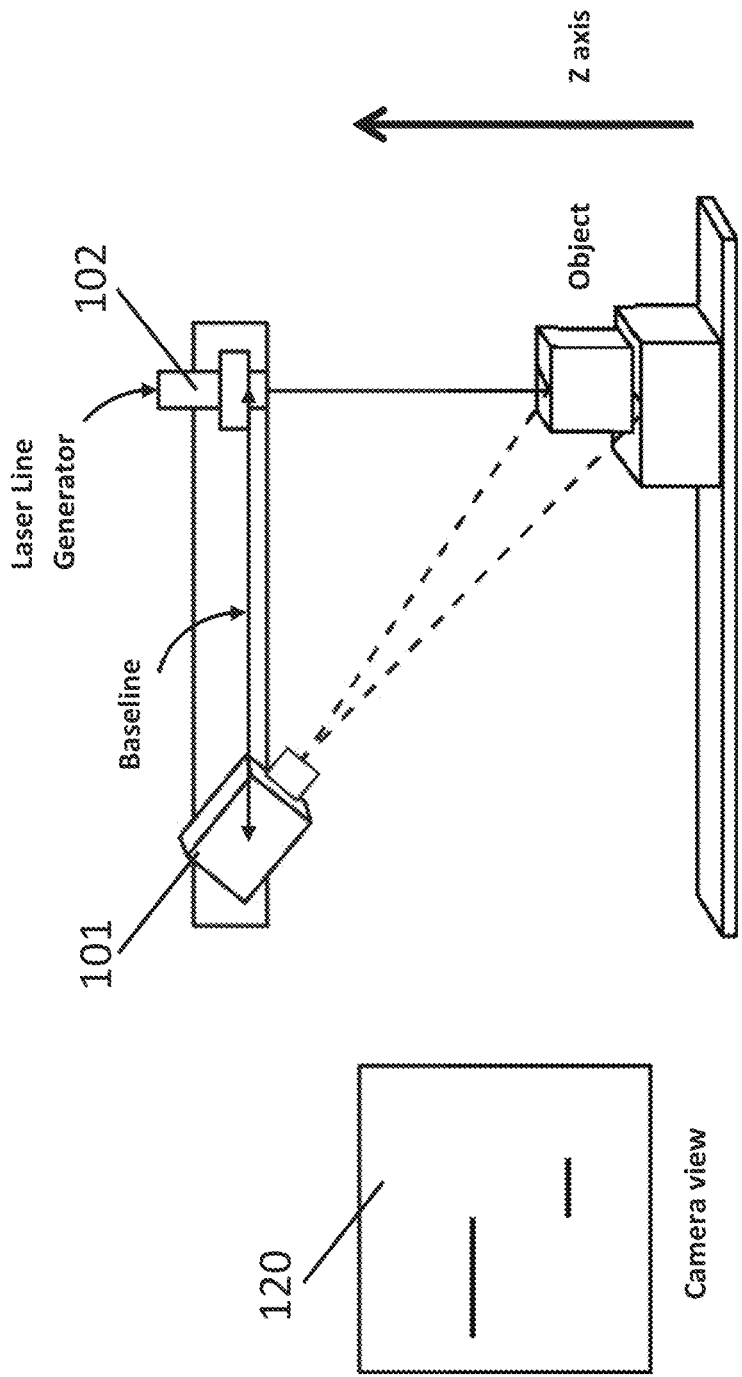
FIG. 1 illustrates a traditional scanning system according to known art.

Various aspects of the novel systems, apparatuses, and methods are described more fully hereinafter with reference to the accompanying drawings. The detailed description set forth below in connection with the appended drawings is intended as a description of various configurations and is not intended to represent the only configurations in which the concepts described herein may be practiced. The detailed description includes specific details for the purpose of providing a thorough understanding of various concepts design process is described herein. However, it will be apparent to those skilled in the art that these concepts may be practiced without these specific details. In some instances, well-known structures and components are shown in block diagram form in order to avoid obscuring such concepts.

As evident by the background discussion previously, an alternative approach that reduces the cost and size of the femtosecond laser surgery systems while retaining the clinical performance capabilities may be beneficial. Further, an optical system which is economical to manufacture, and retains clinical performance capability, that may be integrated into femtosecond laser surgery systems is desirable. Accordingly, the embodiments and features disclosed herein are designed to provide improvements and advancements to ophthalmic systems and features thereof.

Generally, it should be noted that any reference to or mention of a laser, a laser beam, or a beam throughout this disclosure refers to a beam of light (or light beam) that may be from a light source or a laser source.

In accordance with one embodiment, this disclosure takes advantage of the video monitor system (see, e.g., video image lenses 816 and CCD camera 815 in FIG. 8A) which is already required on a surgical laser system to allow the doctor to observe the docking and treatment processes. The video monitor, for example the CCD camera 815 in FIG. 8A, in conjunction with the video imaging lenses 816 which create an image at the CCD plane using the light received through the objective, may also be employed in this case to receive machine vision type 3D scanning data for analysis by the control system. In such an embodiment, the only additional parts required to add this 3D scanning system to a surgical laser system already equipped with a doctor's monitor consist of a compact and relatively inexpensive light projection system (e.g., as described with reference to FIGS. 5A, 7A-7C, and 8A), and small prisms (505) which are added to the outside of the objective assembly (further described with reference to FIGS. 6A-6B).

An ophthalmic surgery laser system and method of laser delivery for an ophthalmic surgery laser system is disclosed herein. Embodiments of the system and method are directed to an ophthalmic surgery laser system including a laser engine, a laser guide, and a laser shaper, which as a group provide the controlled laser cutting. Embodiments of the system and method are directed to, a laser delivery system for an ophthalmic surgery laser system, additional functionality such laser scanning confocal microscopy, structured light scanning, built-in laser beam diagnostics, and other functions. Embodiments further include the use of a lower power illumination source (e.g., continuous wave as opposed to pulsed) for in-vivo measurement functions. The present disclosure shows how to use a movable mirror in conjunction with a small number of additional parts to switch from a laser exposure system over to an LSCM diagnostic imaging function. Beneficially, the most expensive components needed for the LSCM function are already essential for building the laser surgery system (i.e., high NA laser focusing optics, such as NA=0.3, and high speed galvanometer mirror scanners). As such, there may be an advantage of adding this high precision diagnostic to an ophthalmic surgery laser system at a relatively low cost. Moreover and by contrast, using OCT could require expensive additional components such as spectrometers and wideband light sources, which substantially add to the system cost.

Many embodiments include a laser delivery system with an alternative design that reduces the number of moving parts and simplifying the embodiments for ophthalmic 3-D scanning systems. Many embodiments include a 3D scanner visible laser delivery system that is configured to provide beams of light entering the eye at an offset angle with respect to the Z-axis of the objective. Additionally, a camera, for capturing images of the patient ophthalmic topography as well as the surgical display, may be positioned with its optical axis coaxial to the central Z-axis of the objective. Many embodiments may be configured with one or more beam splitters for directing the infrared and visible beams along the desired optical paths.

Traditional methods and systems in the field of ophthalmology for 3-D scanning use optics within a dedicated diagnostic instrument or sometimes it is included in in popular commercial laser devices. In the field of ophthalmology, 3D scanning is a technique traditionally used to capture optical images of the translucent or opaque structures within a patient's eye for use in diagnostic and treatment planning procedures. The layout of the traditional system typically involves the camera being placed at an angle to the axis of the imaging light source that is directed into the patient's eye along the optical axis of the eye, which is understood to be the Z axis. This principle can be illustrated in FIG. 1.

FIG. 1 illustrates what may be seen in the art with traditional 3D scanning systems, where a camera 101 viewing axis is positioned at an angle to the light source 102. The angle between the camera axis and the light source is important for measuring the position of the object within the Z-axis. For example, the laser or light source 102 in FIG. 1 is directed at an object with various Z positions. The image 120 seen from the camera 101 illustrates the lateral position of the laser beam in the image will correspond to the Z position of the object where it is illuminated.

Figure 2B:
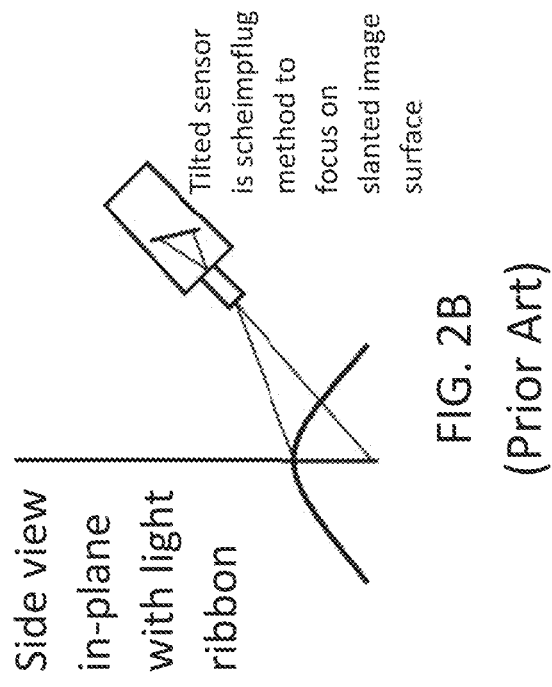
FIGS. 2A and 2B illustrate a front and side view of a traditional ophthalmic scanning system.
Figure 2A:
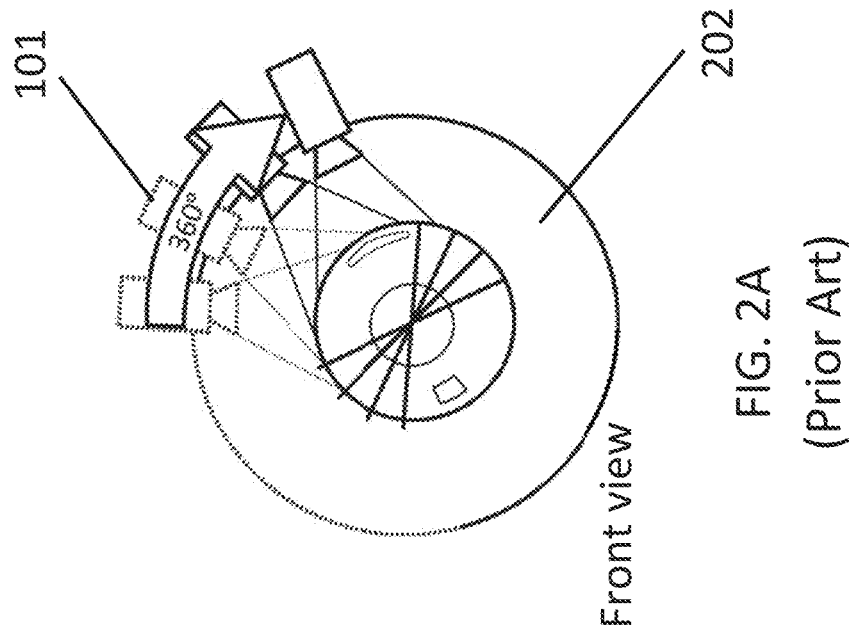
Figure 2C:
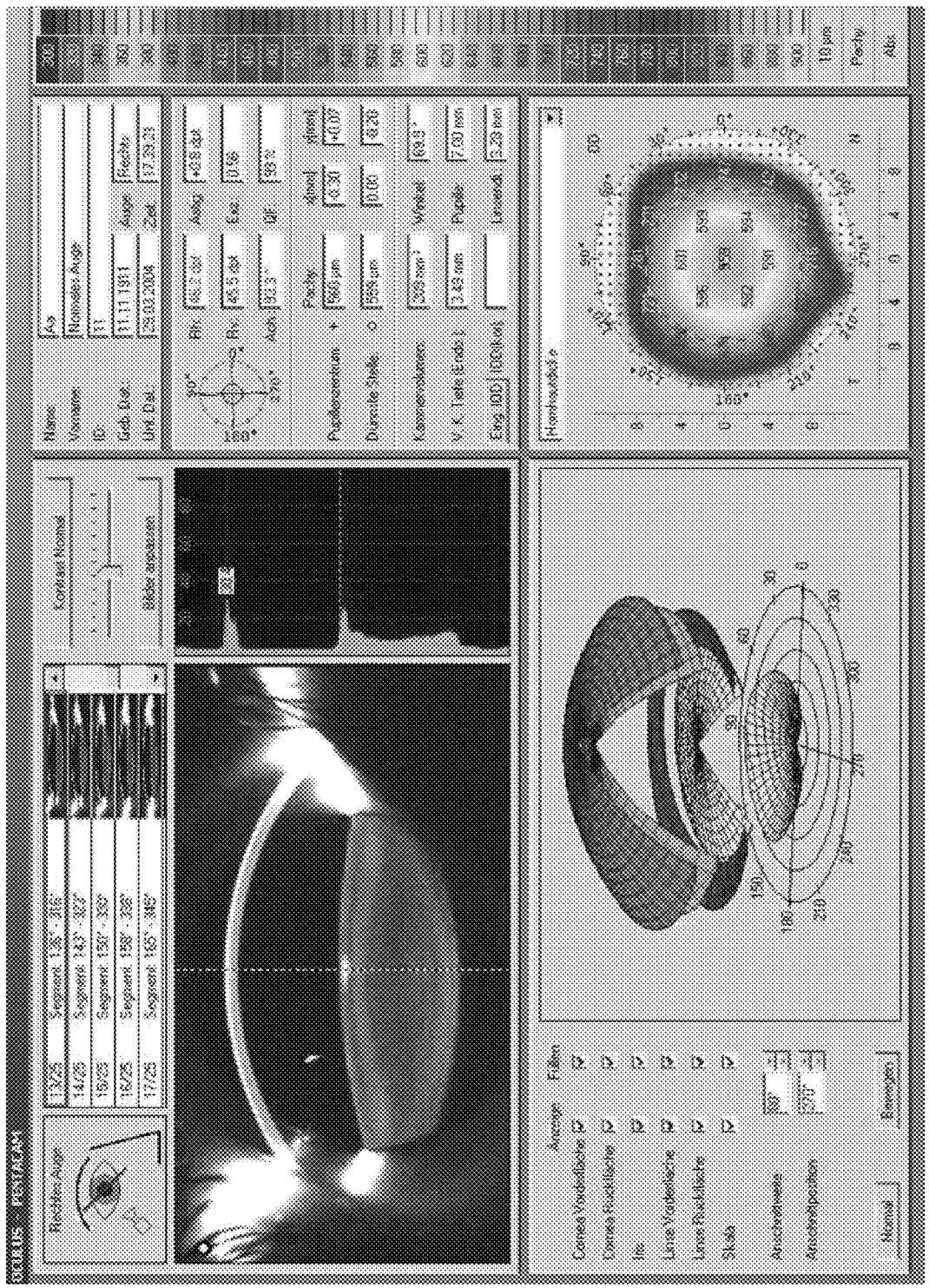
FIG. 2C is a representation of an optical measurement using the commercially available Pentacam™ instrument.

In traditional systems, the camera may be configured to move radially about the object to be measured, such as illustrated in FIG. 2A. FIG. 2A illustrates a front or top view of a traditional system where the light source is directed to the patient's eye 202. The camera 101 may be rotated circumferentially around the eye 202 to record the image produced by the axially directed light ribbon passing through the translucent structures of the eye. Similarly, FIG. 2B illustrated a side view of a traditional system. FIG. 2C shows a typical 3-D analysis of a traditional scanning system.

Figure 3:
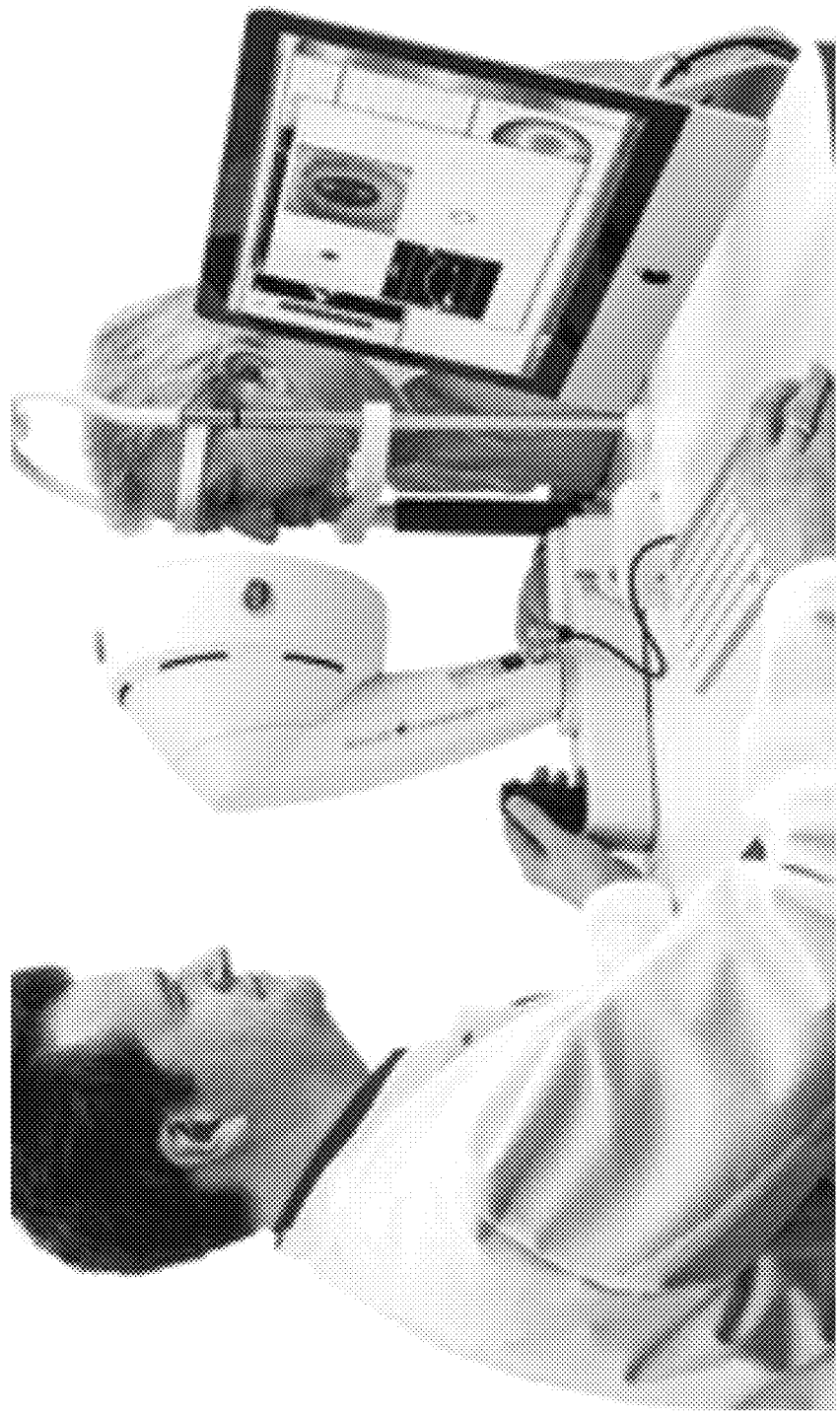
FIG. 3 is a known scanning system in the art, showing the size of the Pentacam™ instrument relative to a patient.

FIGS. 3 and 4 illustrate some known prior art systems that follow a more traditional layout for 3-D scanning of patients. For example, FIG. 3 shows a photo of the Pentacam© system in clinical use. Such system has a moving camera and has an overall diameter of more than a foot to allow for the camera movement. Similarly, FIG. 4 illustrates a LensAR© refractive cataract laser which is an example of a surgical laser system that uses structured light scanning vs. the more common OCT method. Although the LensAR© system does not use OCT, it follows a traditional approach to camera and light source placement for performing the necessary diagnostic measurements of the patient's eye at the objective. In other words, the camera rotates about the objective to obtain the necessary eye structure geometry prior to performing the surgical procedures. It can be readily seen that such systems can be bulky and complex thus creating a need for smaller and less complex systems to perform such measurements.

Many embodiments as disclosed herein aim to simplify the overall design of the 3-D scanning system by removing or reducing the number of moving parts as well as re-aligning the camera and light source such that the camera does not require bulky mechanical devices for rotational movement around the objective. In accordance with many embodiments, the camera remains in a fixed position within the system aside from slight focus adjustments and in many other embodiments the camera remains on axis to receive the feedback light scattered from the patient's eye. With the camera on-axis, the scanning light must be projected into the eye at an angle. In accordance with embodiments herein, the angle for projection of the light is greater than 15 degrees (inclusive) from the Z axis, e.g., in order to provide a useful magnitude of the disparity angle. For example, FIGS. 5A through 6B illustrate various components of the compact 3-D scanning system in accordance with an embodiment. Such features of this herein described 3D scanning system may be incorporated or integrated into a femtosecond laser surgery system.

Figure 5B:
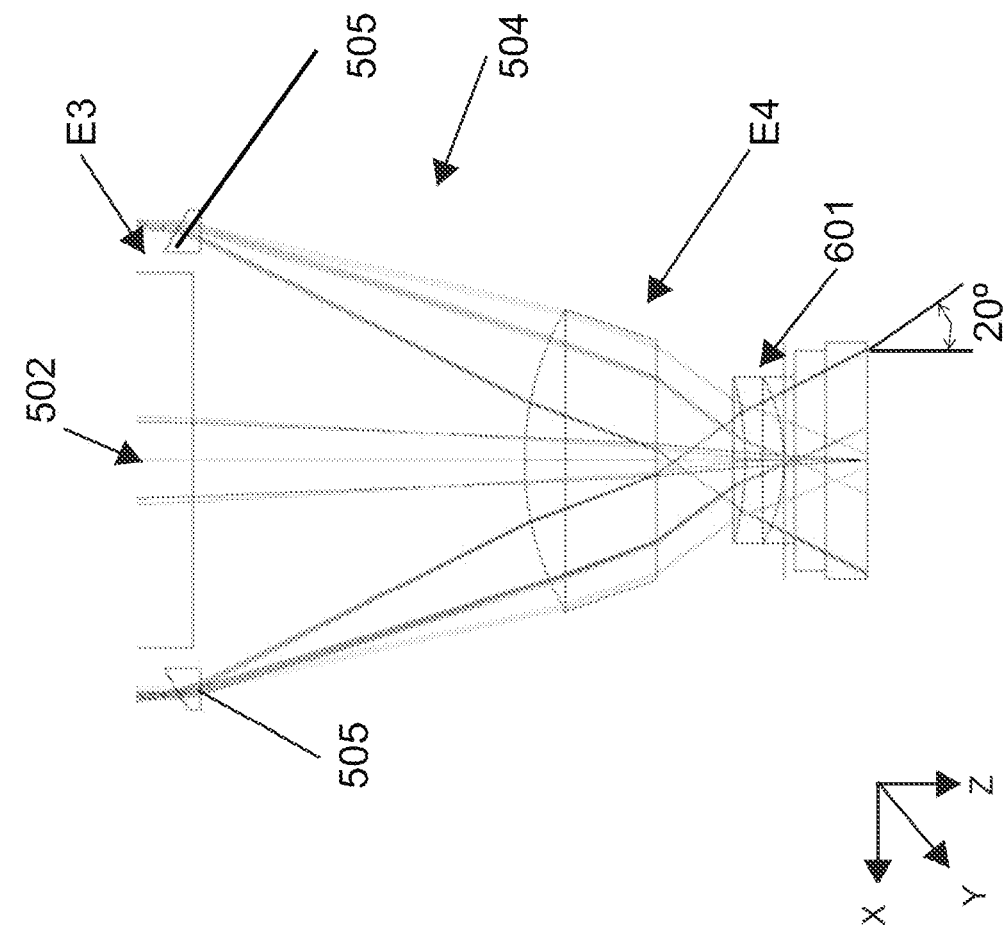
FIGS. 5A to 5C show various components in accordance with an embodiment of this disclosure to illustrate exemplary paths of the 3D scanning beams.
Figure 5A:
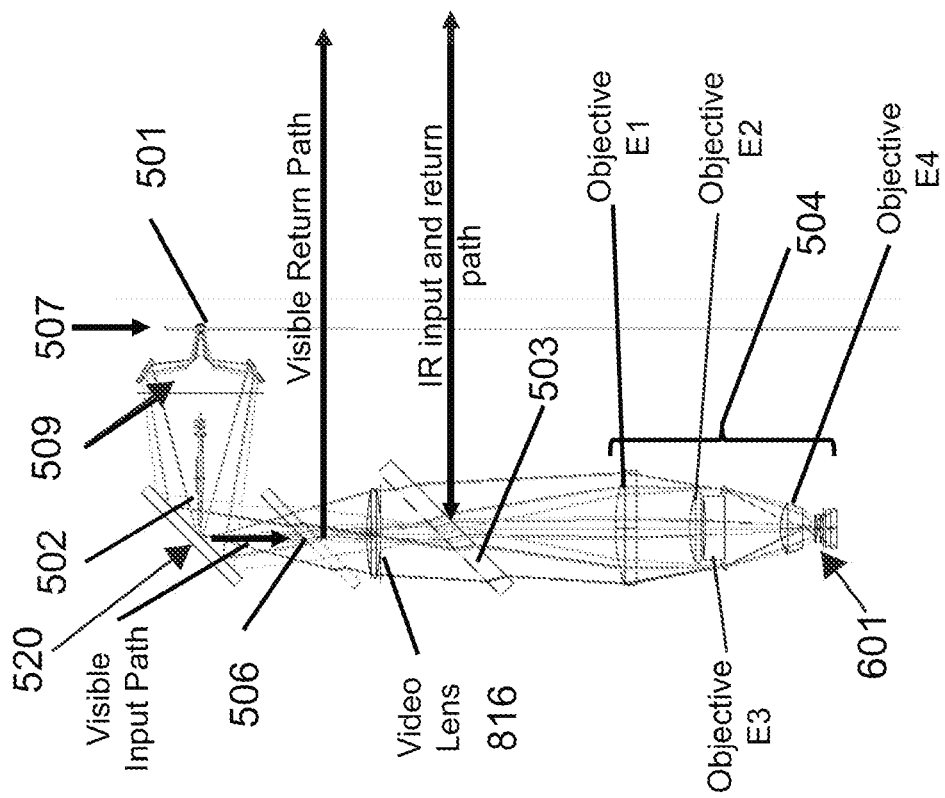

FIG. 5A illustrates one embodiment of various components and exemplary paths of 3D scanning beams in a 3-D scanning system (e.g., subsystem 500 in FIG. 19), in accordance with embodiments herein, having a light source 507 that directs a beam of light towards a plurality of reflective and refractive devices. Such reflective and refractive devices may include, for example, mirrors and prisms, which control a path of the beam(s) of light. In some embodiments, small scan mirrors 501, such as having approximately a 3 mm diameter, for example, are configured to redirect the source light into the system to be reflected and refracted down the desired path to the objective 504 and ultimately up to and through the eye. In accordance with many embodiments, the scan mirrors 501 may be galvo mirrors. Accordingly, to simplify the system the small mirrors 501 may be configured to move with respect to the light source, while no other components need to move to accomplish 3D scanning. The movement of the small mirrors 501 may allow for the angle of the light to be adjusted as it enters the rest of the 3D scanner delivery system thereby adjusting the end position of the light as it exits the objective 504 and into the eye (such as shown in greater detail in FIG. 5B, as well as FIG. 7C). This method of moving the small mirrors with respect to the light source will produce a similar effect as a projected light ribbon on the traditional systems when the light beam is swept along a selected path during the exposure period of a CCD camera. However, the size of the mirrors and movement system can be much smaller than the traditional light ribbon and moving camera system thereby allowing for a reduction in size and complexity of the system. Furthermore, the small mirrors provide beam position control of the beam of light in two dimensions, so in addition to creating a scanned light ribbon in a direction such as the X axis, the lateral position of such a light ribbon can be controlled in a direction such as Y. That is, in an embodiment, the mirrors are configured to provide the beam of light in two dimensions such as the X-axis and the Y-axis, and the object (eye) receives the beam of light at an angle to the Z-axis (such as 20 degrees, as described later). This means that light from each (added) prism is able to scan most of the system field of view. In the most compact system designs, there is typically some clipping due to the size of the various lens edges such that a roughly circular segment closest to a given prism in the field of view cannot be illuminated from that prism direction (see FIG. 6C). However with a distribution of four (4) prisms, for example (such as shown and described later with reference to the exemplary embodiment illustrated in FIG. 6A), the other three (3) prisms can cover the region missed by any one prism, and, in fact, most points in the field of view can be illuminated by all four prisms.

Figures 8A, 8B:
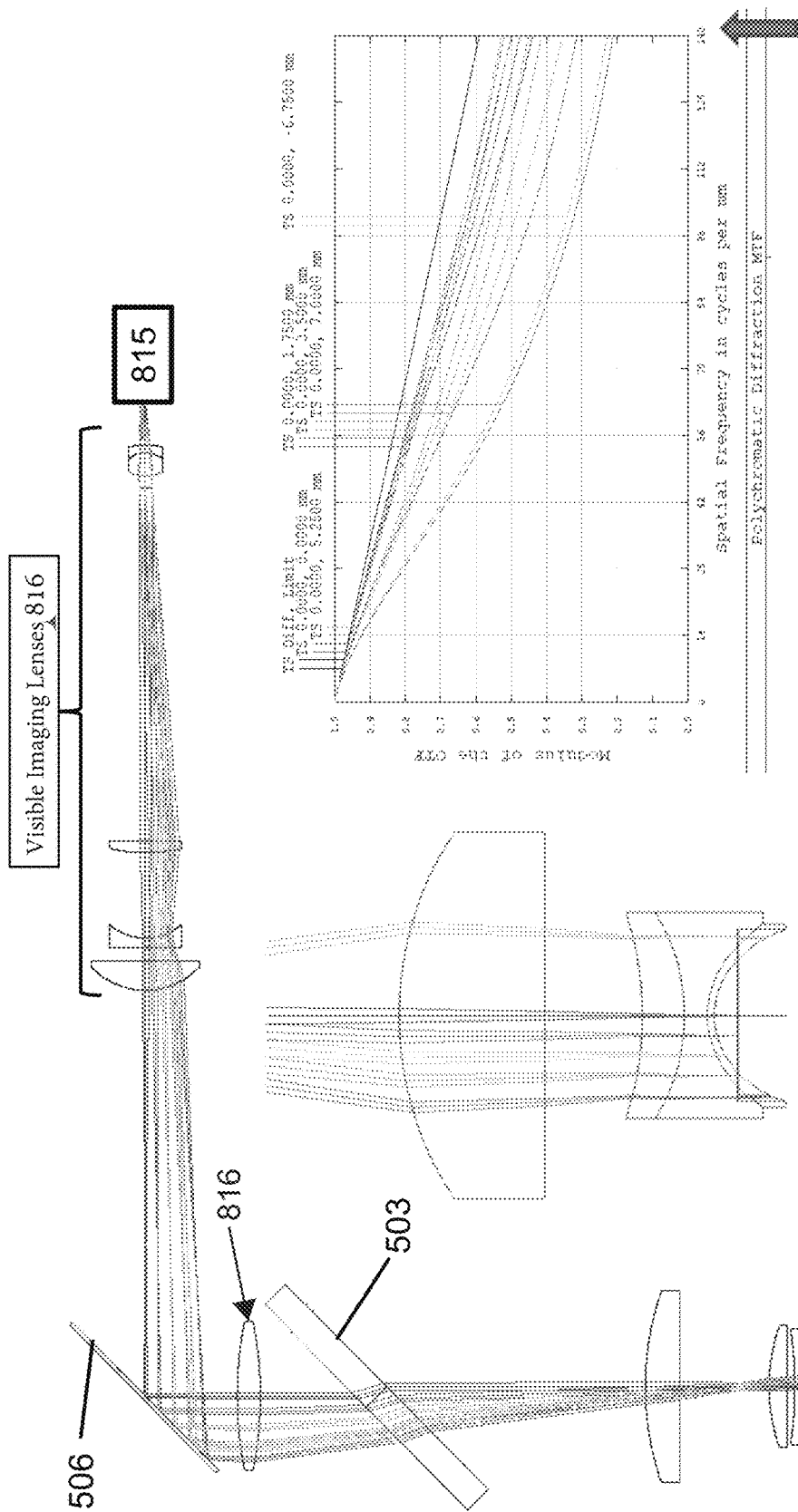
FIGS. 8A and 8B illustrate an embodiment of this disclosure with visible imaging optics and an image sensor which view the surgical field at the output of the objective, in accordance with an embodiment.

In accordance with an embodiment, the 3D Scanner light source 507 may be added to a traditional system by use of the video beamsplitter 506 (shown in FIGS. 5A, 7A, and 8A) which transmits the scanning light beams into the objective 504 while reflecting the image information into the video monitor system (see, e.g., video image lenses 816 and CCD camera 815 in FIG. 8A). To reduce the additional height caused by inserting the 3D scanner light source, usually a scanner fold mirror 520 (FIG. 5A) is added to achieve a more compact design envelope. In some implementations, it may be desirable for the reflectivity of the video beamsplitter 506 to be quite high, such as 90%, since, in this case, the sensitivity of the video monitor system will hardly be affected by losses from the beamsplitter 506. The scanning beam will correspondingly be strongly attenuated on passage through the beamsplitter 506, with a transmission of only 10%, for example. However, since compact and economical visible diode laser sources are available (e.g., with power level such as 30-50 milliwatts which are much higher than safe levels used to illuminate the eye such as 1 milliwatt), it is not a problem in this case that the scanning source will have high losses on the beamsplitter 506, such that the diagnostic beam reaches the eye at a safe power level.

FIG. 5A also illustrates an exemplary implementation for providing an axial illumination source 502 between pyramidal mirror 509 and fold mirror 520. In some implementations, the illumination source 502 may be an on-axis IR illuminator which may be useful for alignment and calibration purposes. In other implementations, illustrated in FIG. 5C, for example, the region between pyramid mirror 509 and fold mirror 520 may contain a patient fixation light 512 and/or an axial scan periscope 510+511 which transforms one arm of the 3D scanner from the original role of providing off axis light beams with a disparity angle into being an on axis scanner with essentially zero disparity angle in the imaging system. That is, at least two mirrors may be added (along with prisms) to a system in order to convert one or more of the usual prism paths into an axial scan function. Such implementations may be useful for initial alignment of the delivery system relative to the patient's position, for example, projecting a cross or concentric circles to assist in the docking process while the objective is initially several inches away from the patient's eye.

The pyramidal mirror 509 may be placed, in accordance with an embodiment, in proximity of the plurality of mirrors which control the path of the scanning/light beam, such that each prism (505) in the objective (504) may be reached by aiming the beam onto a corresponding facet of the pyramidal mirror 509. In an embodiment, there may be substantial overlap of the regions in the object (eye) which may be scanned by each prism 505.

Figures 6A, 6B:
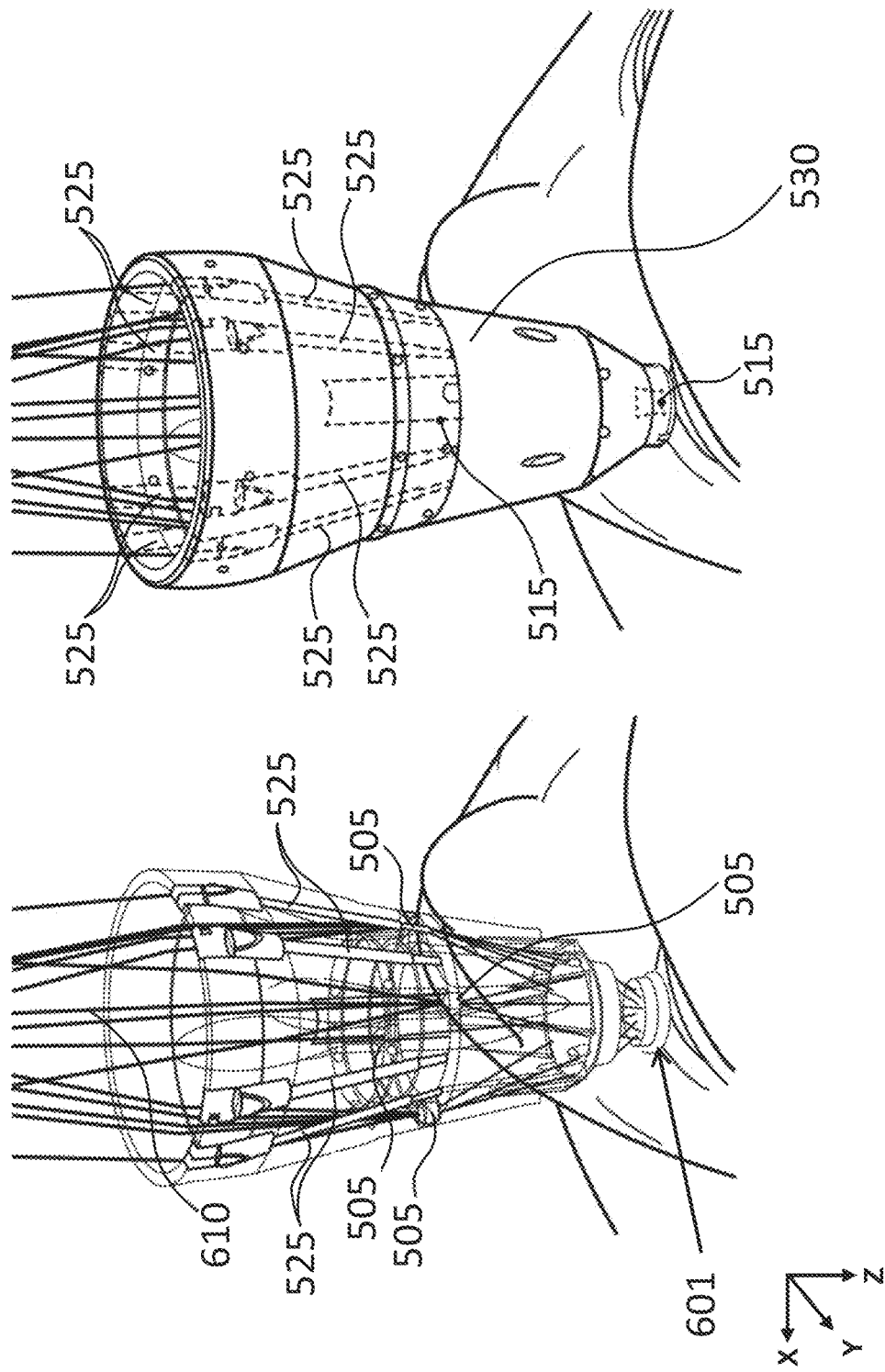
FIGS. 6A to 6E illustrate an embodiment of the objective module of this disclosure showing the size relative to a patient, also showing exemplary paths of 3D scanning beams, prisms, and channels in an objective housing, in accordance with an embodiment.
Figure 6C:
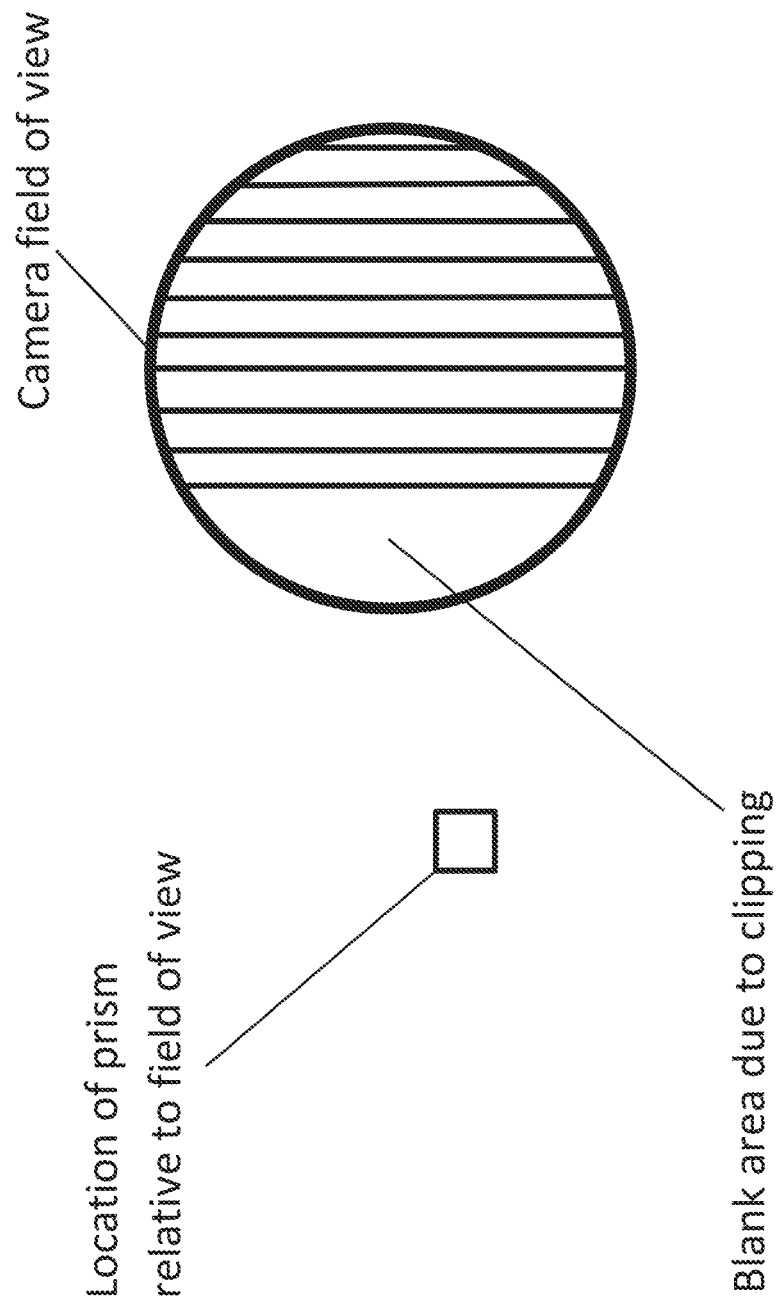

To assist in the scanning function and direct light beams to the object (e.g., eye of the patient), prisms 505 and channels 515, 525 may be added to objective housing 530 of the objective 504. Considerations for adding 3D scanner prisms 505 and internal channels 515 and 525 to the objective housing 530 of objective 504 are illustrated in exemplary embodiments of FIGS. 6A though 6E. An objective 504 is illustrated in FIG. 6A with its outer housing 530 depicted as clear or opaque for illustrative purposes only. FIG. 6B illustrates an embodiment of the objective 504 with an outer housing 530 depicted as opaque. The objective 504, in accordance with an embodiment herein, may be configured to redirect a variety of scanning beams, generally represented in FIG. 6A as exemplary scanning beams 610, that enter the objective 504 at a variety of angles according to the desired end position of the scanning beams 610. As noted, the prisms 505 and internal channels 515, 525 are added to the housing 530 to support the 3D scanning function, in accordance with an embodiment herein. Such features are shown in greater detail in FIGS. 6B, 6D, and 6E. The prisms 505 add only a small amount to the overall diameter of the objective housing 530 (shown in FIG. 6B, for example) of objective 504, relative to the size of the housing already needed (in known systems) to mount only the circular lens elements. Specifically, the prisms 505 are placed outside of the objective lenses E1, E2, E3, and E4 (shown in FIG. 5A, for example). In accordance with an embodiment, as illustrated in FIG. 6A, the prisms 505 may be placed in a middle region of the objective housing 530, such that the 3D scanning light travels or passes through the first and last objective lenses E1 and E4 (respectively), but it will miss the interior objective lenses E2 and E3 and instead travel through the prisms 505. Such a configuration produces a skewed path which is instrumental in generating the herein described (larger) angle (e.g., approximately 20 degrees) to the Z-axis for the scanning light beam(s) of light, as it arrives at and illuminates the object. In the illustrative embodiment, for example, the prisms 505 may be placed adjacent to or near objective lens E3, such as shown in FIG. 5B. In particular, the prisms 505 may be mounted outside a diameter of some of the interior lenses of the objective, such as E2 and E3. This configuration also maintains a highly compact overall size for the objective and its housing 530. In a particular embodiment, the objective lens diameters will decrease going from top to bottom and also have large air spaces between them relative to the center thickness of the glass elements.

FIG. 6A shows one particular embodiment in accordance with this disclosure in which there are four (4) small prisms 505 positioned every 90 degrees generally about the inner circumference along an inner wall of the housing 530 of objective assembly 504. In this case, the disparity angle may be set to have an azimuthal orientation of 0, 90, 180, or 270 degrees around the Z axis, depending on which prism in the objective the light is directed into. In such an embodiment, the objective housing 530 will have an elongated and tapered shape (such as shown in FIG. 6B) which provides good clearance for patient anatomy (e.g., nose and brow) and furthermore provides the doctor with a nearly unobstructed direct view of the patient during the entire procedure. At the output, or bottom, of the objective is the patient interface lens 601—or "PI" lens—(shown in FIG. 6A, for example), which is a component of the patient interface 600 and which provides the optical and mechanical interface between the patient's eye and the laser system. The PI lens 601 may be designed either as a contact interface (CI), generally with a concave final surface designed to press directly onto the cornea, or the PI lens 601 may be designed as a liquid interface (LI), with a typically convex final surface designed to be immersed in fluid such as sterile saline with the cornea facing the LI lens also immersed in fluid. To provide a useful operating region, the PI diameter of the PI lens 601 may be, in accordance with an embodiment, at least approximately 10 mm (inclusive) and up to less than approximately 20 mm (inclusive), to provide good clearance for patient anatomy.

Figure 6E:
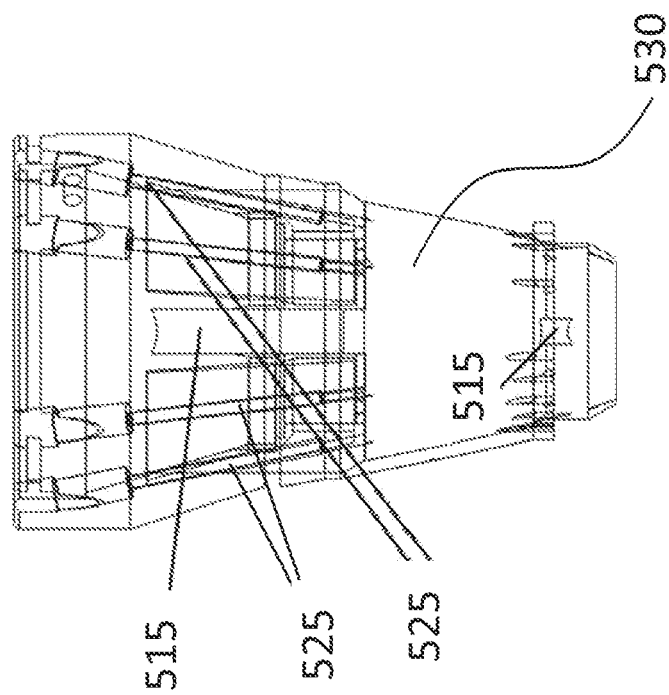
Figure 6D:
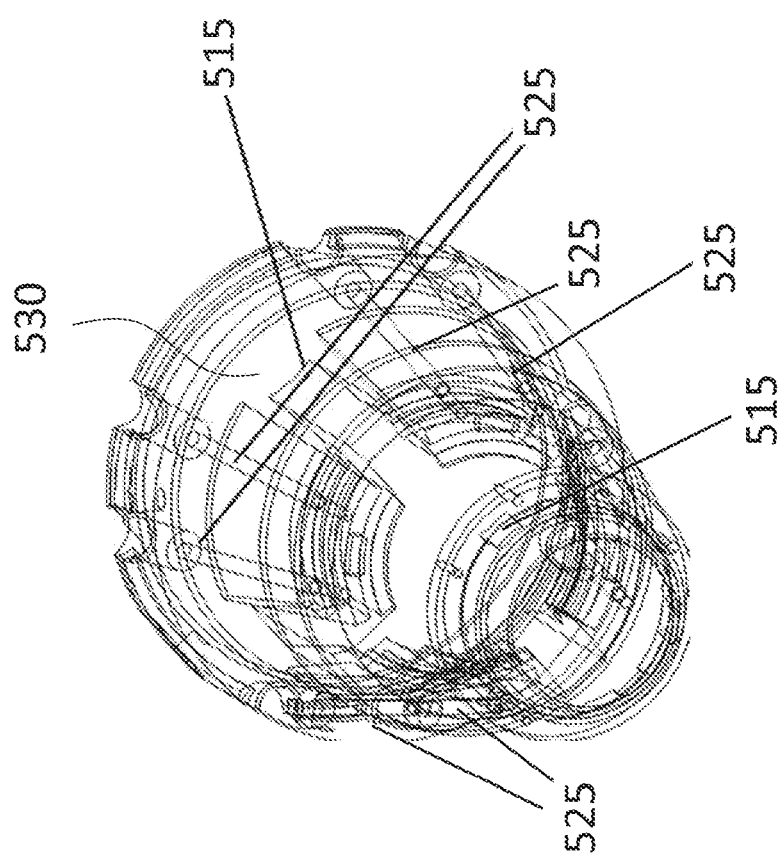

FIG. 6A and FIGS. 6D-6E also show that some internal channels 515 and 525 may be provided, in accordance with embodiments, in the objective housing 530 to allow passage of the scanning beam(s) over its range of scan positions. Channels 515 may be open channels, for the prisms and 3D scanning light paths, that have a depth extending from the inner wall of the housing 530 and into its body (towards an outer wall of the housing), such as seen in FIG. 6D. Channels 515 may be provided in the housing 530 near prisms 505 and objective lenses E2 and E3 and/or near or at a patient interface 600 (such as shown, one side, in FIG. 6E). In an embodiment, such channels 515 may be provided on either side of an objective housing 530, e.g., across from each other. In a particular embodiment, four channels 515 may be provided in objective housing 530. In one embodiment, each channel 515 may be provided adjacent to (e.g., below or near) a position of a prism 505 within the housing 530. In another embodiment, one or more channels 515 may be provided between prisms 505. In yet another embodiment, channels 515 are provided adjacent to, at, or below objective lens E4 and/or near or at patient interface 600. Channels 525 may be closed channels for receiving light pipe fibers for general illumination of the surgical field, i.e., illuminating the object or eye. In this case, each of these closed illumination channels 525 allow a thin light pipe (fibers) to extend along the objective housing 530 and reach down to an output end (at patient interface 600) of the objective housing 530, while any LEDs and associated wiring are provided at a top end of the housing. This is helpful in achieving a compact envelope by moving larger components (like LEDS and wiring) away from the smaller bottom output end. Channels 525 may be formed within a wall (or walls) of the body of the objective housing 530, e.g., formed between the inner wall and the outer wall of the housing 530. In an embodiment, channels 525 may be placed around the objective housing 530. In one embodiment, one or more channels 525 may be placed relatively between two prisms 505 (e.g., relatively adjacent prisms). In an embodiment, one or more channels 525 may be placed relatively between relatively adjacent channels 515. In a particular embodiment, eight channels 525 may be provided in objective housing 530. Of course, any combination of the above described placement of channels 515, 525 may also be implemented in embodiments herein.

Creating suitable internal channels 515 and 525 to pass these rays/beams in the known (metal) objective housing would be complex and expensive with conventional EDM machining, for example. In some implementations, 3D printing the objective housing 530 with a metal (such as titanium) is a cost effective way to produce these necessarily complex internal features and channels 515, 525 of the objective housing 530, in order to accommodate 3D scanning capability. In another implementation, in accordance with an embodiment of this disclosure, a single pass with conventional machining, such as a lathe, is applied to the near net shape 3D metal printed part, in order to economically generate high precision lens mounting surfaces, precise external dimensions, smooth finish, and/or other characteristics difficult to achieve with direct 3D metal printing. That is, in an embodiment, the complex internal features of the objective housing may be produced by a process of 3D printing in metal, followed by a single pass of conventional machining to achieve high precision (where required).

Referring back to FIGS. 5A-5C, the direction of the light into different quadrants may be conveniently implemented by placing a square pyramidal mirror (shown as pyramid mirror 509 in FIGS. 5A and 5C) after the galvo scanners or galvo scan mirrors 501. Any of the four quadrant prisms 505 in the objective 504 may be accessed by controlling the galvos 501 to direct the light beam onto the corresponding face of the pyramid mirror 509. Because the disparity angle may be selected from four (4) different directions, all parts of the eye can be measured with nearly optimum geometry, thus matching the advantage in a traditional system of rotating the camera around the azimuth, but only requiring motion of the small galvo mirrors for implementation. Also, the ability to measure the Z position for a given point in the field of view from multiple disparity directions as provided herein may improve the accuracy of the result by averaging the results for that point from each disparity direction. On the other hand, in a traditional ophthalmic scanner such as those previously discussed, only the center point typically benefits from being exposed with multiple disparity azimuth angles.

While four prisms 505 may be included in the objective housing 530, which are equidistantly spaced at 90 degrees around the inner circumference of the objective 504, it should be noted that the illustrations and above described embodiment is not intended to be limiting. That is, the number of prisms may be altered based on the desired outcome (e.g., more than 4 or less than 4). Further, the positioning of the prisms may be altered such that the spacing between the prisms is adjusted and need not necessarily be equidistant around and along the inner circumference of the objective 504, but does not necessarily need to be at ninety (90) degrees. Rather, in some cases, a smaller angle (e.g., 45 degrees) or else larger angle may be utilized (e.g., 72 degrees or 120 degrees). In accordance with an embodiment, each of the prisms 505 are symmetrically arranged around the objective 504 and the pyramid mirror 509 may have a base of a triangle or pentagon. In another embodiment, the prisms 505 may be arranged around the objective 504 with 90 degree angles therebetween along with a square pyramid mirror 509, in order to provide a range of disparity angles and a relatively straightforward design.

As light is directed through the system, it may be reflected and/or redirected by a number of additional lenses and/or beamsplitters 503 and 506. The beamsplitters may be positioned such that the scanning light source is directed to the patient's eye and the scattered light from the patient can be efficiently redirected to a camera system, such as the imaging lenses 816 plus the image sensor (i.e., CCD camera) 815 depicted in FIG. 8A. Ultimately, the lenses and/or beamsplitters 503 and 506 aid in generating a structured light that will enter the objective assembly 504 to be directed to the patient's eye at a substantial angle α to the camera viewing axis, i.e., to the Z-axis. FIG. 5B shows details of one embodiment where the scanning light exits the objective 504 shown with a liquid interface LI lens 601 (also shown in FIG. 6A) with approximately a 20 degree angle α to the Z axis, i.e., the rays below the concave surface of the LI going into a uniform medium. While in FIG. 5B the eye structures are not shown in order to clarify the angled exit path of the light, in FIG. 7C, the representative beam paths are shown in greater detail along with cornea of the eye and lens structures.

The objective 504 is the component that ultimately directs the 3D scanning beam of light into the patient interface lens 601 and on to the patient's eye (or object) to measure the geometry with laser triangulation. In accordance with some embodiments, the objective 504 may be configured with a number of prisms 505 mounted inside the physical structure of the objective 504. The prisms 505, according to many embodiments may allow the structured light to enter the eye at substantial angles, such as 20 degrees as shown in FIG. 5B, thereby eliminating the need for additional bulky equipment to achieve the precise measurements that are desired and necessary for proper diagnosis and ultimate treatment. Some embodiments having prisms may allow the structured light to enter the eye at an angle α, such as approximately 20 degrees. In accordance with other embodiments, the disparity angle α (i.e., the angle to the Z-axis at which the structured light enters the eye, i.e., as a result of the scanning light exiting the objective 504 and being directed to lens 601) is at least approximately 15 degrees. In another embodiment, the disparity angle α at which the structured light enters the eye is between approximately 15 degrees to approximately 25 degrees (both inclusive).

Figure 5C:
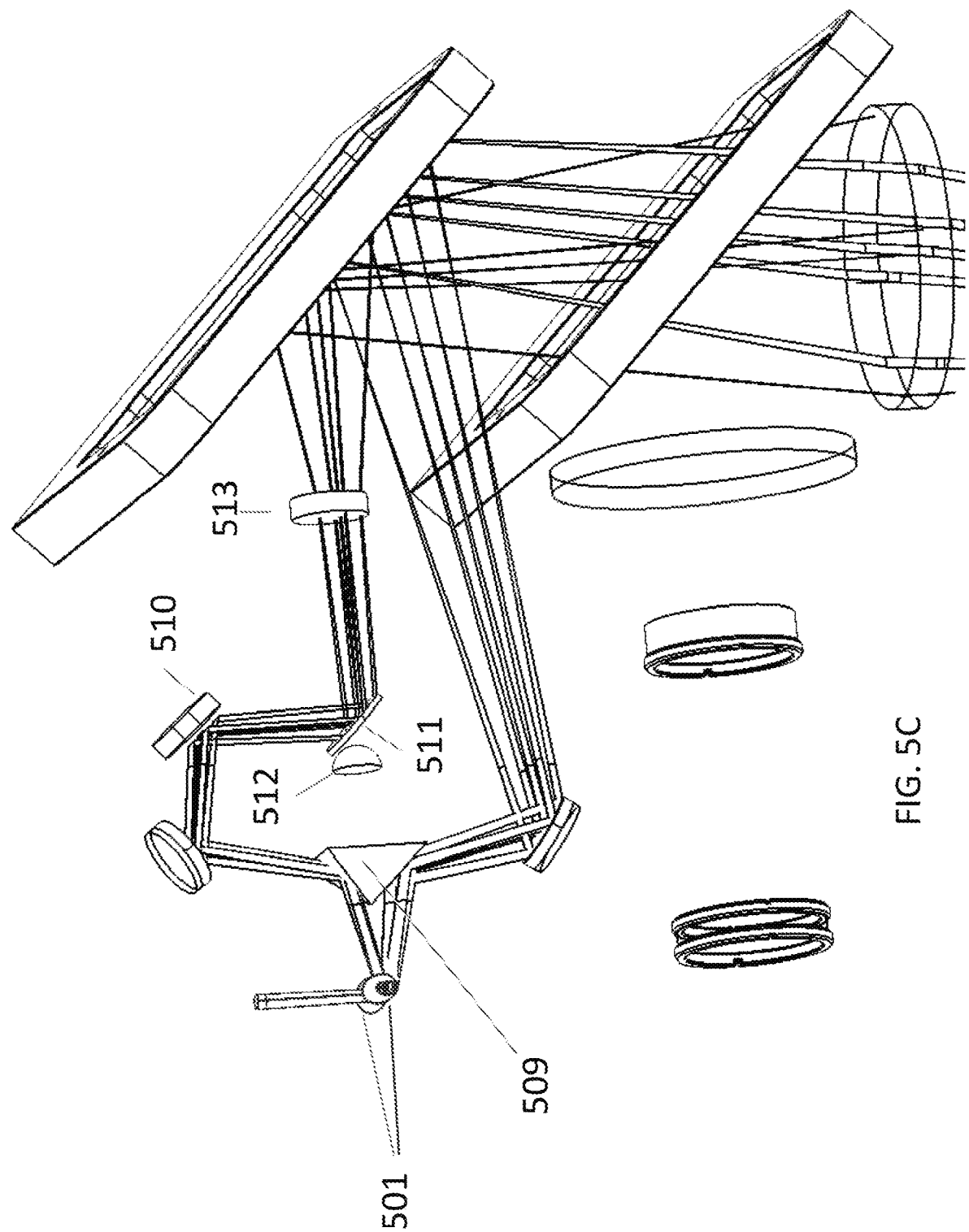

In some cases it may be desired that one of the scan sectors be converted to a coaxial output from the objective. Since the field of view is covered from multiple sectors, the removal of any one sector will not prevent any particular part of the field of view from being measured. Although not useful for 3D scanning, an axial scan beam may be desired for other purposes, such as projecting a concentric circle pattern for setting up the initial alignment of the objective to the patient's eye. An example of adding two (2) mirrors and one (1) lens to convert a 3D scan sector into an axial scan is shown in FIG. 5C. For clarity only, two (2) sectors are shown in FIG. 5C, the path going down from the pyramid mirror 509 is a standard 3D scan sector shown for reference, while the path going up from pyramid mirror 509 has been converted to axial by the mirrors or periscope 510 and 511, then the negative lens 513 acts to increase the available angular scan range for the axial scan.

The mirror 511 may be chosen to be a dichroic mirror in order to support the function of a fixation light, i.e., a visible light in the center position to assist the patient in directing his or her gaze. For example, the 3D scan laser beam may be green while the fixation light may be red, and the dichroic mirror 511 may be selected to transmit red and reflect green. In this case a light source (not shown) is collimated by the lens 512, transmitted through 511 and 513, and will appear in the center position when viewed by the patient for the function of a fixation light. It is also possible to use the fixation light without converting any sectors to the axial mode.

FIG. 7B shows a more detailed representation of the scanning beams 610, shown here as beams 610A, 610B, 610C, 610D, 610E, and 610F. As shown in FIG. 7B, each of the beams 610A-610F are redirected at a different angle once directed through one of the prisms 505 (e.g., one of the aforementioned four prisms 505, in accordance with an embodiment). Many embodiments achieve the direction of the scanning beams 610 with prisms 505 located within the objective housing 530.

The number of scanning beams 610A-610F as provided in the illustrated embodiment (in particular, FIGS. 7A-7C) is not intended to be limiting; the beams shown represent the approximate full scale range of the scan projection into the target region for each choice of prism 505. In practice, the light beams scan in continuous patterns, such as a raster scan, and are projected through each prism in a sequence. In one implementation, the control system will trigger the CCD camera 815 in coordination with the action of the 3D scanner light beam, to rapidly (e.g., less than 5 seconds) acquire a sequence of images in which each image has the 3D scanning beam traversing a predetermined region (for example, one line out of a raster pattern). Each such image may be analyzed with standard laser triangulation methods to find the X,Y,Z coordinates of features of an object in a viewing region of the objective illuminated by the 3D scanning beam. Such features may include anterior and posterior surfaces of the cornea of the eye or lens capsule, as may be needed for planning the surgical laser cutting path, or may include the iris or sclera, as may be needed for monitoring docking stability, i.e., potential unwanted movement of the eye during the course of anatomy measurement and delivery of the surgical cutting beam. In one embodiment, the viewing region of the objective is an anterior portion of an eye to be dimensionally measured.

A very compact envelope results from placing the prisms 505 at a conjugate plane to the galvo scan mirrors 501 such as shown in the example optical design layout of FIG. 5A. The conjugate plane is determined by 2 refractive elements in this example, the exterior video lens 816 and the E1 objective lens. In this case the beam footprint on the prism will be small even though the beam is scanned over the entire available angular range, thus the prisms 505 are able to have a small size such as 6 mm width in some embodiments. The small size of the prisms 505 may only increase to the size of the objective housing 530 slightly, compared to the size already needed to hold the lens elements which focus the surgical laser beam.

Turning now to FIGS. 7A-7C, as a result of the skewed beam path through the outside portion of the E1 and E4 objective lenses and external video lens 816, each of the scanning beams 610 will necessarily be affected by a substantial degree of astigmatism and this means it is not possible for the output beam to be small at any particular location in both radial and tangential directions. In accordance with an embodiment, the astigmatism (or the degree thereof) imposed on the scanning beam(s) by traversing a marginal portion of some refractive elements in the path is controlled so that a narrow astigmatic beam dimension is perpendicular to a rapid scan direction used to generate a light sheet with the best resolution. In FIG. 7A, the rays or scanning beams are labeled 610A, 610B . . . to 610F to show the change of direction of each beam/ray as they pass through one of the prisms 505. The radial direction for a given prism 505 is the direction from that prism to the center axis (Z axis) of the objective 504 while the tangential direction is orthogonal to both the radial axis and the Z axis. However, the astigmatism is not a disadvantage for the many embodiments of the disclosure because the light beam may be scanned rapidly in the tangential direction in order to create a sheet of light for each video frame that is acquired. Because the beam is intentionally spread out in the tangential direction by the action of the small scan mirrors 501, it is only the radial dimension of the scanning beam which determines the spatial resolution of the data. Therefore, the input laser beam to the small scan mirrors 501 may be adjusted in focus characteristics so that the radial beam size is minimized. In accordance with embodiments, the scanning visible laser beam may have a radial beam size that is less than 100 microns, throughout the region of the eye that will be scanned, such as a range of 0 to 10 mm past the output of the patient interface lens.

In FIGS. 8A and 8B, an embodiment of the CCD camera and its imaging optics for the 3-D scanner, in which a beamsplitter 506 directs a large percentage of the light returning from the eye into the camera optics 816, is illustrated, which is part of a video camera system. In accordance with an embodiment, the camera system which receives the 3D scanning images is the same camera system used for the doctor's surgical display. In one embodiment, the imaging lenses 816 of the camera 815 consist of inexpensive commercial stock singlets and doublets.

Many embodiments herein may use a beamsplitter 506 with a high reflectivity, such as 90% reflective, which means that the scanning beam will be greatly reduced in power while passing through the beamsplitter 506. However, some embodiments may use small diode lasers available at low cost, which have considerably more power than may be necessary to perform accurate measurements of the eye. Such embodiments will allow the detection system to be nearly as sensitive as possible, while most of the scanning laser power is rejected by the beamsplitter.

In the exemplary embodiment illustrated in FIG. 8A, the visible imaging optics or imaging lenses 816 may be chosen during the design phase to be commercial catalog singlet and doublet lenses which are available at much lower cost than the traditional imaging system design approach of using custom designed lenses and/or high precision multilens assemblies. The imaging performance of this representative design is shown in a standard MTF plot in FIG. 8B. The arrow at the 140 cycle/mm position signifies the Nyquist resolution limit of the CCD in this example. Since the imaging lenses 816 provide significant contrast up to and beyond the resolution limit of the sensor, the performance is thus shown to be camera limited despite the use of inexpensive focusing elements. The inset to FIG. 8A shows that this representative imaging system is telecentric (as evidenced by the vertical paths for light at all positions across the viewing field). Telecentricity is frequently a valuable characteristic for machine vision imaging systems because telecentric image data is simpler to analyze than non-telecentric image data.

Regarding the design of a femtosecond laser delivery system suitable for eye surgery or other volumetric (as opposed to surface) processing of transparent material, the method of scanning the beam in the X and Y directions is of paramount importance. A preferred method with a minimum weight and complexity of moving parts is to use galvanometer mirror scanners. The optical invariant is an important conserved quantity in an optical system; in the case of galvo scanners (such as 501, described previously for 3D scanning of a cw visible beam, and as later described below with reference to components 405-1, 405-2, and 405-3 in a laser guide module 400), the optical invariant dictates that the product of beam size and scan angle range is a fixed quantity whose value defines a fundamental performance metric of the system. The size of the galvo mirrors 501 must be small in order to enable high speed scanning required for short procedures (such as less than 10 seconds) and, therefore, the optical scan angle generated by the scanning galvo mirrors must be large in order to provide a useful magnitude of the optical invariant. In accordance with an embodiment, the size of the galvo mirrors 501 may be approximately 14×20 mm, with each mirror having an elliptical shape. In an embodiment, the optical angle generated by the galvo mirrors is between approximately 35 degrees to approximately 50 degrees (both inclusive). A consequence of the large scan angle is that a telescope is required between the X,Y scanners and the final focusing objective to provide a larger beam, such as 50 mm diameter with a smaller scan angle, such as 10 degrees, which are needed for an objective with practical dimensions. This telescope is provided by a combination, designated as 480 in FIG. 10C, of the scan module 410 with the focus module 430.

The phenomenon of pupil wander will occur in two mirror XY galvo scanners which are commonly employed for 3D scanning. In accordance with embodiments disclosed herein, for surgical laser scanning, a 3 mirror XY galvo block of galvo scan mirrors, such as mirrors 405-1, 405-2, and 405-3 as shown in FIG. 10D, may be used to solve pupil wander, since pupil wander may not be acceptable in laser scanning systems which must produce a nearly diffraction limited spot using a high NA, such as 0.3. While it generally is common practice to employ a 3 mirror galvo set in high precision scanning applications, below are disclosed particular design improvements of a 3 mirror galvo set. With a 3 mirror galvo set, the first 2 mirrors are arranged on 1 axis, such as X1 and X2, and the 3rd mirror is arranged on the other axis, such as Y. The motion of X1 and X2 are combined so that the laser beam footprint is centered on the Y mirror while a wide range of X scan angles may be applied. In this case, the pupil is fixed on the Y mirror for any choice of X-Y scan angles and therefore there is no pupil wander.

Figure 10B:
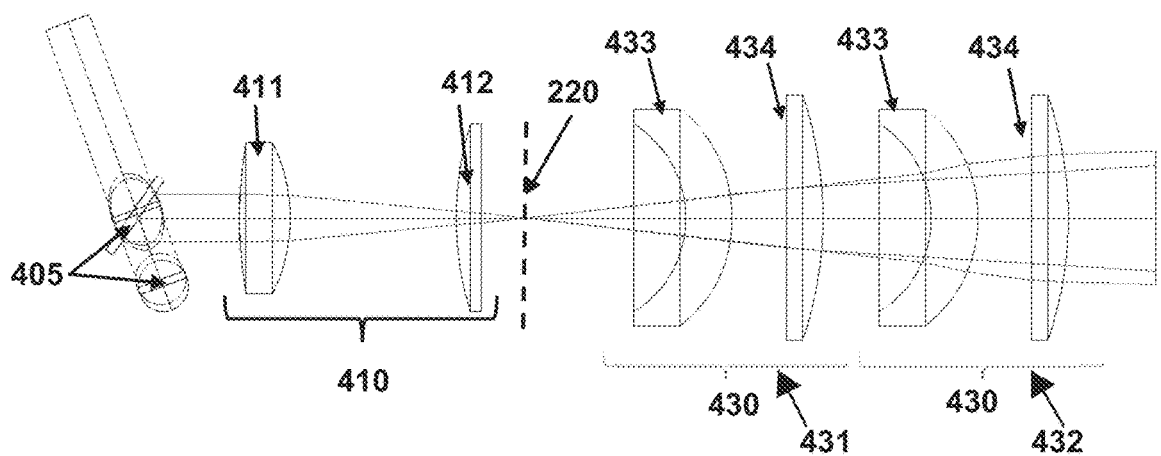
FIGS. 10B-10D illustrate various components of the laser shaper and demonstrate the low number of lens elements required to implement a simplified design, in accordance with an embodiment.
Figure 10C:
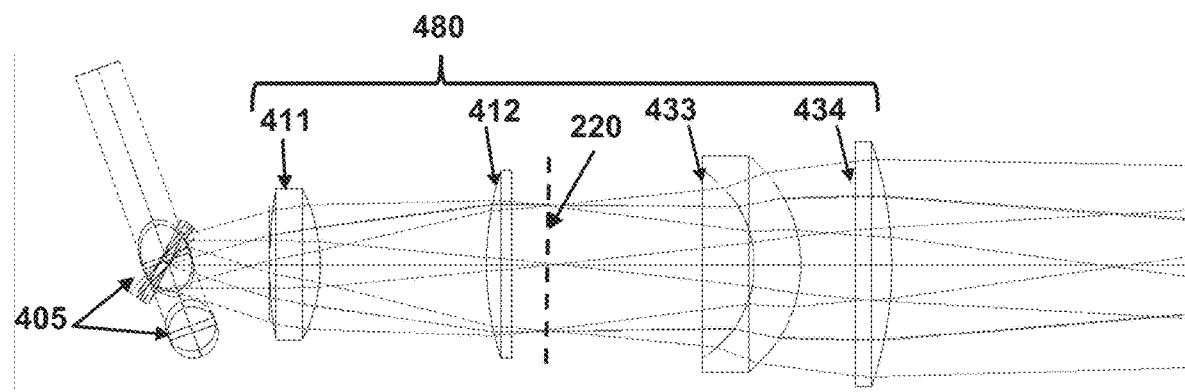
Figure 10D:
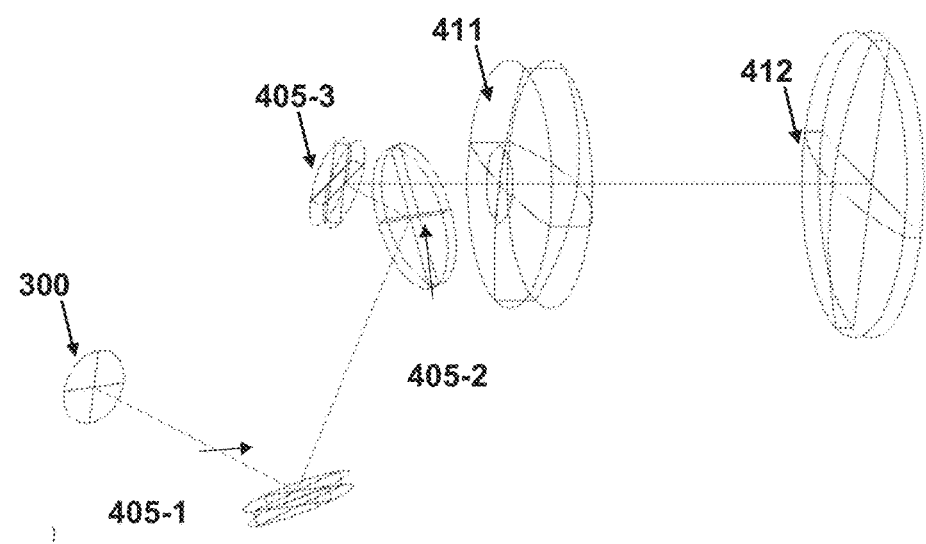

An improved configuration of a 3 mirror galvo block (or galvo group) for the laser shaper is illustrated herein in FIGS. 10B and 10C, labeled generally as mirrors 405, and shown in more detail as mirrors 405-1, 405-2, and 405-3 in the perspective view in FIG. 10D. The three-mirror galvo group/block is configured to reduce an angle of incidence on a second mirror and a third mirror of the group. One improvement may be the use of 35 degree angle of incidence for the beam onto the second mirror 405-2 and also the third mirror 405-3. This results in a more complex mechanical layout as compared to the traditional use of 45 degree incidence beams, because of the intermediate skew angles. However the beam footprint with a 35 degree incidence is 15% shorter than with a 45 degree incidence, thus a 35 degree incidence, for example, allows a larger beam to fit on a given mirror compared to 45 degrees. It is traditional in 2 mirror galvo sets to employ a reduced incidence angle such as 35 degrees; here, this method is extended to the 3 mirror galvo design. Another improvement provided by the disclosed 3 mirror galvo block/group configuration concerns the spacing of the mirrors. Generally, for the highest scanning speed capability, it is preferred that the first mirror 405-1 and second mirror 405-2 have a large spacing therebetween, while the second mirror 405-2 and third mirror 405-3 have a minimum spacing therebetween. Accordingly, in an embodiment, a distance between a first mirror and the second mirror in the three-mirror galvo group is greater than a second distance between the second mirror and the third mirror. In this manner, the required angular movement of the middle (second) mirror 405-2 will be as low as possible for a given range of angle output. Essentially, the first mirror 405-1 must generate a position offset so that, with any choice of scan angle of the second mirror 405-2, the beam has the same position at the last (third) mirror 405-3. By placing the first mirror 405-1 at a long distance, the required position offset may be achieved with a smaller angular excursion of the first mirror. In a 3 mirror galvo design, the second mirror 405-2 has to move to an angle equal to the sum of the desired output angle plus the angle imposed by the first mirror 405-1. By reducing the first mirror scan angle due to a longer separation to the second mirror, the extra motion needed by the second mirror is minimized. Similarly, by reducing the spacing between the second and third mirrors to the extent possible before the mirrors collide, the pupil wander due to the second mirror acting alone is reduced, which again leads to a lower angle motion needed on the first motor to prevent pupil wander, and thereby a reduced angular range on the second mirror. The angular range of the second mirror will always be the largest of the three for a given choice of X-Y scan range, therefore the system performance may be optimized when the angular range of the middle mirror is as small as possible to achieve the required scan range.

It may also be required for the optical design to include a relatively large diameter beam splitter between the focus and objective modules; this is due to the requirement for measurement and diagnostic functions needed to accurately guide the laser. These diagnostic functions, such as video monitor, also need to work through the objective in order to have a compact design. The beam splitter combines the optical path between the treatment laser and the visible light based optical measurement functions. Thus, the minimal topology for a galvo based laser delivery system with diagnostics will consist of the galvos, a beam splitter, and 3 optical modules each of which transfer the light beam between a state of nearly parallel propagation and a state of nearly passing through a single point in space, i.e., a focal point. In general, all 3 modules could be termed as objectives based on transitioning light between collimation and focus, but as defined here, only the last module which generates the focus in the target is called the objective module.

Embodiments of the system and method are directed to, a type of a laser delivery system for an ophthalmic surgery laser system. In accordance with some embodiments, the laser delivery system may be designed using encircled energy as its merit function rather than the RMS wavefront error which is typically used to design imaging and many other types of optical systems. Additionally, the laser delivery system may be designed such that the modules are not infinity corrected which in turn simplifies the structure of the system and may ultimately reduce the overall cost of production due to the reduction in complexity of design and components that is possible by removing the constraint of infinity correction.

Figure 9:
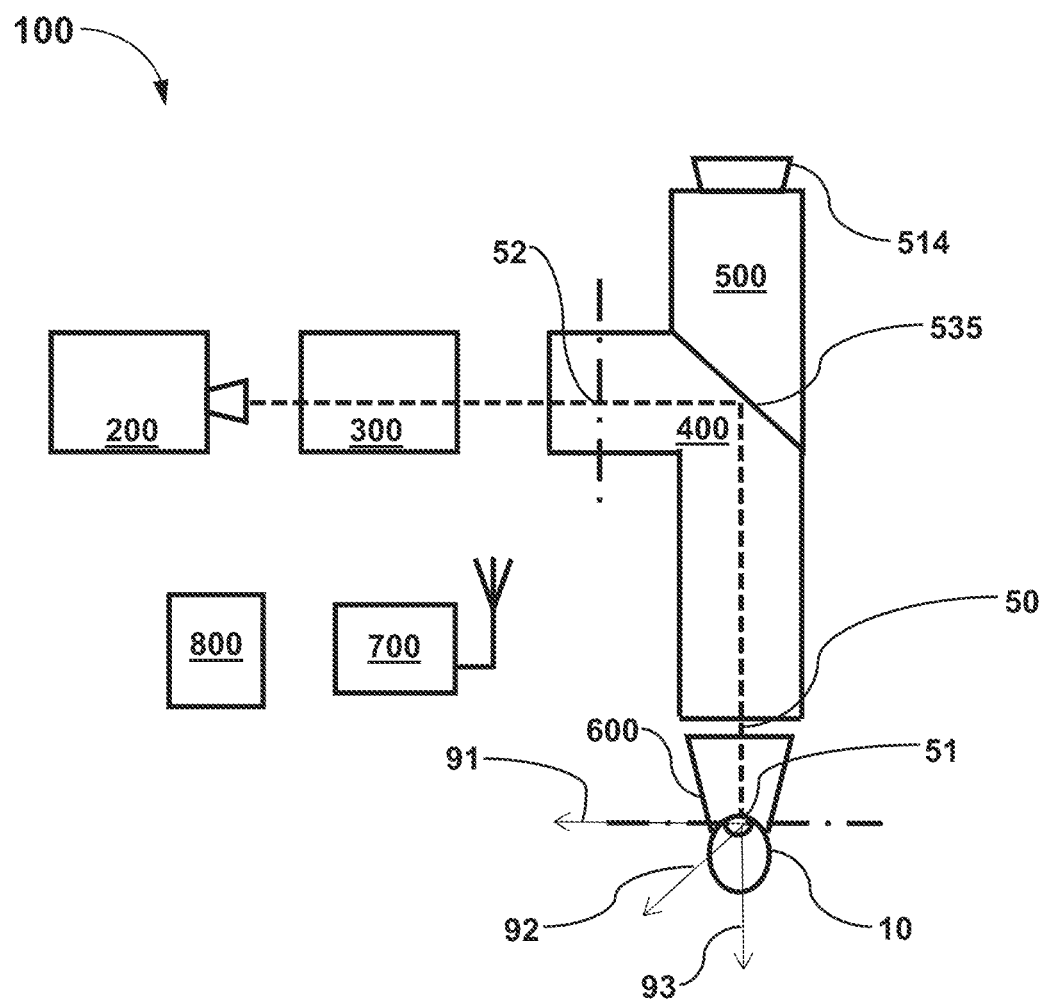
FIG. 9 schematically illustrates an ophthalmic surgery laser system, in accordance with an embodiment.

FIG. 9 schematically illustrates an ophthalmic surgery laser system 100. The ophthalmic surgery laser system 100 ("system") may be configured for a plurality of eye surgeries which may include cutting or laser processing of transparent tissue or implanted material in the course of intraocular surgery. The surgeries may be performed by focusing a laser beam 50 at a point or focus 51 coincident with the patient's eye 10 and manipulating its position and/or strength, the strength of the laser effect being dependent on factors such as laser wavelength, pulse duration, spot size, and repetition rate. In particular, the system 100 may be configured to move the position of the focus 51 in three dimensions in and about the patient's eye 10. For convenience, a frame of reference including a customary X-axis 91, Y-axis 92, and Z-axis 93 is used herein, where the Z-axis 93 originates at the surface of the patient's eye 10, pointing inward and located on the centerline of the field of view.

The system 100, in accordance with many embodiments, may include a laser engine 200, a beam shaper 300 (also referred to as a laser shaper herein), and a laser guide 400. The laser engine 200 may be a regenerative femtosecond laser amplifier configured to provide a repetitively pulsed femto second laser beam collimated along a laser axis. It is understood the laser axis may be reoriented relative to an inline mirror. It is further understood that the laser axis may be at least in part coaxial with the Z-axis 93.

The laser guide 400 may be configured to move the focus 51 along the X-axis 91, Y-axis 92, and Z-axis 93, through a range such as 13 mm in X and Y, 9 mm in Z. Although not shown in the block diagram, the laser guide 400 may include a plurality of mirrors (e.g., galvo mirrors) configured to steer the laser beam 50 such that the focus 51 generally travels in the X and Y direction. The laser guide 400 may also include a plurality of movable lenses configured to move the focus 51 generally in the Z direction; more explicitly described in reference to FIGS. 10A-10D. The movable lenses may travel a relatively long distance, such as 80 mm, in order to move the focus by a shorter distance such as 9 mm in Z.

The laser shaper 300 may be configured to impart a variety of characteristics to the laser beam 50. The laser shaper 300 may also include the "fixed optics" of the system, such as beam transport from the laser source. Generally, the laser shaper 300 may expand or contract the diameter of the laser beam 50, and in addition the clip level at which the Gaussian beam profile is truncated may be controlled.

The laser guide 400 may be configured to impart an angle on the laser beam 50 relative to the laser axis, create an intermediate focus 52 in free space (i.e., not within or near the surface of a lens or mirror), and/or create the focus 51 that may be used for surgery, for example. As discussed in greater detail with reference to FIG. 10A below, the laser guide 400 may include a plurality of lenses, which may be arranged in a plurality of modules associated with a particular characteristic desired from the beam 50. According to one embodiment, the laser guide 400 may include a scan module 410 (also referred to herein as a scanning module), a focus module 430, and an objective module 450.

Figure 12:
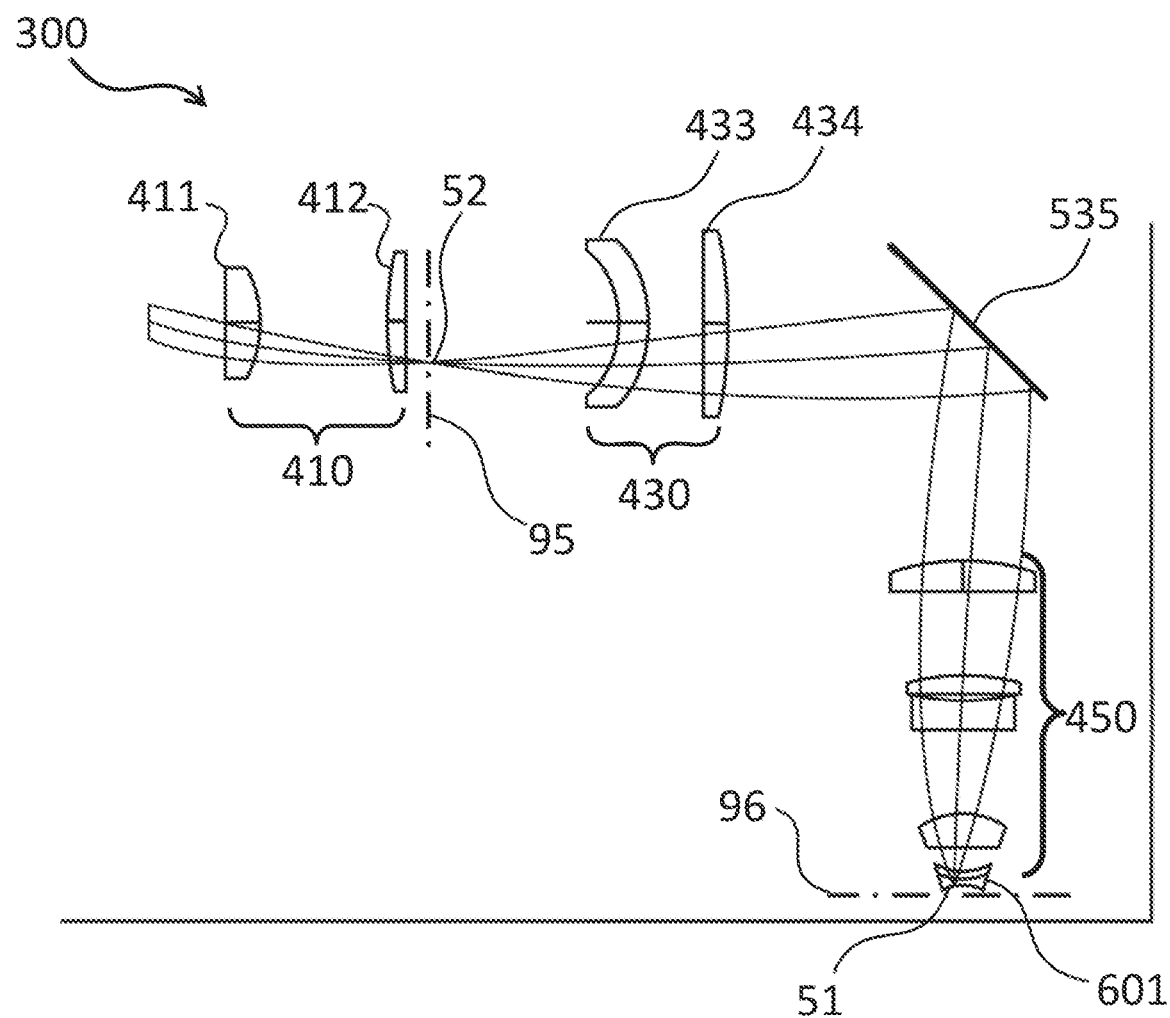
FIG. 12 shows the optical design of the laser guide components of an exemplary laser delivery system, in accordance with an embodiment.

As a result of the large magnitude of the scan angle of the galvanometer mirrors, such as 45 degrees, a telescope (also referred to as a beam expander further illustrated in FIGS. 10A and 12), may be placed after the galvo mirrors 405 (shown in FIG. 10C) and before the objective 450. The beam expander 480 increases the beam size while reducing the scan angle to practical dimensions so that the objective can focus the beam onto the target. In the context of FIGS. 10A and 12, the lens elements of the scan and focus modules taken together may comprise a beam expander, indicated as 480 in FIG. 10C, which transforms the small beam/high angle output from the galvos 405 into a large beam/small angle output suitable for processing by the objective 450, thus the essential optical function of a beam expander is in effect. In the present discussion, the focus 410 and scan 430 modules are defined separately and usually not referred to in combination as a beam expander, in order to emphasize their additional control functions.

The system 100 may further include an imaging subsystem 500, a patient interface 600 and a diagnostic subsystem 700, each of which are schematically represented in FIG. 9. The imaging subsystem 500 may be configured to provide real-time imagery of the surgery to an operator. It can be advantageous when the imaging subsystem is designed to use inexpensive commercial singlet and doublet lenses for all the functions needed within the 500 block, thus implementing further cost reduction compared to the traditional use of custom made lenses in order to implement an imaging subsystem. The imaging subsystem 500 may include a display such as real-time video camera 514 or other streaming device. The imaging subsystem 500 may further include a beam splitter 535, which may include features similar to or the same as the aforementioned and described beamsplitters 503 and/or 506, such that the operator may view the patient's eye during procedure setup and laser operation, or transmit other light beams used for diagnostic measurements, such as optical coherence tomography or structured light scanning.

The patient interface 600 is configured to interface with the patient's eye 10, stabilizing the eye 10 while providing access to the laser beam 50. According to one embodiment, the patient interface 600 may include a liquid interface at the eye 10, which is well suited for procedures on both the cornea and lens tissues. In one embodiment, a moderately scattering fluid is placed in contact with the patient interface lens 601 of the patient interface 600 in order to make LSCM measurements on the PI lens surface location outside of the central area where specular reflection can be measured. In conjunction with the liquid interface, a disposable, transparent sterile barrier may be placed between the eye and the final glass surface where the laser is output, i.e., the surface traversed by the femtosecond laser beam. Such a barrier avoids the need to sterilize or dispose of the final glass element due to sterility concerns, and thus improves cost-effectiveness. According to another embodiment, the patient interface 600 may comprise a solid or semi-solid material in contact with the eye, which is termed a contact interface. A contact interface may provide better stability for performing corneal surgery compared to a liquid interface, however the resulting applanation (i.e., distortion in shape) of the cornea may be inclined to produce posterior corneal folds which are disruptive for directing the beam focus onto the crystalline lens, and this effect restricts the use of contact interfaces away from cataract (lens) procedures. Also in the case of using a contact interface, a flexible sterile barrier may be useful to include between the eye and the applanating surface. As with a liquid contact, a bio-barrier provides a convenient means of assuring sterity for the patient contact, but in addition, the bio-barrier allows the re-use of the costly high precision contact glass even with using the choice of penetrating cuts which open the surface of the cornea. This is because a penetrating cut must go through and also slightly above the cornea (termed the overcut) to assure a reliable cutting effect. This cut penetration into the contacting material will damage a glass lens in direct contact with the eye, however in the case that a barrier film is present with a layer thickness of 100 um for example, then while using a laser overcut of, for example, 30 um above the cornea, the glass will be protected by approximately a 70 um safety margin. This protection of the glass provided by the sterile barrier enables a more cost effective contact interface deployment whereby a single precision lens is re-used many times, as compared to the traditional disposable interface in which case each laser procedure uses a piece of precision glass one time only.

The diagnostic subsystem 700 may include one or more sensors and may be configured to communicate sensed data indicating or otherwise correlating to the functional status of the system 100, for example, to remotely diagnose the functional status or operational "health" of the system 100, for example diagnostic information readings from the laser engine, or internal calibration procedures which could be enabled among the laser shaper and laser guide actuators and sensors.

A controller 800 may control one or more components. For example, the controller 800 may operate at least one of the laser engine 200, the laser shaper 300, the laser guide 400, and the imaging subsystem 500. The controller 800 may include a processor, memory, user interface, and communications link. The controller 800 may reside within the system 100, or may be located remotely or otherwise off-board the system 100. According to one embodiment, the controller 800 uses input data from the operator and the diagnostic data from measuring the eye to customize the operation of the various built in procedures such as flap cutting, lens fragmentation, etc. The controller may accept input from the physician operating the system to define the desired type of procedure and combine this information with the diagnostic data from the patient being treated in order to determine a customized scanning pattern for the X,Y,Z positions and energy characteristics of the laser which will be produced by automatically controlling the actuators in the system when the physician starts the procedure.

FIGS. 10A to 10D illustrate various aspects of focusing the laser within the context of a laser guide 400. In accordance with many embodiments, the laser shaper may include the telescope subsystem 480 as mentioned above. The telescope 480 may include various modules of lenses such as a scan module 410 and a focus module 430, as shown in FIGS. 10B and 10C. The last optical group in the system which brings a roughly parallel beam to a focus is referred to as the objective module 450 (or an objective lens assembly). Herein, the term objective is used to specify the final optical group of the delivery system. In order to not lose laser energy due to clipping loss as the beam is scanned, the beam expander is required to have an entrance pupil located at or near the galvo mirrors and an exit pupil at or near the entrance to the objective.

Due to fundamental optics, any telescope having externally located entrance and exit pupils on opposite sides of the telescope must then contain an intermediate focal plane. In such embodiments, the optical design of the laser delivery system will therefore contain two focal planes, and a total of three optical groups which each take roughly parallel light to a focal point, or vice versa. The parallel laser light scanned by the galvos 405 (shown for 3 different positions in FIG. 10C) is brought to a focus by the first optical group which is termed the scan module 410 (consisting of two (2) lens elements 411 and 412 in this example), then that focus is reverted to roughly parallel light by the second optical group which is termed the focus module 430 (consisting of two (2) lens elements 433 and 434, in this example), and this parallel light is brought to a final focus by the objective (i.e., the third group) 450, indicated in FIG. 10A. The focus and scan modules together constitute a beam expander in the form of telescope 480 because in combination the input and output of telescope 480 are both collimated or nearly collimated.

In some embodiments, focusing the laser may include, in particular, examples of infinity correction and lack of infinity correction as illustrated in FIG. 10A. A common practice in the optical design of systems with a number of modules is to design each module to be infinity corrected, which means essentially that each module can operate by itself with a point source or collimated light. In the case of a laser delivery system (LDS) used in an ophthalmic surgery laser system (e.g., laser guide 400) there may be 3 modules between laser input and the output target plane (the target plane being understood as the plane normal to laser beam 50 at focus 51 of FIG. 9), thus there are 2 fundamental intermediate regions, the first between the scan and focus modules 410 and 430 respectively, and the second between the focus and objective modules.

As shown, the intermediate space #1 (shown in FIG. 10A) may contain a focal plane 220 (shown in FIG. 10B) represented by a dashed line (see also, intermediate focus 52 of FIG. 9). So, in the case that the scan module is infinity corrected, this focus may be of high quality, as schematically illustrated in FIG. 10A. Likewise, in the case that the scan module is not infinity corrected, the intermediate space #1 focus may be aberrated, as schematically illustrated in FIG. 10A.

In some embodiments, as illustrated in FIG. 10A, the intermediate space #2 may be approximately collimated, and does not contain a focus. In the case that the scan and focus modules are infinity corrected, the light rays in the intermediate space #2 may have paths that can be extended to a virtual focal plane or a virtual focal point. Such point may located at some distance where the beams will meet at a well-defined point, as illustrated in FIG. 10A. In other words, the light rays in intermediate space #2 may have a point source in the case of using infinity corrected modules. A beam of light having a point source can be focused to a (diffraction limited) point when it is passed through an ideal paraxial lens. In contrast, in the case that the focus module is not infinity corrected, the light rays will have paths that are mixed up so that there is no location where the rays meet at a point, as illustrated in FIG. 10A. In other words, the light rays in intermediate space #2 have an extended source in the case that the focus module is not infinity corrected. The quality of having light with an extended source means that such light will not focus to a diffraction-limited spot when focused by a perfect lens.

In some embodiments where the objective module 450 is infinity corrected, a tight focus may be produced over the scanning region when light with a point source (i.e., an ordinary laser beam with possible convergence or divergence but no higher order aberrations) is input into the objective. In some embodiments, the objective module 450 is not infinity corrected. When the objective is not infinity corrected, then the scan and focus modules are required to process the light with a certain balance of aberrations before it enters the objective in order to obtain a high quality focus at the target. In any system where the desired output is a good quality laser focal spot, the system as a whole would preferably be infinity corrected so that a standard laser beam will form a high quality focus in the target region.

In traditional laser delivery systems (LDS), an optical design is developed which could potentially produce a high quality image, and in addition the individual modules are traditionally designed to be infinity corrected. It is true that infinity corrected modules have some advantages, chief among them that they are relatively easy to optically test individually without using specialized equipment such as custom made null lenses. However, by requiring the modules to each be infinity corrected, the complexity of the system and the cost to produce is thereby increased.

In accordance with some embodiments, some modules may not be infinity corrected, therefore, complexity of testing and qualifying the individual modules will generally be more difficult than for testing infinity corrected modules. Although the testing is more complex, it need only be implemented a minimal number of times in order to incorporate it on a large-scale production. This is because the testing usually is capable of producing a better product for production from minimal tests because the completed tests typically determines any flaws that should be adjusted for in the final product. For example, only one testing and qualifying may be sufficient to qualify a production facility to produce larger quantities. Additionally, there are alternatives to null lens testing such as directly measuring the fabrication errors of the completed module to show that it meets the design specifications. Beneficially, it can be more cost effective to manufacture production quantities of simplified design modules, which are not infinity corrected, despite the greater difficulty of the module testing process.

In accordance with many embodiments, the scanning module 410 and the focus module 430 may be made up of a variety of lenses that are configured to further guide the incoming beam such that then final output is as desired. As previously noted, as shown in FIG. 10B, in one embodiment, the scan module 410 may include two lens elements 411 and 412 and the focus module 430 may include two lens elements 433 and 434. FIG. 10B also illustrates multiple positions 431, 432 of focus module 430, showing its Z control function. More specifically, at position 431, the focus module 430 is in a deep Z focus position, whereas at position 432, the focus module 430 in a shallow Z focus position. Furthermore, as illustrated in FIGS. 10B and 10C, many embodiments may include a plurality of galvo mirrors 405 to redirect the incoming laser into the scanning module 410 and subsequently into the focusing module 430. Respectively, the positioning of the galvo mirrors 405 can affect or ultimately determine the X and Y positions of the intermediate focus 220 illustrated by the dashed line plane in FIGS. 10B and 10C. FIG. 10C illustrates multiple positions of galvo mirrors 405 in order to illustrate this XY control function. In many embodiments, the intermediate focus 220 is required by fundamental optics to be located between the scanning module 410 and the focus module 430. Additionally, the propagation angle of the output beam or beam that leaves the focus module may also be determined by the position of the galvo mirrors. In other words the positioning of the galvo mirrors within laser guide 400 will have a downstream effect on the position of the final focal point in the eye tissue 10. Thus, altering the position of the galvo mirrors 405 may allow for the change in position of the final focal spot in the eye 10. FIG. 10D is an illustrative view of how the positioning of the various galvo mirrors 405 can redirect the laser beam.

Figure 11:
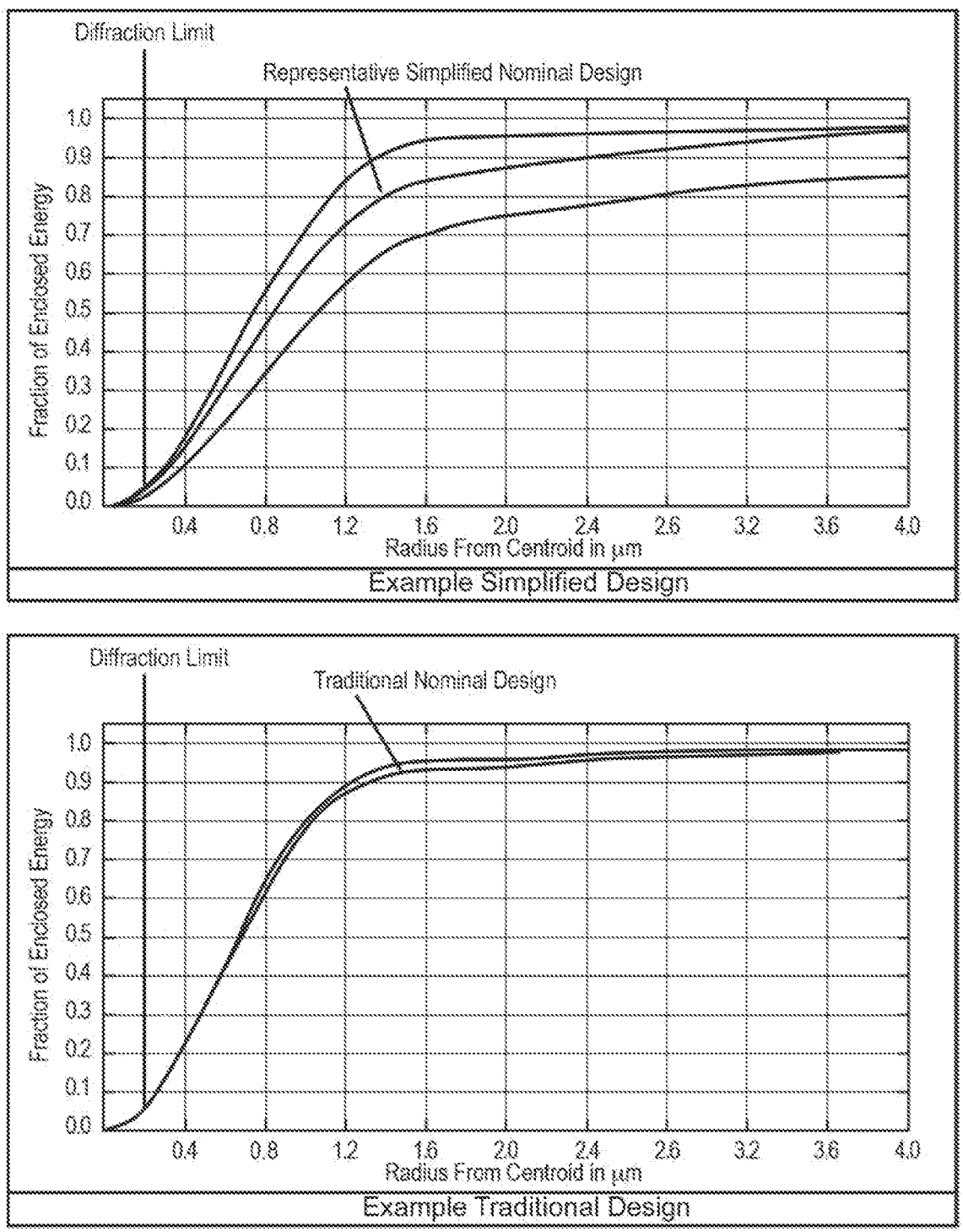
FIG. 11 is a graphical illustration of the relation of encircled energy to radius to form a focal spot, in accordance with an embodiment and compared to a traditional optical design for an ophthalmic laser delivery system.

FIG. 11 illustrates another embodiment of focusing the laser by way of a graphical comparison between RMS wavefront & encircled energy optimization. Optical design methods have evolved in general to produce high quality imaging systems which can for example provide appealing images as judged by the human eye, or fabricate the smallest computer chip features in the case of photolithography. In accordance with many embodiments, aspects of the system and method are directed to a laser delivery system for an ophthalmic surgery laser system. In particular, the laser delivery system may be designed using encircled energy as its primary function rather than RMS wavefront error. Encircled energy refers to the measure of concentration of energy with respect to an optical image over a range of radial distance from the center point, i.e., within a circle of radius R, some fraction of the total energy will be contained. The radius containing 80 percent of the energy is called R80, the radius containing 60 percent is called R60 and so forth. There are different encircled energy radii Rxx in any particular case depending on the choice of fractional contained energy, however R80 and R60 are typical choices for describing LDS performance. Encircled energy may be used as a measurement to determine the spreading of a laser projected over a given range. In some embodiments, the encircled energy may be used as the primary design criterion due to the limited need for high contrast optical images in the case of laser delivery systems. Additionally, the laser delivery system may be designed such that the modules do not need to be infinity corrected. Such uncorrected systems may be a type of laser delivery system, which is substantially simplified and more economical to produce compared to the current practice. In many cases, a simplified design will employ a much lower total number of lens elements and the lens elements will have shapes that are easier to fabricate, compared to a traditional design.

Conventionally, a laser delivery system (LDS) design is optimized to minimize the RMS wavefront error, referred to here as simply the RMS, by following the traditional approach to optical imaging system design. In the case of an LDS, the traditional approach may result in producing a design with more capabilities than are actually needed for the application. In the case of an imaging system, when the aberrations cause some of the light to fall outside of the central spot, minimizing the distance by which the residual light misses the central spot is important for the image quality (e.g., the contrast or sharpness of the image). However, there is an important difference between the requirements for a laser delivery system (LDS) and an imaging system. In both cases, we may consider that a laser beam must be focused to a small spot, which is near in size to the diffraction limit. However, in consideration of the small fraction of light that passes outside the central focal region, an LDS is more forgiving than an imaging system. The encircled energy characteristic is a good way to measure the main concentration of energy at the focus while disregarding all the energy that is outside the encircled energy radius. The RMS criterion accounts for nearly 100% of the energy and cannot disregard the energy outside of the main focal spot. A laser delivery system, in accordance with many embodiments, is not used as a traditional imaging system and does not require the precise resolution that would be required in an imaging system, thereby reducing the complexity and cost necessary to produce and use such systems.

Mathematically, the RMS is a good way to account for the distance by which the residual light misses the central spot. However, in the case of an LDS, which is designed to perform material processing with nonlinear laser-induced effects, such as plasma generation for example, in which case the concern is only for how much of the beam is directed into the plasma region formed by the central spot. When the residual light misses the lateral range of the plasma region, it does not matter if the light misses by a small distance or a large distance. Whereas in an imaging system, the greater the distance by which the residual light misses the central focal spot, then the greater will be the loss of contrast in the resulting image, which is well described by the RMS criterion.

In accordance with an embodiment, an ophthalmic surgery laser system may be configured such that the quality of a laser beam focus is determined based on the percentage of energy contained in the main focal spot, rather than its focal tightness in consideration of the full extent of the beam energy. In some embodiments, the system may be configured from the measured graph of the encircled energy as a function of radius as illustrated in FIG. 11. This is the fraction of energy contained within a disk in the focal plane of the laser. For example, using the ISO recommended definition of beam size or diameter (D), which extends D (4 sigma) beyond the main focal spot to account for essentially 100% of the energy, here, the laser energy may be concentrated at the central point of the focus for purposes of generating a laser plasma where the encircled energy radius contains most of the energy but is significantly less than all of the energy, such as a range of 60-80% of the total beam energy. Also for example, the laser energy may be concentrated where the encircled energy radius contains sufficient beam energy for cutting independent of its focal tightness or the extent of the light falling outside this radius.

Due to diffraction of light, there is a basic limit of how tightly the beam can be concentrated at a focus, this represents the theoretical case of perfect optics, and the encircled energy curve for the diffraction limit is often placed on the graph for comparison with the results of using realistic optical components. FIG. 11 illustrates an upper graph with three curves showing aspects of the simplified design method, including the diffraction limit (illustrative of perfect optics); and a curve illustrating the simplified nominal design using non-infinity corrected modules with the encircled energy criterion. In many embodiments, the simplified method as illustrated in the upper graph of FIG. 11 shows the encircled energy may closely approach and/or substantially match the ideal (diffraction limit) between 60% and 80%, which may be sufficient to couple the laser energy efficiently into the plasma generation at the focal point. The lowest curve in the upper graph indicates an exemplary approximate cutting limit that is less than the nominal design. A lower graph in FIG. 11 shows a representative traditional nominal design for comparison, including a curve reflective of a standard / traditional imaging design using the RMS criterion. In a traditional design the RMS wavefront of the nominal design will be quite low. The encircled energy will be very close to the diffraction limit in a traditional design, for example, the lower graph indicates the diffraction limited 90% energy radius is approximately 1.2 microns while the traditional nominal design 90% energy radius is approximately 1.3 microns. In the upper graph, for example, the 90% energy radius for the diffraction limit is indicated as about 1.35 microns, while the simplified nominal design in this example has a 90% energy radius of about 2.4 microns. However, at a lower encircled energy level, such as 70%, the simplified design diffraction limit is about 1.0 micron while the simplified nominal design is about 1.15 microns.

Producing adequate results with femtosecond laser cutting commonly requires a low plasma generation energy threshold, such as 0.3 uJ, with a small spot size such as 2 µm transverse diameter. The uniformity of the spot size as a function of the X,Y position is often of greater importance than achieving the lowest possible value of the cutting threshold. In a typical LDS designed as an imaging system the uniformity is maintained by making the performance of the system rigorously diffraction limited. Thus, such imaging systems involve complex optical designs in order to have such a high degree of correction (i.e., lack of aberrations). According to many embodiments, the simplified design allows a moderately larger spot size such as 2.4 microns and does not require the rigorous diffraction limiting function of imaging systems.

The simplified method, according to various embodiments, allows the energy outside of the encircled radius to spread out to relatively greater distances from the focus center. The spreading out from the focal center is traditionally undesirable in conventional optics systems because they function as an imaging system, which requires a higher resolution. For example, in the standard design method using RMS optimization, the remaining 20% is relatively tightly controlled, represented by the curve, which is close to the ideal curve all the way up to 100%. The RMS design is expected to have better performance for producing an image, but essentially the same performance as the simplified design for laser cutting. Here, by removing (or at least relaxing) the constraint to control the last 20% of the encircled energy, a simplified configuration can be advantageously implemented, which is more cost effective to produce than the standard design, which seeks to control 100% of the energy. Another way to describe the difference of a simplified design LDS is that it will have a greater content of high order aberrations than would a corresponding imaging system design. The higher order aberrations by definition produce a steeper error than the lower order aberrations at the margins of the pupil, and this aspect becomes more permissible when applying the encircled energy criterion to the design process.

FIG. 12 schematically illustrates an exemplary laser delivery system (LDS) of the ophthalmic surgery laser system of FIG. 9, in accordance with an embodiment. In accordance with an embodiment, the LDS is represented as laser guide 400 in FIG. 9. As discussed above, the laser guide 400 may include a plurality of modules including a scan module 410, a focus module 430 and an objective module 450; as illustrated in FIGS. 10A and 12. In FIG. 12, some embodiments of the laser guide 400 may be configured such that the intermediate focus 52 falls between the glass elements of scan module 410 and the focus module 430, to prevent damage to the glass from the intermediate laser focus. Additionally, in some embodiments, the laser guide 400 may be configured such that a beam splitter 535 falls optically between the focus module 430 and the objective module 450.

In accordance with an embodiment, the scanning module 410, the focus module 430, and the objective module 450 each include a number of lenses (including each having multiple lenses) configured to guide various infrared and visible respective beams which are deployed (from the guide or light source). In one embodiment, the scanning module, the focus module, and the objective module contain a much lower total number of individual glass lens elements than a traditional ophthalmic laser delivery system, such as 10 elements compared to 20 elements.

As previously discussed, and in accordance with various embodiments, the laser delivery system may be designed with complexity reducing elements such as the encircled energy criterion and non-infinity corrected lens modules, thereby simplifying and reducing the cost of the overall system. Other embodiments, such as illustrated in FIG. 12, may further simplify the system by using more simple lens forms, since these will be easier to fabricate. Simplicity in this sense means lens surfaces with relatively low curvature and lens edges with convenient thicknesses for manufacturing, such as a thickness-to-diameter aspect ratio around 1:6. In some embodiments, the lenses used may be plano-convex singlet lenses. Plano-convex lenses are positive focal length lenses with a convex portion and a flat portion, they are the easiest of all lens forms to fabricate and are therefore ideal for reducing cost of an overall laser delivery system. This is due to the relaxed design constraints with the use of encircled energy in many embodiments that make it more feasible to simplify the form of the lens elements in the design, as well as reducing the total number of lens elements required to implement the design in comparison to a traditional approach. In an embodiment, the scanning module 410, the focus module 430, and the objective module 450 have lenses wherein a majority of which are simple plano convex lens. The embodiment illustrated in FIG. 12 represents a majority of lenses (e.g., in this example, five (5) out of nine (9)) within the laser deliver system as being plano-convex, which is generally the easiest lens form to fabricate.

In another embodiment, the objective module 450 may contain a single plano-concave lens element and the others are plano convex lens elements.

Some embodiments, similar to the LDS shown in FIG. 12, may include one or more meniscus lenses. Meniscus lenses are those that have a convex and a concave surface. From a simplicity standpoint, the meniscus form is generally less desirable for manufacturing, but it has been found to be particularly valuable for system performance when placed at various positions within the delivery system. In some embodiments, placing a meniscus lens at the input position for the focus module 430 (lens element designated 433), may be helpful to increase the diameter of the usable scan region at the deeper scan positions of the target region. In one embodiment, the laser delivery system may have at least one strongly curved meniscus lens with radii of curvature close to the clear aperture diameters, in addition to being placed at an input position for the focus module. Due to these advantages, many such embodiments may include the use of a larger and thicker meniscus lens, despite the increased fabrication difficulty of this lens form.

In accordance with an embodiment, the laser guide 400 may be configured using its encircled energy diameter as its figure of merit. In particular, the LDS may be configured to have an 80% encircled energy diameter (D80). A small D80, such as 2 microns, will assure that the laser beam is able to efficiently pump energy into the plasma region, but it does not try to control the light which misses the central spot. This essentially means the LDS optical design has less work to do and therefore it can be simplified relative to an imaging system design. Accordingly, many embodiments may allow for the number of individual lenses may be reduced by a substantial amount such as half-compared to a standard design, and the shape of the lenses can be simplified with a high proportion of planar surfaces and relatively mild curvatures. According to one embodiment, the scan module 410 may be limited to two lenses. Similarly, the focus module 430 may also be limited to two lenses. Likewise, the objective module 450 may be limited to four lenses. This arrangement may be useful for regenerative femtosecond laser amplifier systems with a bandwidth in the range of 3 nm, however other laser sources such as fiber laser amplifiers may be of interest with even shorter pulses and correspondingly higher bandwidths such as 10 nm. In another embodiment, the objective module 450 may be limited to five lenses.

A relatively simple change to the objective design consists of changing the plano-concave lens E3 into a doublet, and this is able to significantly increase the range of acceptable femtosecond laser bandwidth, which can be accommodated by the LDS. The doublet is mechanically still a single piece of glass to be mounted, so the increased complexity of using a doublet relative to the singlet is confined to the glass fabrication process rather than the system integration of the LDS.

Advantageously, many embodiments of the laser delivery system described herein may provide for a low-mass movable module assembly (focus module 430) by reducing the number of lenses used. This can enable the high-speed operation of the focus module Z control, which can allow greater flexibility to customize parameters within a scan due to a higher maximum scanning speed associated with the lower mass. Additional benefits may include lower cost to produce the optical elements for the LDS and/or lower cost and shorter manufacturing time to assemble the LDS.

The moving mass is significant, consisting of the focus module 430 itself and the moving portion of the linear motor stage (e.g., stage 570, discussed below), which drives the motion. When the focus module is moved with high acceleration, a substantial reaction force is applied to the delivery system, which creates vibrations, and mechanical instability, which will be transmitted to the patient interface while the treatment pattern is being run. The quality of the treatment depends on stability of the eye position relative to the delivery system, and the limiting acceleration for focus control can be due to the need to avoid creating excessive vibrations in the delivery system, even though the linear motor is capable of operating at considerably higher levels of acceleration. A fast treatment time is not only more comfortable for the lightly sedated patient, but also lessens the chances of inadvertent patient movement affecting the pattern accuracy.

Figure 13A:
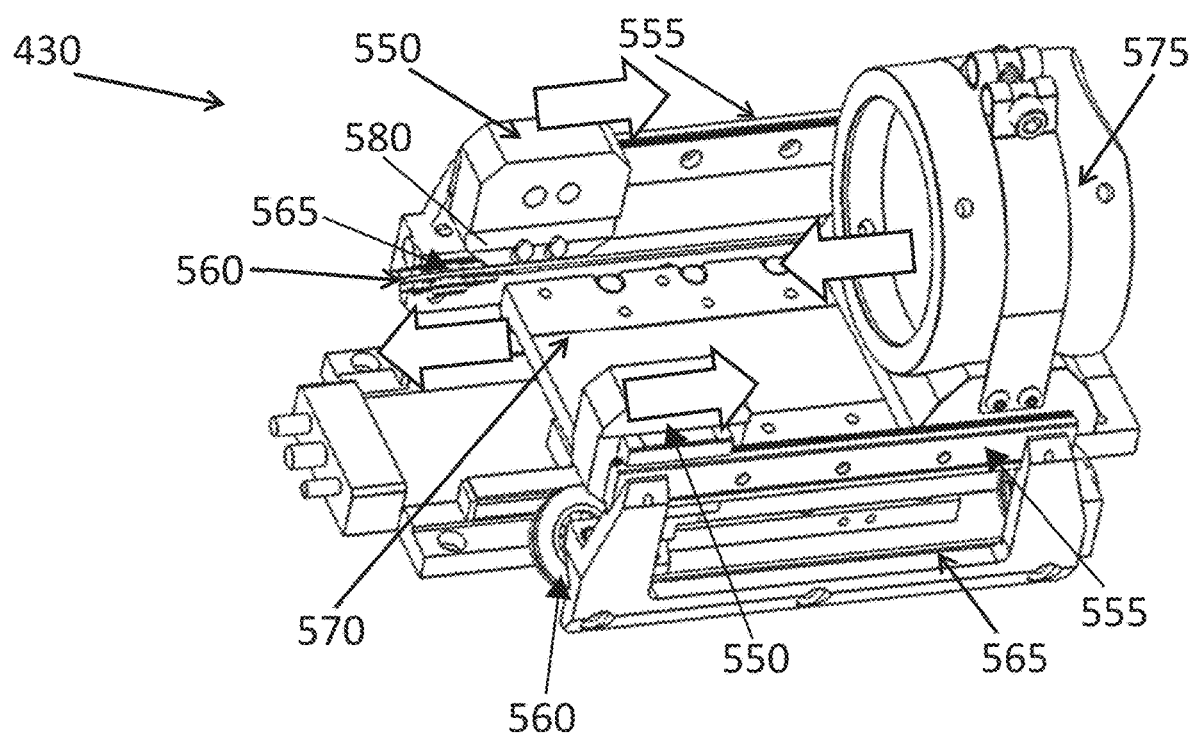
FIGS. 13A-13C illustrate a counterbalance system, in accordance with an embodiment.
Figure 13B:
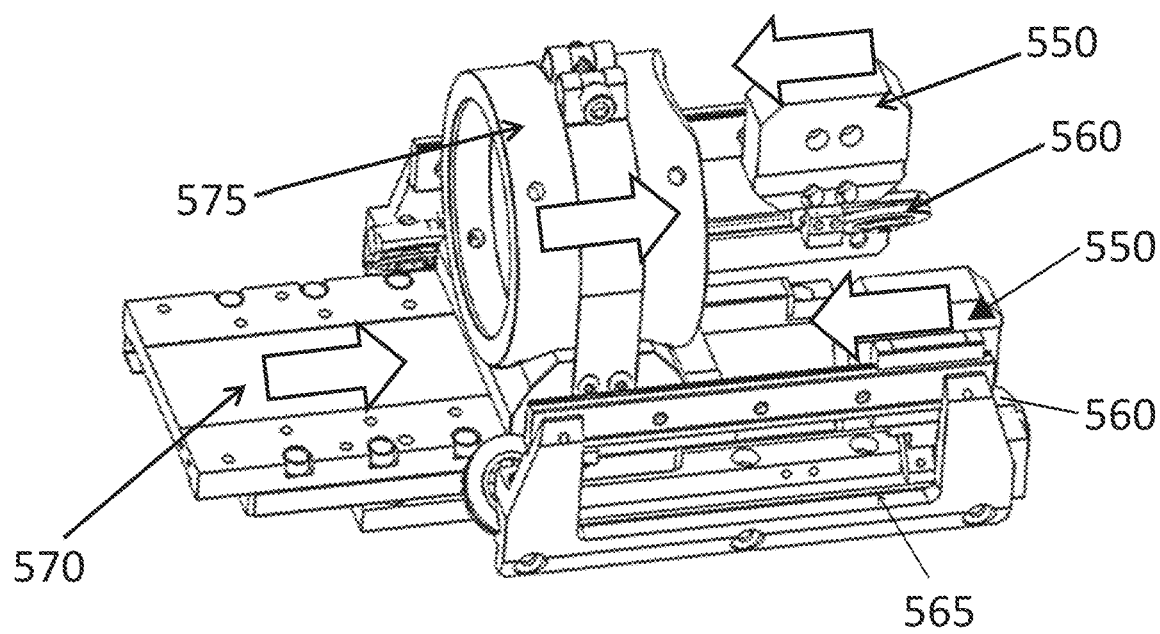
Figure 13C:
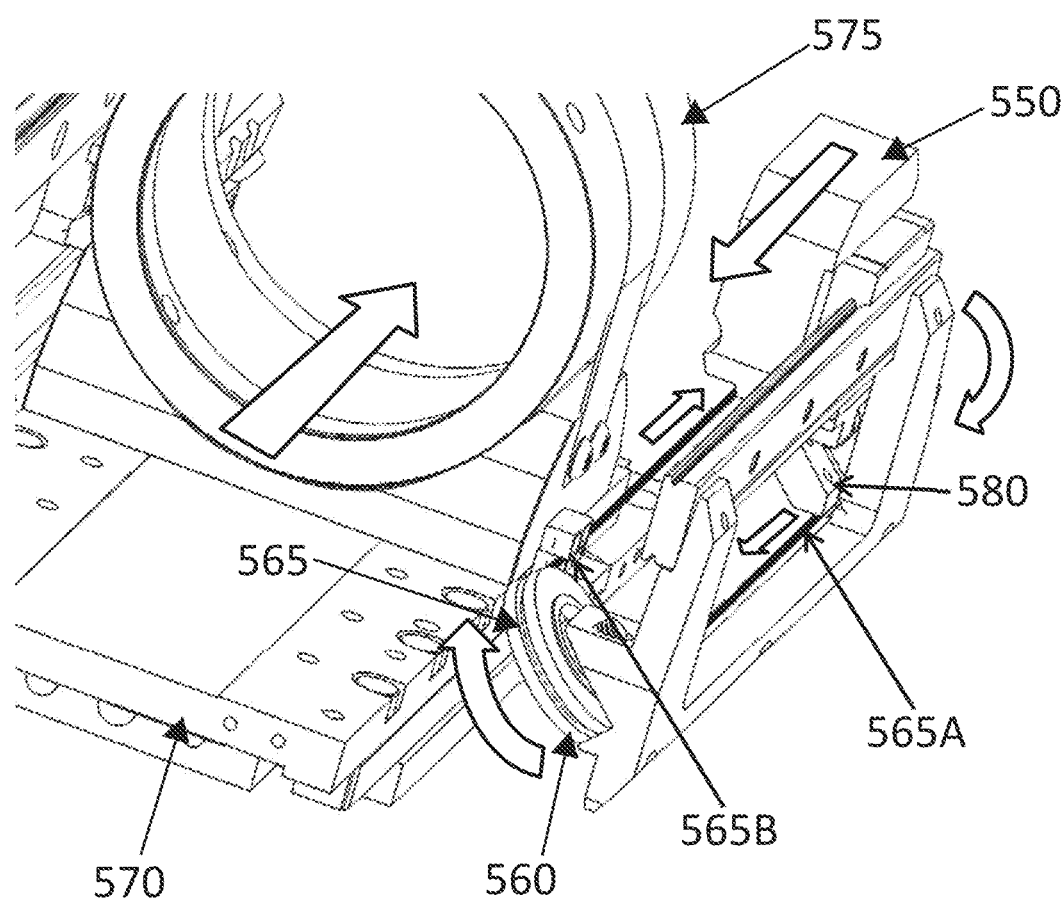

Referring to FIGS. 13A to 13C, shown are parts of a counterbalance system that is part of focus module 430, in accordance with embodiments herein. The counterbalance system is configured to maintain stability of the laser delivery system such that the focal point is controlled within the target space. Various embodiments of the movable lens may include a set of pulleys 560 and steel wire loops 565 (or cables) connected to the focus module stage 570 at connection points 565A, 565B (shown in FIG. 13C) as part of the counterbalance system, so that a pair of weights 550 are moved in the opposite direction of the moving focus module 575. Each of the weights 550 may be provided on an arm 580 (see FIG. 13C) and configured to move along a corresponding track or linear rail 555 (i.e., rails 555 and weights 550 are on either side of stage 570). This arm and rail arrangement assists in minimizing any additional width imposed by adding the counterweight assemblies to the focus module 430. Further, here, as an example, the focus module stage 570 is shown in the form of a platform relatively positioned in front of the focus module 575 (along the X-axis). Arrows in FIGS. 13A-13C indicate possible movement or motion of the noted features. FIGS. 13A and 13B illustrate the focus module 575 position changing from a first position to a second position, respectively, i.e., the right hand limit of travel (FIG. 13A) to the left hand limit of travel (FIG. 13B), due to the action of the linear motorized stage 570. Of course, it should also be understood that the stage 570 and the focus module 575 are also configured for movement and/or placement between the two (first and second, or right and left) positions. Cables or wire loops 565 are looped around the pulleys 560 to impart motion and an equal travel in the opposite direction upon the counterweights for any movement of the focus module 575. The pair of weights 550 may be designed so that their total mass is equal to the moving mass of the focus module 575 plus the linear motor stage platform 570, thus there will be no net linear momentum change when the focus module is accelerated in either direction, i.e., equal weights are moving equal distances in opposite directions. By using a pair of weights 550, it is further possible to place the center of mass of the counterweights on the same axis as the center of mass of the focus module 575 and stage platform 570. In this case there is zero moment arm between the centers of mass moving in opposite directions and therefore no rotational torque will be applied to frame of the delivery system when the masses are accelerated. When the centers of mass of the counterweight assembly and the focus module assembly are co-axial, both linear and rotational reaction forces are cancelled out.

In accordance with some embodiments, adding a balanced counterweight to the Z focus module 430A and drive may permit high acceleration patterns to be run up to the force limit of the linear motor. Such applications may not be readily recognizable as advantageous, because the motor is driving twice as much mass with the counterweight installed. Thus, the mechanical maximum acceleration possible is equal to half of the maximum acceleration in the case of driving only the focus module, which may allow reaction forces to affect the delivery system. However, the maximum acceleration limit for a non-counterweight system may be much smaller than the mechanical limit of the motor, for example 10%, because of the need to limit vibrations below a significant level at the patient interface. If the counterweight permits operation at 50% of the possible acceleration of a non-counterweight system, then for example a 5× increase in available acceleration may be obtained by adding the counterweight, with no additional complexity in the control system. Thus, the counterweight system may aid in increasing the acceleration of the laser focus control function without compromising the stability of the patient interface. The full 100% acceleration of a non-counterweight system could be obtained by adding an additional linear motor to drive the counterweights but this would also substantially increase the control system complexity, leading to higher production cost and potentially a negative impact upon reliability.

In accordance with various embodiments, the moving weights 550 may be manufactured from a very dense material such as a machinable tungsten alloy. Such dense materials can help to limit the volume increase associated with adding the counter mass assembly. In other embodiments, the pulley wheels 560 can be mounted at various angles. For example, in some embodiments, mounting the pulley wheels 560 at 45 degrees to the plane of the focus module linear motion stage 570, such as illustrated by the rear pulleys 560 in FIG. 13B, may allow the upper cable section to be nearly coincident with the motor stage, thus simplifying the attachment mechanism from cable to stage. Other embodiments may allow the lower cable segment to be accessible to the moving weight by a compact arm coming down from the moving weight 550, this arm structure is located at the tip of the arrow indicating 565A in FIG. 13C. In accordance with some embodiments, the steel wire loops 565 may have several attachment points 565A and 565B to the support structure and the moving lens respectively as illustrated in FIG. 13C. Such arrangement may allow for the counter weight to easily move thereby incorporating the high speed movement in a manner consistent with precision operation.

Figure 14A:
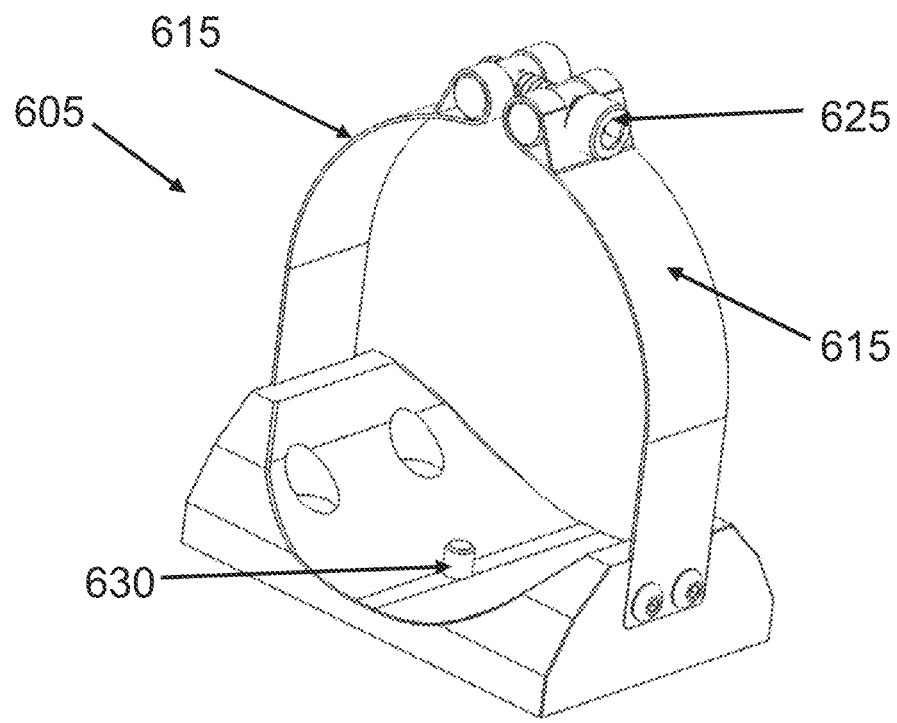
FIGS. 14A and 14B illustrate an economical high precision mechanism for supporting a lens module, in accordance with an embodiment.
Figure 14B:
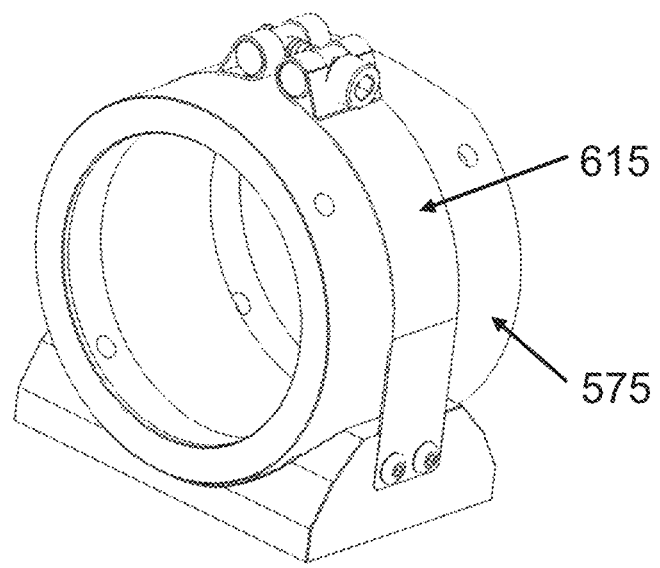

Turning now to FIGS. 14A and 14B, many embodiments may include a support structure 605 for the moving lens 575. Many embodiments may include a set of straps 615 configured to wrap around an outer periphery of a housing of the moving lens 575 and secure it in place on the stage platform 570, such as shown in FIG. 14B. The straps may have a first end that is secured (e.g., fastened or bolted) to a frame portion of the stage platform 570, in an embodiment. In some embodiments, the straps 615 may have second ends that are secured via a closure mechanism 625. In one embodiment, the closure mechanism 625 may be similar to a hose clamp closure. In FIG. 14A, for example, the closure mechanism 625 is provided at a midpoint or top of the lens 575. In other words, the support structure 605 may have two straps 615 that are connected at ends thereof via closure mechanism 625 that can be tightened such that the straps 615 cinch around the moving lens 575 and secure it in place on the stage platform 570 for movement by a linear motor actuator or linear drive system. Of course, other mechanical mechanisms and/or fasteners may be provided for closure mechanism 625. Moreover, in another embodiment, a single strap 615 and closure mechanism 625 may be used. Further, the location of the closure mechanism 625 is not intended to be limiting.

In some embodiments, the support structure may have a key 630 (shown in FIG. 14A) that engages with the moving lens 575 to align the moving lens 575 appropriately within the support structure 605.

While this mounting method is optimized with low mass for mounting the moving lens module, it is also suitable for mounting a fixed position module such as the focus module.

The capabilities of a laser delivery system in accordance with many embodiments may be enhanced with the addition of controllable alteration of the laser beam characteristics of beam size and clip level as the first step in processing the beam out of the laser. In accordance with various embodiments, these functions may be contained in the beam shaping module 300. In some embodiments these functions may be performed by a secondary beam expander known as a variable laser beam expander. The beam diameter D may be controlled with a variable magnification laser beam expander, while the clip level may be controlled with a variable diameter iris. The beam size is mainly determining the Numerical Aperture (NA) of the focused output spot due to the approximate relationship $NA=n*D/2f$, where n is refractive index and f is the focal length. At a higher NA, the laser spot may be smaller based on the diffraction limit of light. However, at higher NA values it may be easier to disrupt the focus with optical imperfections which may occur in the ocular tissue, in the case of various pathologies, as well as imperfections in the delivery system optical path. It is a typical concern in optical systems to find the best value for NA which balances diffraction effects (which are better with large beam size D) against geometric aberrations (which are better with small beam size D), in order to maximize performance in various applications. However, the best NA value for an ophthalmic surgery laser may depend on tissue conditions which vary from case to case. Also the optical imperfections present in the laser delivery system may sometimes be effectively accommodated by changing the NA, between and/or within procedures, depending on the details of the procedure to be performed and the nature of the case at hand. Accordingly, it will generally be an advantage to control the NA with selectable values between procedures, as well as changing NA value during procedures.

Accordingly, many embodiments may incorporate a variable laser beam expander which is compact and simple to control. The standard design for a laser beam expander requires 2 different lens groups to be moved separately, such that one group moves to vary the magnification and the other group moves in order to maintain collimation of the output. The use of 2 separate position actuators to control magnification results in higher cost and complexity than for a single actuator, so that real-time variable NA has been rarely, if ever, implemented in femtosecond ophthalmic lasers. Thus many embodiments may improve upon the standard designs by incorporating a single actuator to control magnification over a wide range without significantly affecting collimation of the output which is not typical for such systems.

Figure 15:
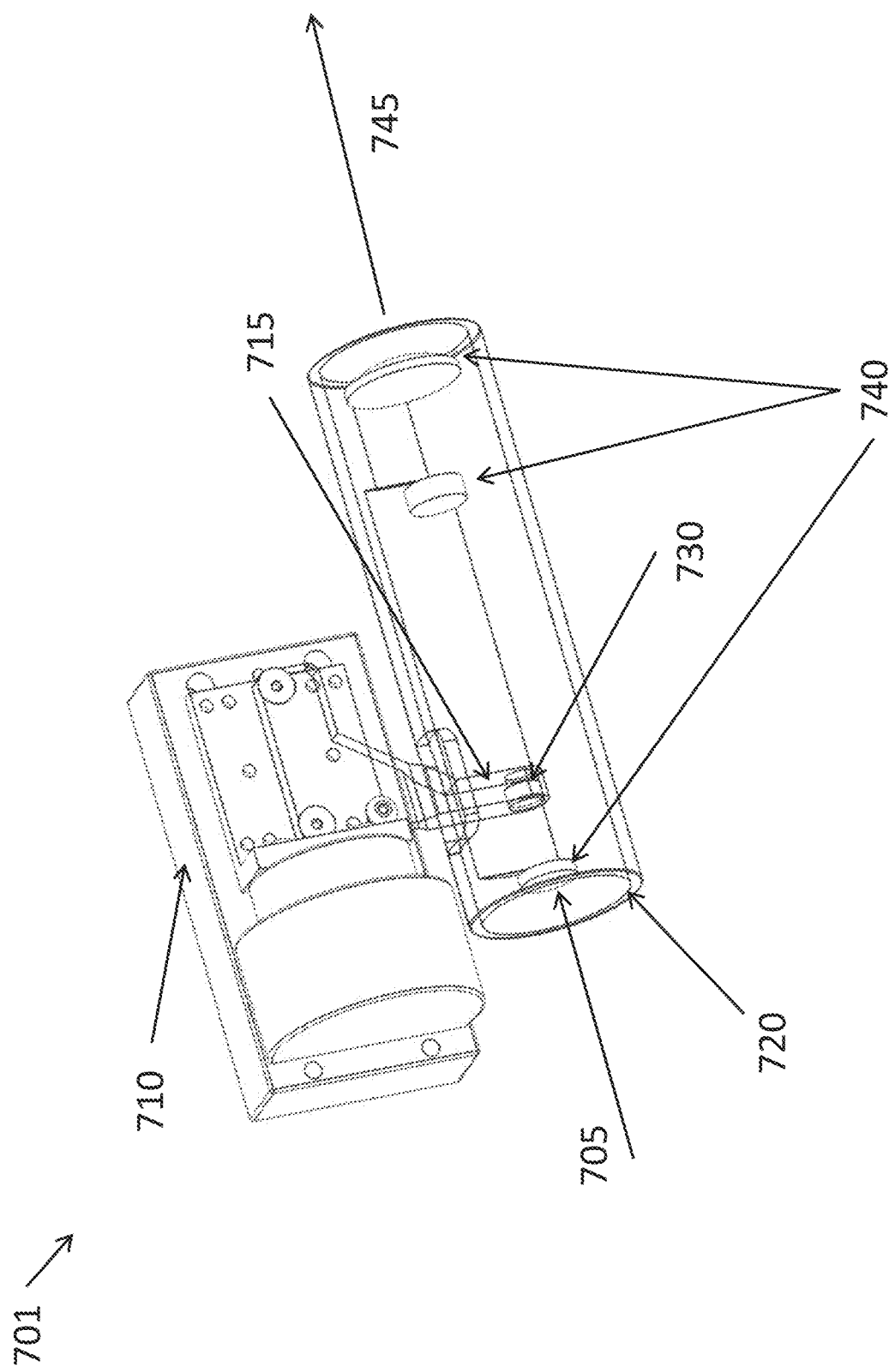
FIG. 15 illustrates a Variable Laser Beam Expander (VLBE), in accordance with an embodiment.

Referring now to FIG. 15, an embodiment of a variable laser beam expander (VLBE) 701, for the beam shaper, having a single moving element is illustrated. This VLBE may be self-compensating during operation. In accordance with many embodiments, the moving element may be a moving lens 730 that is contained within a lens housing 720 and mechanically connected to a linear drive system 710. The lens housing 720 may include a plurality of fixed lenses 740 supported by lens mounts (not shown for clarity). The lens housing 720 may further be configured with an optical input 705 and an optical output 745. In accordance with many embodiments, the linear drive 710 may be designed to connect to lens 730 that may be movable within the lens housing 720. The movement of the lens 730 within the housing 720 may also be controllable via suitable control systems that can dictate the movement and relative position of the moving lens 730 within the housing 720 of the variable laser beam expander 701.

Figure 16B:
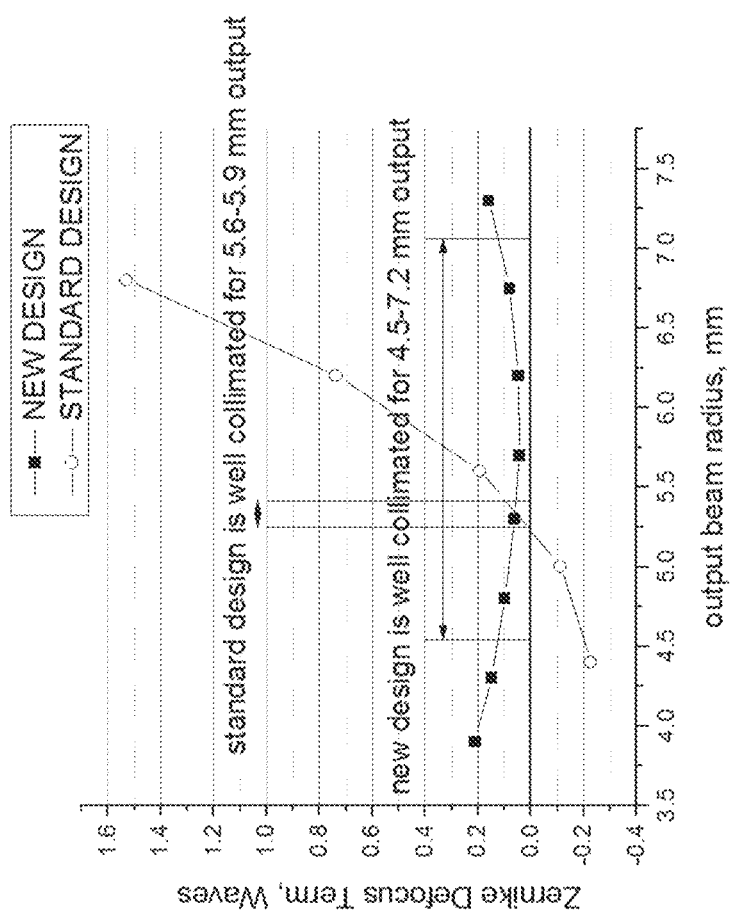
FIGS. 16A and 16B illustrate a comparison between standard VLBE designs and embodiments of this disclosure.
Figure 16A:
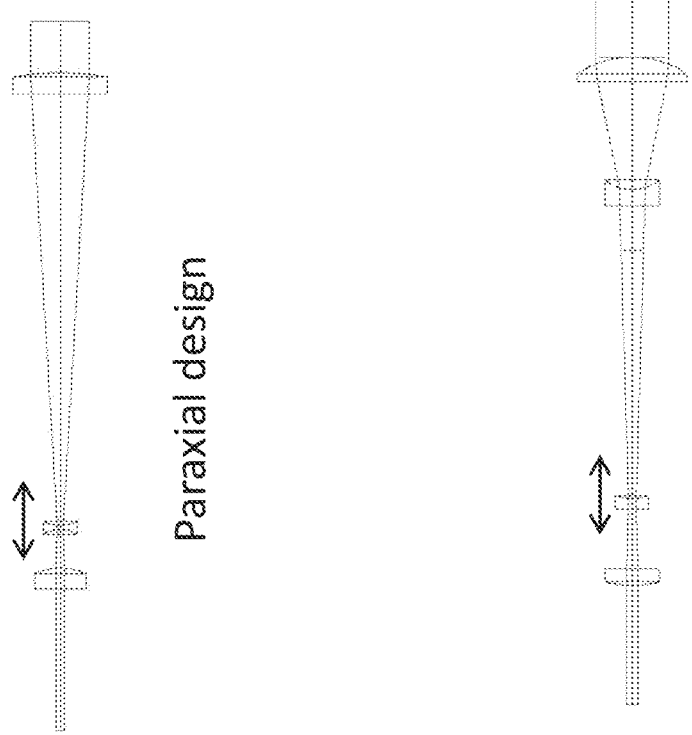

The technique for designing a single moving element variable laser beam expander according to many embodiments can be illustrated by graphing the defocus as a function of magnification as illustrated in FIGS. 16A and 16B. FIG. 16B illustrates a comparison curve between a standard design and the disclosed (new) design according to an embodiment with a single moving element. FIG. 16A illustrates the differences between a self-compensated and paraxial design of a VLBE according to embodiments of this disclosure. It is generally accepted in the optics industry that a variable beam expander must incorporate two separate axial lens motions to have variable expansion while maintaining the state of output collimation, i.e., a defocus term of zero.

A common way to measure the defocus for developing graph similar to FIG. 16B is to find the value of the Z4 Zernike Defocus term obtained when the output wavefront is fitted to Zernike polynomials in the usual way. The Z4 term is also called the Defocus term and it measures the spherical shape component of the wavefront. The Z4 term is zero for perfect collimation, and it can assume positive or negative values for an output that is converging or diverging. Also, if the Z4 term is not zero but still quite small, then the output may effectively be called collimated. A common practical estimate for "quite small" in terms of wavefront deformation is 1/10 wave peak to valley, so on that basis a criterion of Z4<0.1 is reasonable for the output of a CVLBE to be termed collimated. In FIG. 16A an example is shown for a typical CVLBE designed using paraxial optics calculations. In the defocus graph, the standard design shows a Z4 value going from negative to positive with a fairly steep slope as a function of magnification, or equivalently, as a function of output beam size. In this example, the standard design is effectively collimated for a beam size range of 5.6-5.9 mm, or an adjustment range of 5% which is generally too small to be of practical use. To obtain a useful adjustment range from a paraxial design VLBE, the standard practice is to separately move a second lens in order to compensate the focus changes caused by changing the magnification. Due to the added control system complexity, a paraxial design VLBE is seldom implemented in a surgical laser system.

The quadratic shape of the Z4 vs magnification curve seen in FIG. 16B is important in designing a self-compensated VLBE according to many embodiments. As a result it is possible to design a device such that over the operating range, the Z4 curve is a parabola nearly tangent to the X axis, thus maintaining a low value over a relatively wide range of magnification. In the defocus curve, the disclosed design maintains Z4 within a range of 0.1 for an output beam size range of 4.5 to 7.2 mm, an adjustment range of 2.7 mm or about 45% adjustment range. This wide range is adequate for optimizing many laser based applications, such as surgical laser delivery systems, while offering a simple implementation for the control system.

Figure 17A:
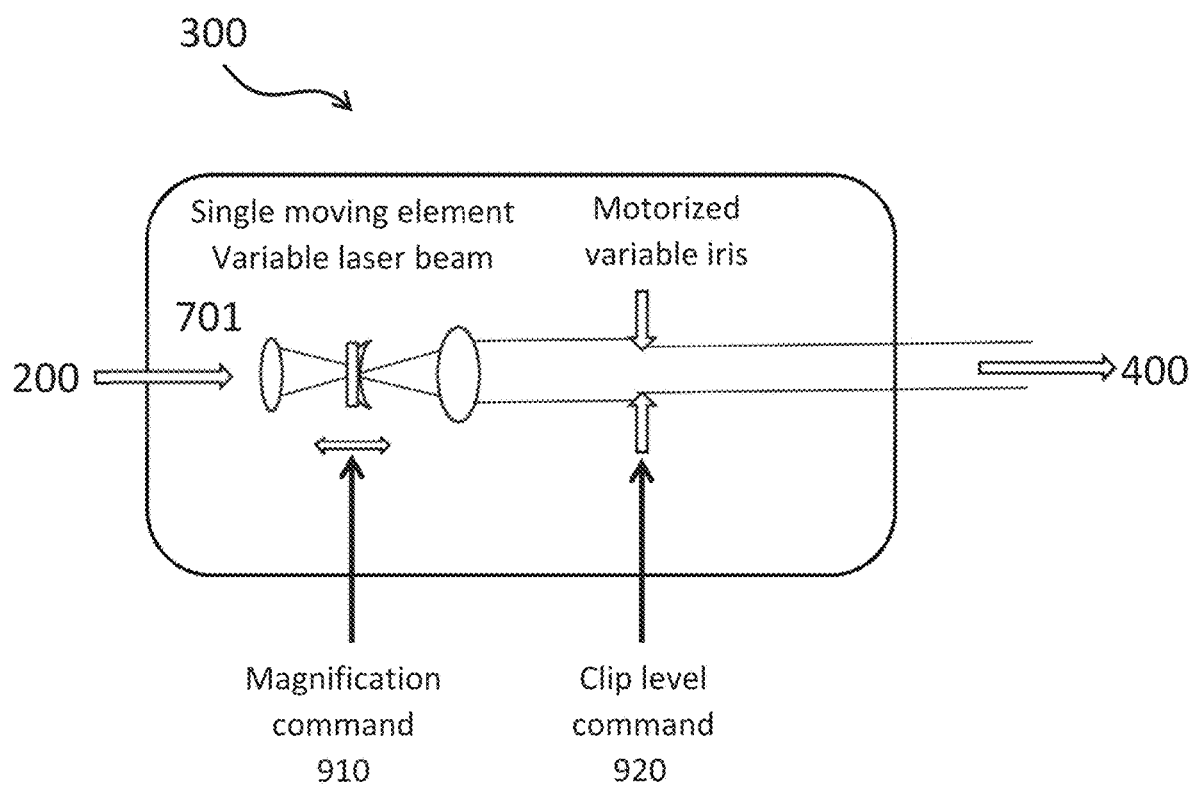
FIGS. 17A-17D illustrate various elements of an embodiment of this disclosure.

FIGS. 17A-17D illustrate block diagrams of various elements of an embodiment of this disclosure that includes the VLBE with a single moving element as well as embodiments incorporating a focus module with the counterweight discussed above. FIG. 17A illustrates a Beam Shaper module 300 that includes the VLBE 701 that may be positioned between several lenses. Such module may be positioned within the system to receive input from the laser, illustrated by 200 in the figure and subsequently may transmit the beam to a laser guide module 400. Additionally, the movement of the VLBE 701 may be controlled by a magnification command 910 that can direct the position of the lens by the linear drive and thereby place the lens at the desired position based on the variety of factors discussed above, including the patient's optical topography.

Figure 17B:
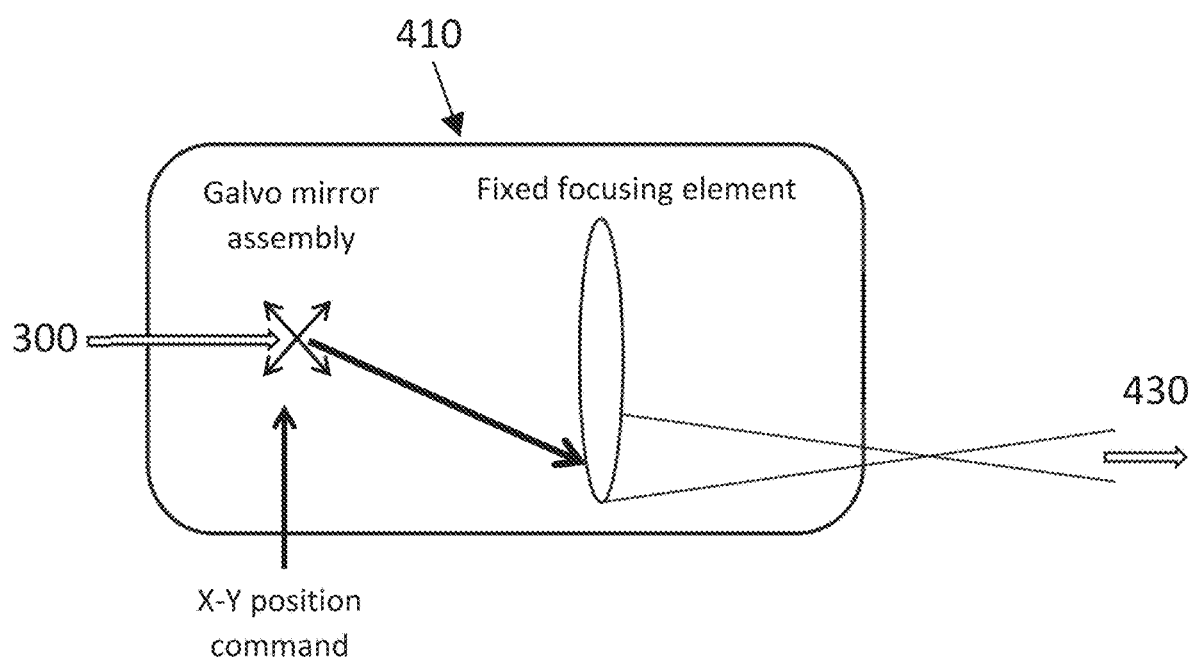
Figure 17C:
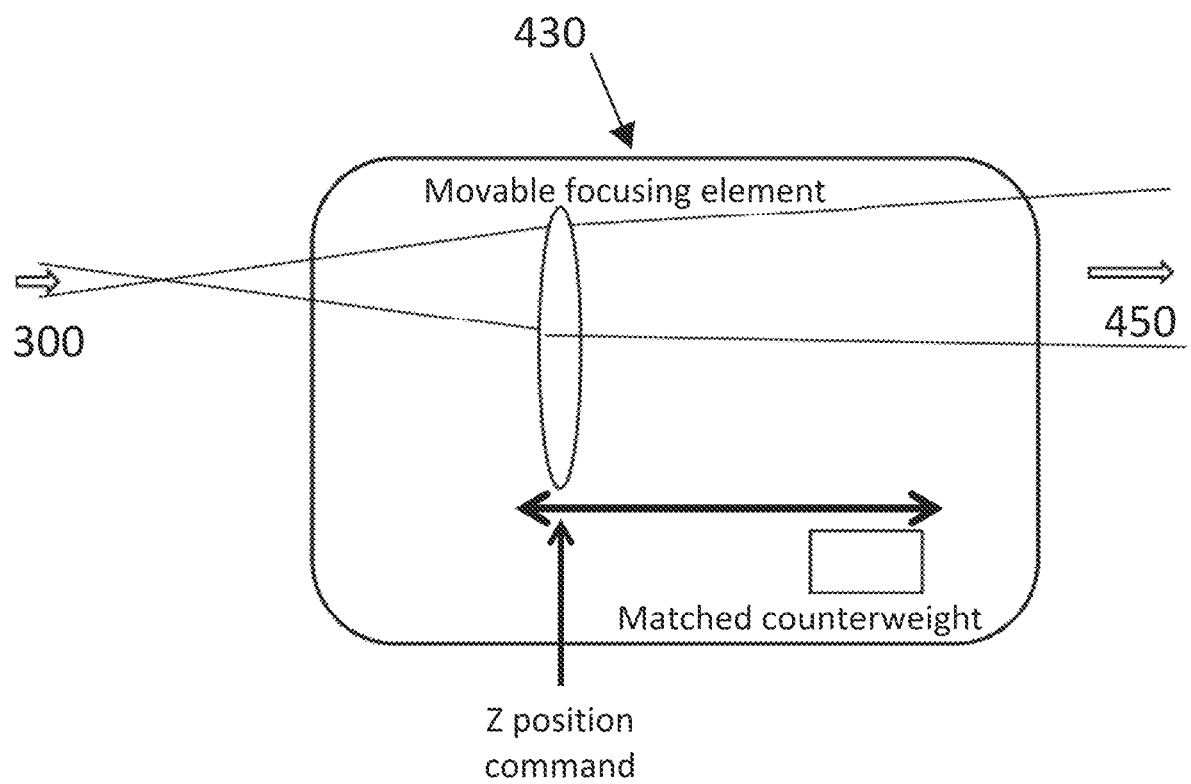
Figure 17D:
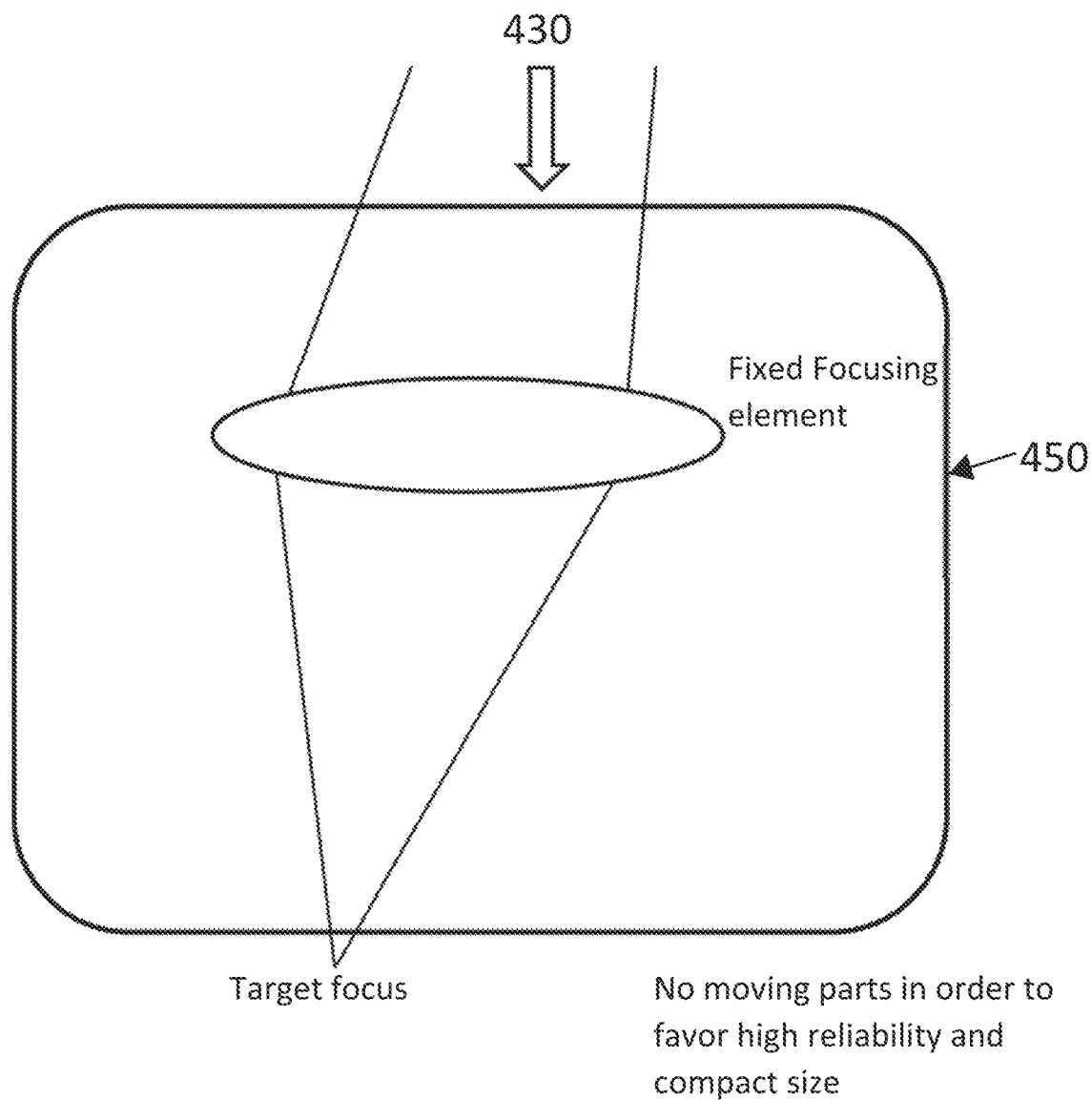

FIGS. 17B-17D illustrate how the shaped beam from the beam shaper module 300 may be directed through the other elements of the system previously described; such as the scan module 410 with galvanometer actuators (FIG. 17B), the focus module 430 with a moving counterweight (FIG. 17C), and from focus module 430 to an objective module 450 to precisely control the final position of the femtosecond laser beam focus, or target focus (FIG. 17D).

The second beam parameter controlled by the beam shaper module 300 is the clip level. This is illustrated in FIG. 17A by the "clip level command" 920. In the field of femtosecond ophthalmic surgery, the femtosecond laser beam is typically produced as a high quality single mode beam with a nearly Gaussian spatial intensity profile. Since a mathematical Gaussian curve has an infinite extent, never completely reaching zero, for any real optical system the Gaussian will be truncated by the finite clear aperture of the components. In the context of Gaussian laser beam optics, the clip level is the percentage of laser intensity at the margin of the limiting aperture, relative to the central peak of the laser intensity profile taken as 100%. As the clip level rises to a high value, for example to 50%, the beam profile shape becomes more "top hat". As the clip level drops to a low level, for example to 5%, the beam profile is very nearly Gaussian. In the case of laser delivery systems, a common choice of clip level is 13%, since this level usually strikes a good balance between the expense of fabricating optics with large diameters (favoring a small aperture/high clip level) versus the goal of maintaining a Gaussian beam profile as the beam passes through the optical train (favoring a large aperture/low clip level). However, due to the wide range of conditions encountered in ophthalmic surgery, it is advantageous to change the clip level from one procedure to another and/or during the course of a procedure. For example, within healthy transparent cornea tissue, a high NA such as 0.35 in conjunction with a low clip level such as 10% may be optimal for creating a high precision cutting action, while in cataractous lens tissue with poor optical quality, a low NA such as 0.20 in conjunction with a high clip level such as 40% may be optimal for creating a powerful and robust cutting action. An apparent drawback of raising the clip level is that more of the laser energy is lost due to clipping. However, if the laser engine has a relatively high unclipped output, such as 15 microjoules, then even with the energy loss due to high clipping, the available energy may still be adequate for the desired procedures, such as 5 microjoules. When excess laser energy is available due to the capabilities of the laser engine, then variable clipping can be a useful way of optimizing optical system performance.

Figure 18A:
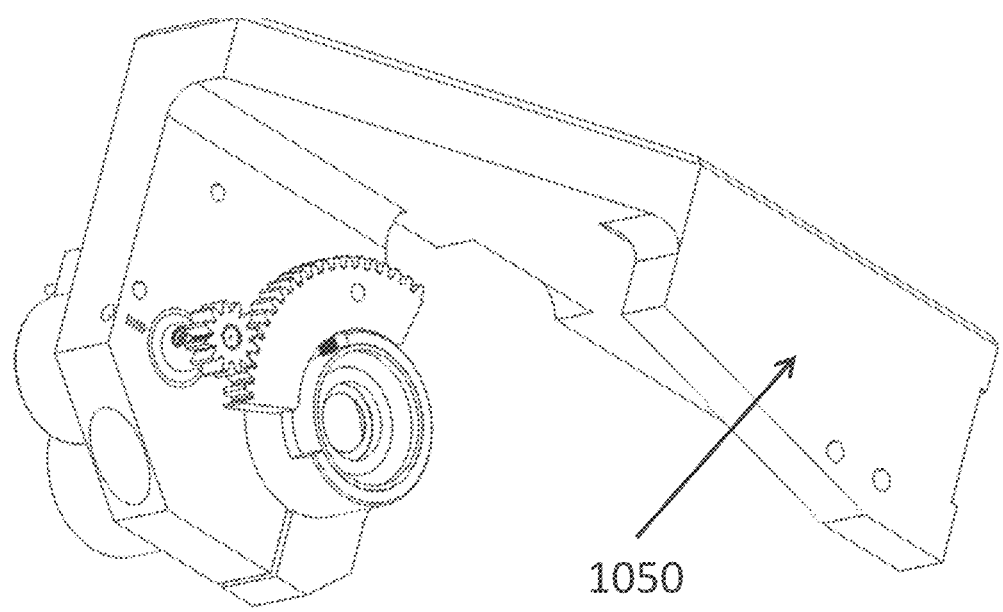
FIGS. 18A and 18B illustrate an embodiment of a motor controlled variable iris, in accordance with an embodiment.
Figure 18B:
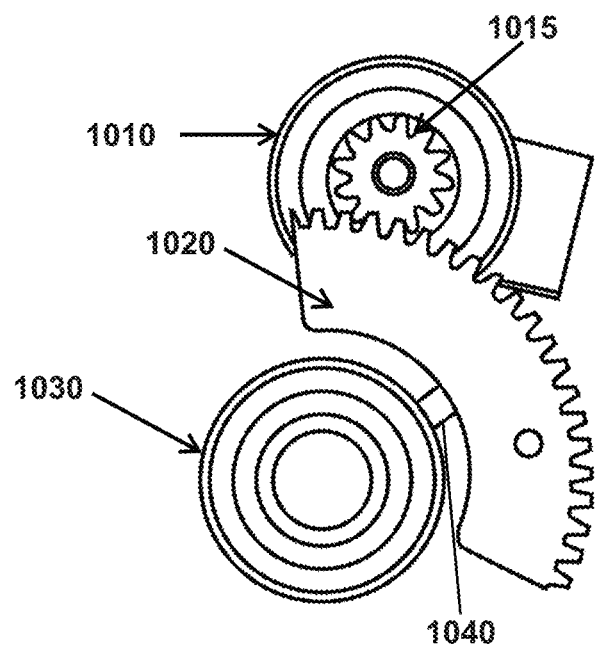

In accordance with various embodiments, the clip level may be controlled by a compact, cost-effective motorized variable iris of the beam shaper. FIGS. 18A and 18B illustrate a motorized iris in accordance with an embodiment of this disclosure, that includes a gear sector actuator. Commercial lenses equipped with an electronic continuously variable diameter iris are typically bulky. Commercially available electronically actuated irises which are compact are apparently found only with a binary open/closed mode of operation rather than a variable position iris.

FIG. 18A illustrates a general view of an embodiment of the variable motor controlled iris attached to a mounting bracket 1050. FIG. 18B illustrates an elemental view of the iris. In some embodiments, the iris may equipped with a sector of plastic gear 1020 attached to the manual iris lever 1040 which controls the opening size. A small motor 1010 may be equipped with a meshing gear 1015 to drive the iris over its available range. One advantage of this design is that the sector gear 1020 is held in place by the iris lever, which prevents out of plane motion, and also by the grip between the motor gear and the round iris housing, which prevents undesired in-plane motion of the sector gear. Because the sector gear 1020 is adequately constrained by the drive mechanism itself, there is little or no need for additional support structures, resulting in a compact design with a minimal number of required parts.

Figure 19:
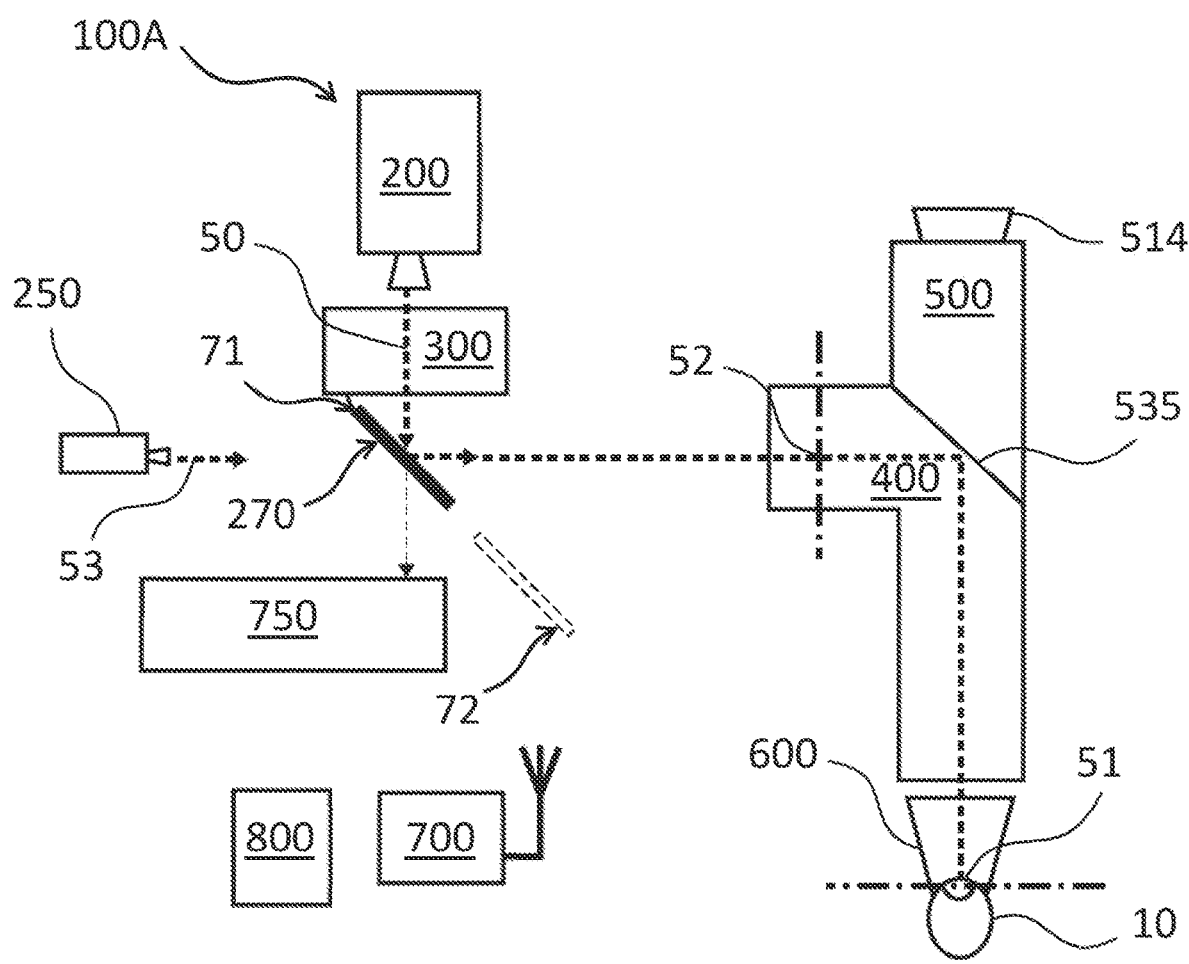
FIG. 19 schematically illustrates an ophthalmic surgery laser system, in accordance with an embodiment.
Figure 20:
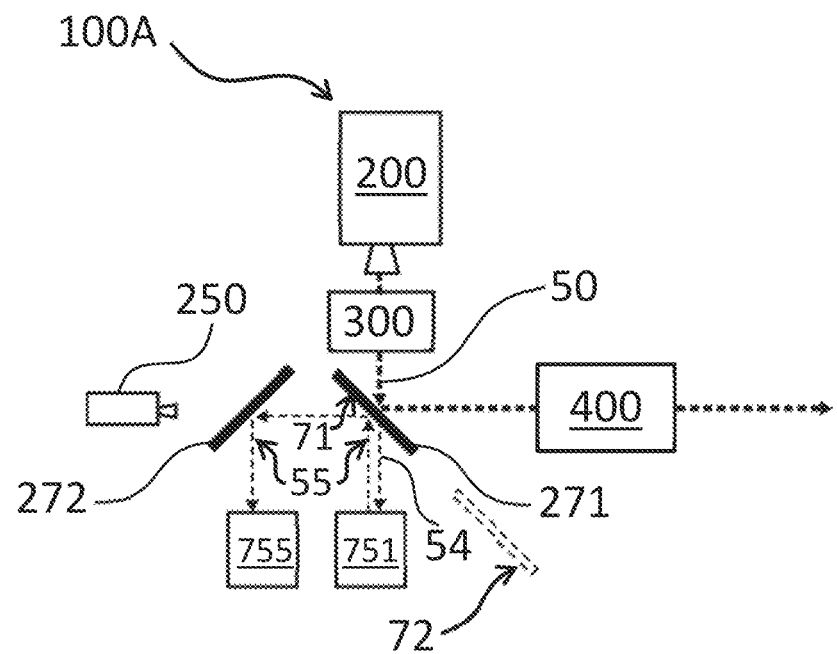
FIG. 20 schematically illustrates aspects of the laser beam diagnostics, in accordance with an embodiment.
Figure 21:
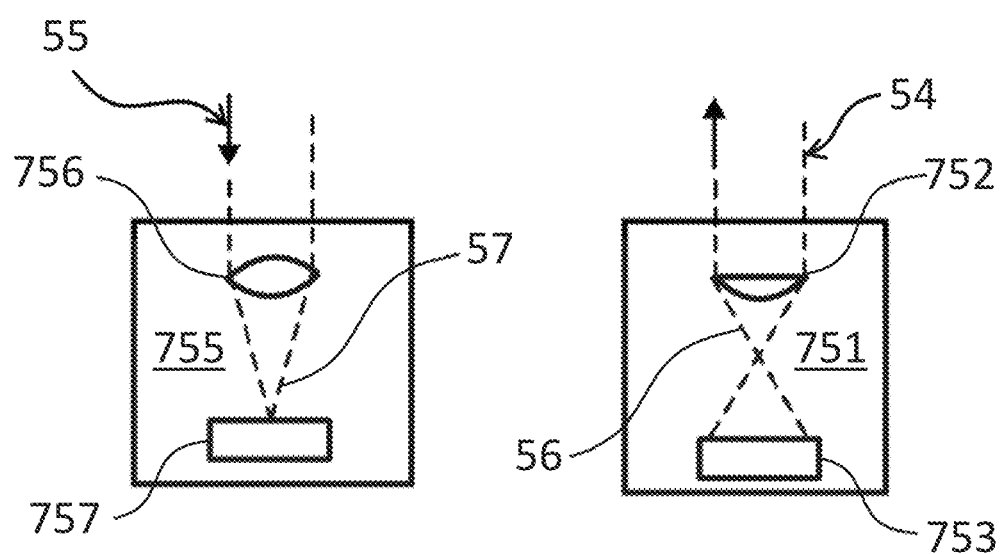
FIG. 21 schematically illustrates another embodiment of the laser beam diagnostics.

FIG. 19 schematically illustrates an ophthalmic surgery laser system according to an embodiment. The ophthalmic surgery laser system 100A ("system") may incorporate similar elements of the ophthalmic surgery laser system shown in FIG. 9, further including integrated laser beam diagnostics and/or an illumination source independent of its surgery laser 200. In particular, the system 100A may include an illumination source 250, a reconfigurable optical device 270, and/or a laser beam diagnostics unit 750. In many embodiments, the system with an LSCM capability should have a far field detector that may additionally take on some functions of a diagnostics unit 750 as illustrated in the figures. The diagnostics unit 750 is important to allow the system the functionality of measuring the far field and near field intensity distributions of the laser beam 50. In accordance with other embodiments the diagnostics unit 750 may be separated into two units such as a far field detector and a near field detector as is illustrated in FIG. 20 and FIG. 21.

The illumination source 250 illustrated in FIG. 19 may utilize features of the system 100A to provide an integrated laser scanning confocal microscope ("LSCM"), where illumination is brought to a focus at the view point. This may advantageously provide improved resolution, for example, where just the area of interest is illuminated. In an embodiment, the LSCM function is used to measure alignment of selected lens surfaces in the laser delivery system.

In an embodiment, the illumination source 250 is a low peak power diagnostic laser source with substantially the same wavelength as the femtosecond laser engine.

According to an embodiment, the reconfigurable optical device 270 may be movable from a first configuration to a second configuration, or otherwise reconfigurable to selectably engage the laser engine 200 or the illumination source 250 as a light source for the system 100A. In alternate embodiments, the reconfigurable optical device 270 may include a beam splitter (e.g., polarizing beam splitter), where optical component may remain fixed, or generally immovable.

According to some embodiments, an ophthalmic laser surgery system, such as system 100A or system 100 (see FIG. 9), may include a laser source (laser engine 200) such as a femtosecond regenerative amplifier at 1053 nm. The light from this source may then directed into a delivery system with the capability to process the beam from the laser over XYZ positions suitable for the system's surgery requirements. Although a specific configuration is illustrated in FIG. 19, many embodiments may include other configurations with less than all of the features described above.

In some embodiments, as illustrated in FIG. 19, the reconfigurable optical device 270 may include a mirror having a first position 71 and a second position 72, the first position 71 engaging the laser engine 200 or otherwise providing it access to the delivery system including elements 400, 600 and/or 500. In some embodiments, element 300 (i.e., beam shaper or laser shaper) may be located between the laser engine 200 and device 270. The first position 71 may disengage or deny the illumination source 250 or otherwise prevent access to the delivery system and/or beam shaper 300, as shown. In particular, when in the first position 71, the laser beam 50 from the laser source (the laser engine 200) may be at least partially reflected into the delivery system and/or beam shaper 300. For example, a full strength laser beam 50 (or a lesser amount, such as 99% strength) may be reflected into the delivery system when the mirror is positioned in its first position 71. Additionally, while in the first position 71, the mirror may block or otherwise prevent a light beam 53 from the illumination source 250 from entering the delivery system.

In contrast, when in the second position 72, the mirror 270 may be out-of-alignment and/or otherwise positioned out of the path of femtosecond laser beam 50, denying access to the delivery system and/or beam shaper 300. Moreover, the mirror may also be out-of-alignment, or otherwise positioned out of the path of light beam 53, thereby allowing access to (or delivery to or engagement with) the delivery system and/or beam shaper 300. In particular, the mirror 270 may be moved to the second position 72, such that illumination source 250 (or another light source) may engage the delivery system. According to an embodiment, this reconfiguration of the reconfigurable optical device 270 (e.g., repositioning of the mirror) may be performed automatically, upon selection, manually, or any combination thereof. In other words a separate control system may be implemented to control the position of the optical device 270 in accordance with the desired use of the system.

Furthermore, only in the second position, the backscattered light resulting from the low power laser or illumination source 250 impinging on the object in the view of the objective may directed onto a far field sensor, as described in greater detail below with respect to FIG. 20, thus enabling the function of LSCM into the ophthalmic laser system in the second position.

In accordance with some embodiments, the illumination source 250 may be a Continuous Wave (CW) laser source. A continuous wave laser source is one that emits a continuous beam with a controlled output of beam intensity. This is in contrast to a pulsed laser that operates by emitting pulses rather than a continuous wave. Some examples of CW lasers may include compact diode lasers and infrared lasers. In some embodiments the laser may be similar to that found in a laser pointing device which will decrease the cost of manufacturing without sacrificing performance. Beneficially, by moving the mirror out of the path light beam 53, an independent light source (here, a lower power CW laser) can access the delivery system, thus sharing the same optics and guidance as the surgery laser of the laser engine 200 and thereby allowing the same system components to be used in an entirely different manner, i.e., diagnostic measurements in addition to surgical cutting. Thus, the system increases its capabilities without significantly increasing the complexity of the system.

According to one embodiment, the illumination source 250 (e.g., CW laser source) may have an identical or substantially similar wavelength as the surgery laser and, when engaged or provided access to the delivery system, act as an LSCM (see above) utilizing the same delivery system elements used by the system's surgery laser 200. Moreover, in this case, for a given XYZ setting of the scan system (e.g., laser shaper 300), a point imaged by the LSCM with the CW laser (light beam 53) may be substantially the same point that a surgical femtosecond laser beam (laser beam 50) would focus to if engaged or the system 100A is otherwise switched to a "surgery operation mode". Advantageously, this may provide a higher level of precision in directing the surgery laser focal spot position during the procedure. For example, it may be comparable to providing a system calibration procedure using the patient's actual eye at the beginning of every procedure. Thus, even if the control system XYZ calibration has drifted since factory calibration in terms of the absolute position of the laser focus vs the control system voltages, the LSCM will still direct the laser accurately onto the tissue. This important advantage is obtained because the potential calibration drift affects the LSCM and the surgical laser in the identical amount and will not compromise the cutting accuracy when the laser is steered according to the LSCM data.

FIG. 20 schematically illustrates aspects of the ophthalmic surgery laser system of FIG. 19 in a first configuration, and shows its laser beam diagnostics in greater detail. For example, the system 100A illustrated in FIG. 20 may be configured in a surgery operation mode, and the laser beam diagnostics of system 100A are illustrated having both near-field and far-field beam metrology functions, which enable remote control of at least some field service procedures and/or parts in the system, and, moreover, provide real-time information on an operational status of the femtosecond laser engine 200 and its beam 50, including diagnostics. For example, as discussed further below, the laser beam diagnostics of the system 100A may include a near field diagnostics module 751 (i.e., a second diagnostics module) and a far field diagnostics module 755 (i.e., a first diagnostics module). Advantageously, this embodiment may provide for measurement of both near field and far field characteristics of the surgery laser beam, for example, by performing diagnostics on the small portion of the beam 50, such as 1%, which is transmitted through the highly reflective mirror which may be included in the reconfigurable device 270.

According to some embodiments, the system 100A may include a reconfigurable optical device having a first mirror 271 and a second mirror 272. In an embodiment, the second mirror 272 is fixed. In addition, the first mirror 271 may be reconfigurable to be placed in the first position 71 and the second position 72. Furthermore, system 100A may have a surgery operating mode that corresponds to the first position 71, and a "laser beam diagnostics mode" that is also available in the first position 71. In a surgery operating mode, the system 100A may be configured such that the movable first mirror 271 positioned in its first position 71, engaging surgery laser beam 50 and providing it access to the delivery system, beginning at laser shaper 400 in this embodiment.

As illustrated, the first mirror 271 may be configured to provide a portion of the surgery laser beam 50 for laser beam diagnostics. In particular, a leakage beam 54 may pass through the first mirror 271 to at least one of the near field diagnostics module 751 and the far field diagnostics module 755. For example, the first mirror 271 may include a partially transmissive mirror coating that allows the leakage beam 54 pass through. As shown here, a minimal amount of the surgery laser beam 50 is transmitted through the mirror coating of the first mirror 271 as the leakage beam 54. According to one embodiment, the leakage beam 54 may represent a 1% transmission of surgery laser beam 50, with the remaining 99% being reflected into the delivery system. Even at 1%, the energy of the leakage beam 54 may be more than sufficient for charge coupled device ("CCD") based beam diagnostics.

In accordance with some embodiments, the first mirror 271 may be further configured to interact with a portion of the leakage beam 54, In particular, the first mirror 271 may include a high reflection surface. In this way, portions of the leakage beam 54 may be efficiently reflected as a sample beam 55 for further diagnostics and analysis, as discussed below. In one embodiment, when the reconfigurable optical device or mirror 271 is in the first position, a small portion of the femtosecond generated laser beam engages with the laser beam diagnostics unit.

FIG. 21 schematically illustrates one embodiment of the laser beam diagnostics of FIG. 20. In particular, the near field diagnostics module 751 may include near field optics 752 and at least one near field sensor 753, as shown. Further, the far field diagnostics module 755 may include far field optics 756 and at least one far field sensor 757, as shown. According to one embodiment, the near field optics 752 may include a plano-convex lens, and the near field sensor 753 may include an image sensor or CCD used to generate higher quality images.

In an embodiment, the far field sensor includes an array sensor such as a CCD. According to one embodiment, the far field optics 756 may include a doublet lens, and the far field sensor 757 may include an image array sensor or CCD. It is understood that the near field sensor 753 and the far field sensor 757 may or may not be the same type or similar devices.

According to one embodiment, the near field optics 752 may be arranged such that at least a portion of the leakage beam 54 is passed to or otherwise directed toward the near field sensor 753, for example, along near field optical path 56. As such, the near field optics 752 may form a near field image from the leakage beam 54 on the near field sensor 753. In particular, the sensed data may be processed such that the surgery laser beam near field characteristics may be measured and/or analyzed, for example, by an operator or with automated functions programmed into the controller 100A.

Additionally, the near field optics 752 may be further configured to reflect back, or otherwise deliver away, a portion of the leakage beam 54 for further analysis. In particular, a sample of the leakage beam 54 may be provided to the far field diagnostics module 755 as the reflected sample beam 55, in accordance with an embodiment. For example, the near field optics 752 may include a plano-convex lens having a partially reflecting coating (e.g., 1%-50% reflecting coating) applied to its plano side. Additionally, the plano-convex lens may be oriented such that at least a portion of the leakage beam 54 is reflected away from the near field optics 752 as the sample beam 55.

The near field optics 752 may be further configured such that the backward reflected sample beam 55 will then hit, for example, the back side of the first mirror 271 when in the first position 71 (see FIG. 20), experience a high reflection surface, be directed toward the second mirror 272, and then be directed by the second mirror 272 to the far field diagnostics module 755. There, the reflected sample beam 55 may pass into the far field optics 756 to form a far field image of the surgical laser beam on the far field sensor 757.

Advantageously, in this way, a surgery laser beam 50, such as a femtosecond laser beam, may be characterized in real time with respect to its near- and far-field beam characteristics. This characterization may be performed using the near field sensor 753 to receive the near field signal, and the far field sensor 757 to receive the far field signal. In general, a laser beam may be characterized much more definitively when both near- and far-field are known, compared to only measuring only a single one of those quantities, or in regard to traditional laser systems, compared to measuring neither quantity with built-in diagnostic functions A surgery laser equipped with on board laser beam near field and far field diagnostics may enable additional reliability by automatically verifying correct operation of the laser engine 200 prior to each clinical procedure, and may enable some remote maintenance procedures to be performed by service personnel, since the near field and far field measurement tools are already in the laser system and do not need to be transported to the laser in the field as would traditionally be required.

Figure 22:
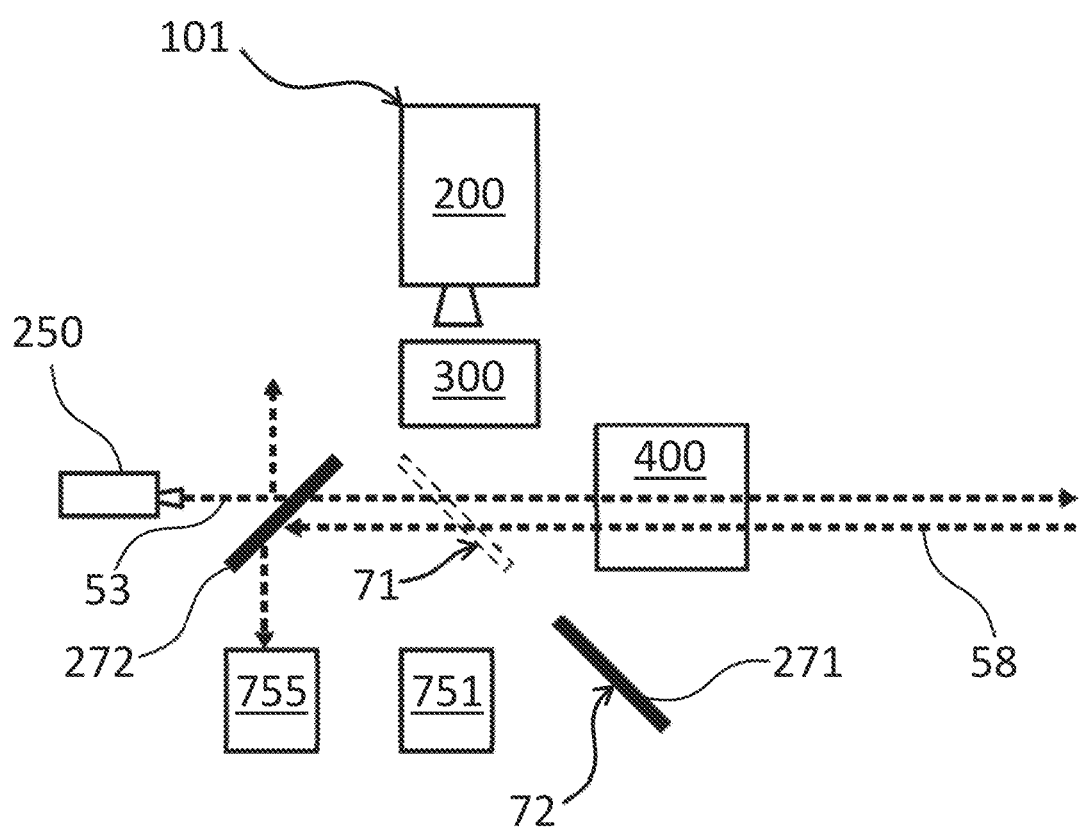
FIG. 22 schematically illustrates aspects of the ophthalmic surgery laser system which enable LSCM functionality, in accordance with an embodiment.

Turning now to FIG. 22, aspects of the ophthalmic surgery laser system of FIG. 20 in a second configuration are illustrated. In some embodiments, the system 100A may be configured as a Laser Scanning Confocal Microscope ("LSCM"), or in an LSCM mode. As discussed above, in LSCM mode, the system 100A may engage the illumination source 250 or otherwise use an independent, lower energy illumination source (such as the CW laser discussed above), rather than the surgery laser for LSCM measurement procedures.

In the illustrated embodiment, when the first mirror 271 is moved aside (here, from its first position 71 to its second position 72), illumination source 250 may be able to pass a weak collimated laser or other lower energy illumination into the delivery system as light beam 53. Light beam 53 may then be directed by the laser guide optics 400 to a selected XYZ position at a target (e.g., patient's eye). Some of this light will be scattered back into the delivery system as return light 58. It is understood that return light 58 may vary depending on the density and other characteristics of the tissue or material at the target location.

With the first mirror 271 in the second position 72, the return light 58 may be directed via the delivery system and reconfigurable optical device back to the laser beam diagnostics which include a far field receiver 755. For example, as shown, return light 58 may be received back from the target region (e.g., patient eye) through the delivery system, onto the second mirror 272, and into the far field diagnostics module 755. As discussed above, and similar to the reflected sample beam 55 of the laser engine 200, the return light 58 may be focused onto a far field sensor (e.g., CCD in some implementations) of the far field diagnostics module 755 by its far field optics.

In this and other LSCM systems, by scanning the XYZ position of a CW laser, for example, and measuring the intensity and distribution of the returned light signal, a 3 dimensional image of the tissue, or other material, can be produced. For the purposes of laser surgery, the locations of the anatomic surfaces can be accurately measured, while for more general clinical diagnostic testing, it may be of more interest to image regions in the middle portions of the cornea or lens.

Beneficially, the cost to add the LSCM function described above to a laser surgery system is relatively low because the costly scanning and focus control optics are already present and may be co-opted. Furthermore, by using CCDs (and the like) in the near field diagnostics module 751 and the far field diagnostics module 755 (see FIG. 21) instead of the traditional LSCM single element detector may allow for decreased sensitivity for alignment drift and can also provide more imaging information than a single element detector. Finally, using a lower power illumination device (such as a CW laser) for diagnostics may provide added safety for the patient, compared to a higher peak power pulsed laser light source, which may cause unwanted nonlinear optical effects on the tissue being imaged.

Some embodiments may be used for the measurement of tissue. The primary measurement concern for a surgical laser is to have a calibrated position for the necessary anatomic surfaces, in order for the laser control system to accurately implement the procedure selected by an operator. The process of defining and locating a mathematically smooth surface to represent an anatomic surface, for example the anterior lens capsule, may involve averaging of values because at the 2-20 micron scale there is extensive cellular structure which can be resolved, i.e., the anatomic surfaces are not smooth at the microns scale. The data bandwidth requirements for biometric surface location may be relaxed compared to detailed 3D microscopic imaging of the tissue. Thus, a CMOS or CCD sensor has some advantages as the far-field sensor for anatomic surface measurements, described below.

For some applications, such as pocket cuts, there may be benefits to measuring internal structure with 3D microscopic detail. For example the corneal nerve fibers could be located in the region of planned surgery, and then small adjustments could be made on the fly in order to minimize collateral damage to nerves or other sensitive structures in the eye due to conducting the laser procedure. Some embodiments may require high bandwidth in order to obtain volumetric imaging data in a reasonable time, such as in the case of a traditional use of a fast single element detector (SED) following a pinhole to comprise the far field detector. Such uses may be preferred over an array detector such as CCD for some applications. The use of an SED may be challenging in accordance with some embodiments because the mechanical pinhole alignment is quite critical in a confocal microscope system. Accordingly, the use of an SED in some embodiments can allow for the pinhole alignment to be automatically optimized in order to maintain optimum performance.

This type of pinhole alignment adjustment is commonly done as a manual procedure with dedicated confocal microscope instruments. For example, piezo actuators to adjust the X,Y pinhole position may be compact, stable, and provide very small step size of adjustment. A calibration signal to adjust the pinhole can be conveniently obtained by placing a slightly turbid scattering medium, such as 1% milk diluted in water or a microsphere suspension, in contact with the output lens interface, and focusing the LSCM beam into the bulk medium. In this case the return signal is due to the laser focus itself, and the microsphere suspension method is commonly used to measure and optimize the point spread function of confocal microscopes. For the LSCM application which uses a single wavelength, simply adjusting the X,Y pinhole position to maximize the light signal on the SED may be more practical for clinical use because it lacks the need of more elaborate imaging tests used in multi-wavelength microscopy. In some embodiments an array sensor may be used as the far field detector. Such embodiments can utilize software to create a virtual pinhole, where the above pinhole calibration procedure can be readily performed without any moving parts to adjust when an array sensor is used. Thus using a CCD for the far field sensor may reduce the complexity and increase the reliability of the system compared to an SED.

LSCM Usage for Z Calibration

In addition to enabling precise measurements of tissue anatomy, in some embodiments, the LSCM method can accurately measure some optical properties of the delivery system itself. For example, some of the curved lens surfaces may be brought to a center of curvature focus for the LSCM beam within the adjustment range of the focus module, in this case the lateral position of the return image will indicate the centration of the LSCM beam with respect to the particular surface in focus. This method is discussed further under "system alignment". Another useful measurement which can be made with LSCM is the actual X,Y,Z position of nearly any point on the surface of the Contact Interface (CI) form of the patient interface. The surface of the CI serves as a mechanical reference which registers against the cornea representing zero cut depth, so it is crucial to accurately measure and control the laser focus with respect to the CI surface.

There are two modes of LSCM signal return from the concave final glass CI surface, these are called specular and diffuse. In the specular mode the Fresnel reflection of the LSCM beam on the final concave glass surface is reflected back into the delivery optics at an angle within the acceptance pupil, thus the reflected beam will be directed back through the delivery system and to the far field detector in order to produce a signal. The specular mode dominates when the radial position of the laser spot in the X,Y scan field is at or near the center of the CI lens; in this case the Fresnel reflection (i.e., specular reflection) of the beam will occur on a surface nearly normal to the LSCM beam propagation axis. As the X,Y position of the laser spot moves away from the center, it will intercept the concave CI surface with an increasing slope relative to the LSCM beam axis. Beyond some particular distance from the center axis for the laser spot position, such as about 1.5 mm depending on the curvature of the concave CI surface, the Fresnel reflected beam may be directed back at a large enough angle so that is totally vignetted before it reaches the far field detector, thus no specular signal will be found outside of the specular cutoff radius. At radial spot positions outside the specular cutoff, it is still possible to obtain a signal from the CI surface by placing it in contact with a diffuse reflecting material, such as applying white paint onto the glass surface. With a diffuse reflection, the return light is spread over a wide angular range, so a small fraction of the scattered light will always be directed inside the acceptance pupil and therefore it will reach the far field detector. Since the diffusely reflected light spreads over a wide range of angles, the signal level is far lower than the case of specular reflection. The low signal level is generally not a problem for detecting diffuse signals, but it does mean that when the specular signal is present then the diffuse signal may be impossible to resolve. In the near vicinity of the specular cutoff radius, the partially vignetted specular signal may become comparable in intensity to the diffuse signal, resulting in a more complex signal than the purely specular and diffuse cases for the radius ranges inside and outside, respectively, the specular cutoff radius.

Figure 23:
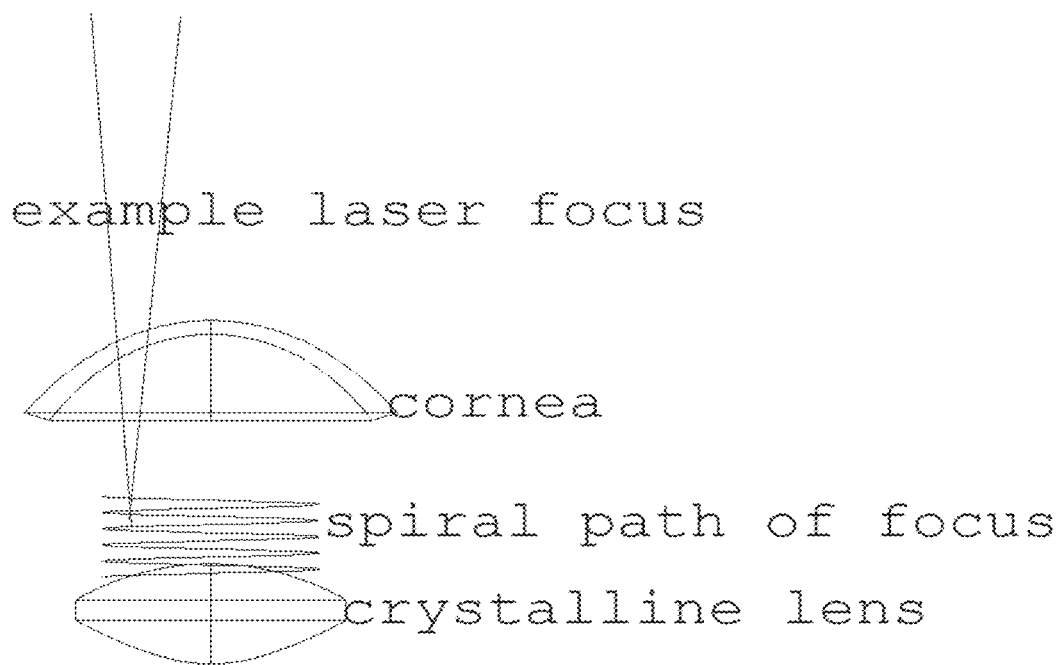
FIG. 23 illustrates an embodiment of this disclosure.

In accordance with some embodiments, a useful method to measure surface topography with LSCM may be to scan the laser focus in a spiral pattern which is circular in X and Y and linear in Z, such that the spiral begins above the surface of interest and ends below the surface. This embodiment advantageously places the fastest scanning requirements on X and Y, which are controlled by the galvanometer mirrors 405, in a particular implementation, while the slower Z axis control can follow a low acceleration linear ramp. An example LSCM spiral where the surface of interest is the anterior lens surface is shown in FIG. 23. When the beam focus passes through the anterior lens surface the return signal level will increase, so by analyzing the LSCM spiral data, the surface Z position can be mapped out over the radius of the spiral scan. While this process may appear analogous to the through-focus linear Z scans utilized in conventional LSCM, it improves upon conventional methods by utilizing a spiral scan to measure Z over a cylindrical region rather than measuring Z along a single line as in a through focus Z scan.

Figure 24:
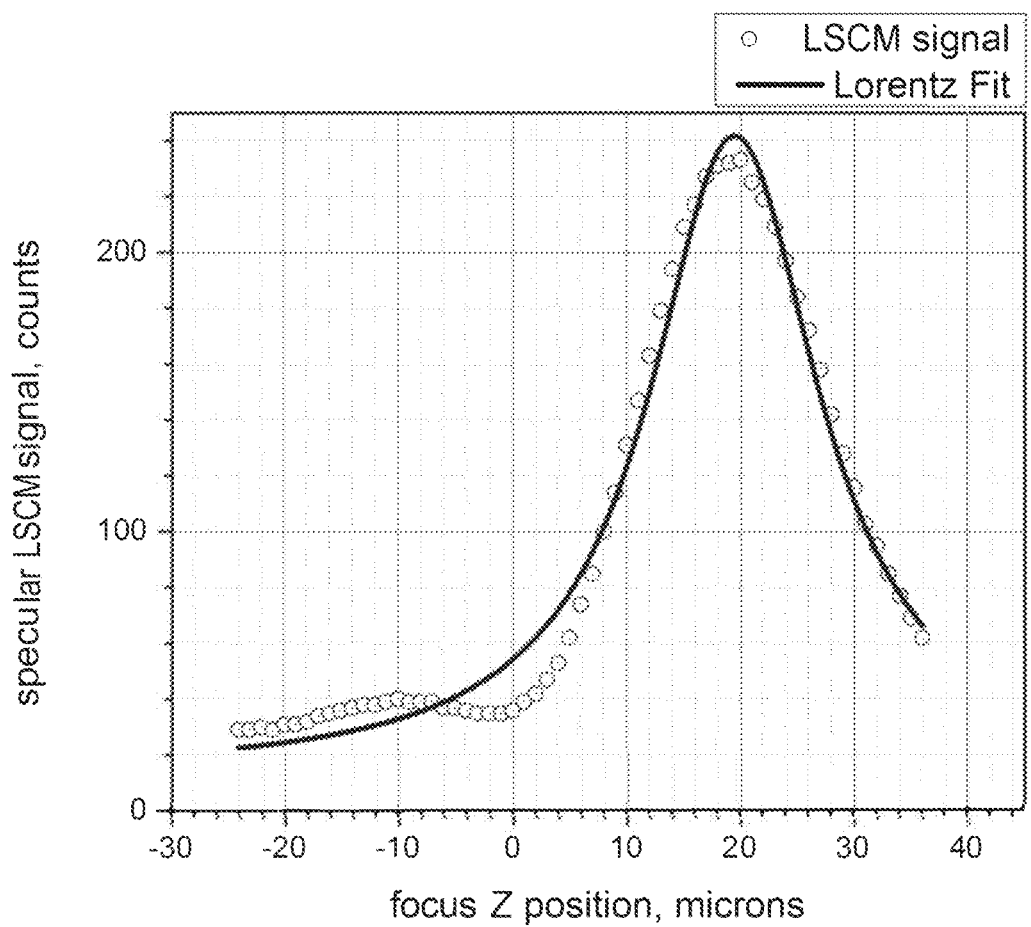
FIG. 24 is a graphical illustration of a data plot in accordance with an embodiment of this disclosure.

FIG. 24 illustrates a data plot in the case of a specular LSCM measurement, taken near the center portion of a Contact Interface lens, in accordance with an embodiment. The signal in this case is a maximum when the focus coincides with the partially reflective surface. The shape of the signal is reasonably well represented by a Lorentzian curve, as predicted for the axial intensity profile of a Gaussian beam. The signal as shown in FIG. 24 does include a small secondary peak at the left side, this is characteristic of minor spherical aberration, however this effect is small enough that the assumption of a Gaussian beam is accurate for locating the primary focus. The specular signal is easily analyzed since the peak of the signal is sharp and it is centered on the surface.

In some embodiments such as the case of performing diffuse LSCM spiral scan measurements of the Contact Interface surface, it is convenient to use a fluid with low viscosity as the scattering medium, to simplify the processes of applying the material onto, and subsequently cleaning the material off from the Contact Interface surface. A highly scattering material such as paint will have the scattering concentrated at the surface due to the negligible penetration of the beam into the dense material, resulting in a similar signal to the specular case, having a sharp peak which is centered on the surface location. However for clinical and laboratory applications it may be useful to use a material comparable to milk, which can be flowed through small tubing to make surface contact and then easily rinsed away with sterile saline. This thinner material in some embodiments may have a lower density of scattering features than a paste and may be termed a moderately scattering medium. In the moderate scattering case the beam may penetrate significantly into the medium, i.e., the transmission depth into the medium is similar or larger than the axial depth of focus of the LSCM beam. In such cases, the measured signal is the sum of contributions starting at the surface where the scattering medium is encountered and on down until the beam has been attenuated below a measurable level by the scattering process. The moderate scattering case requires a more complex analysis, but the advantages of using a convenient fluid can outweigh the computational effort in practical applications.

Figure 25:
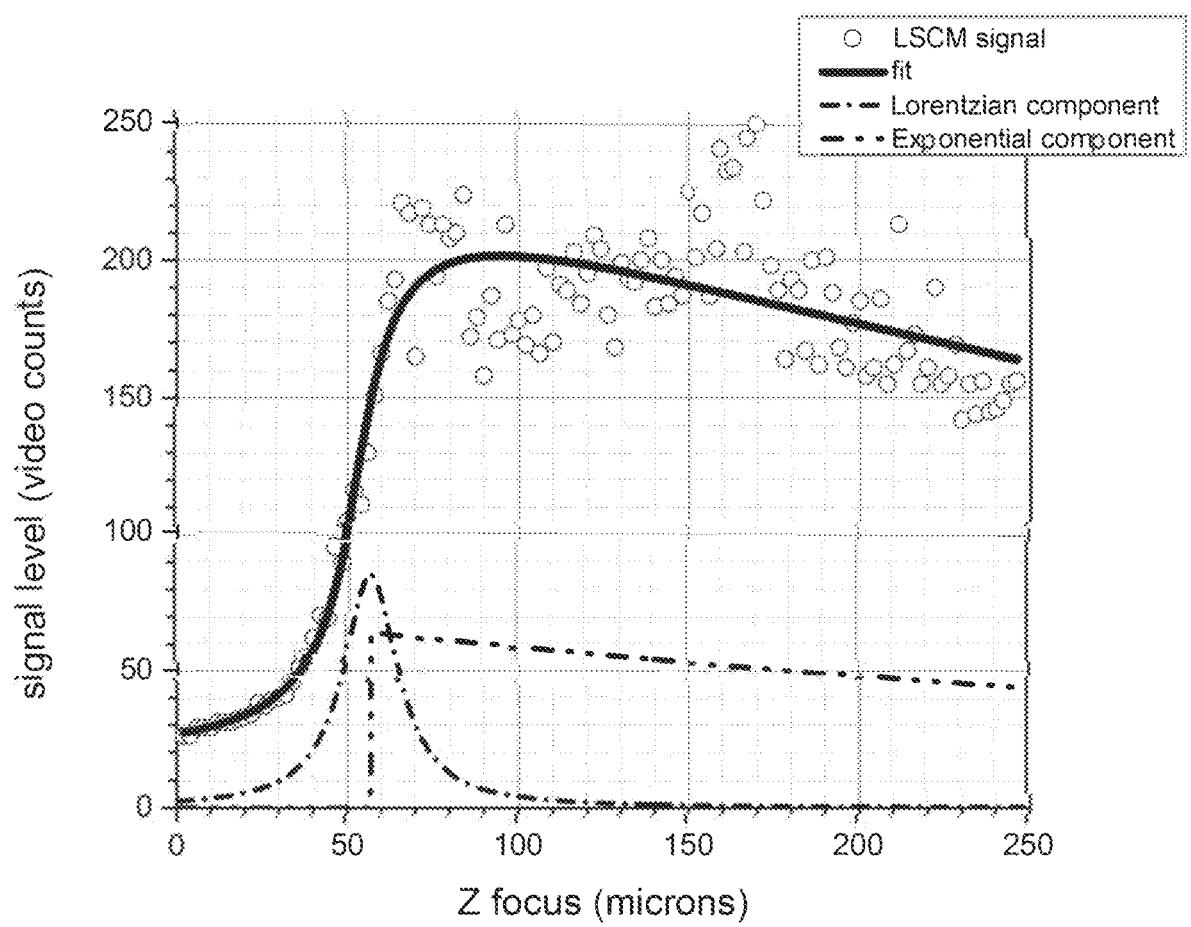
FIG. 25 is a graphical illustration of an embodiment of an LSCM measurement, in accordance with an embodiment.

An example of a diffuse LSCM spiral scan signal plotted as a function of depth at a particular radial and azimuthal position is shown in FIG. 25. Due to the range of penetration into the moderately scattering medium, the peak of the signal will be broad with considerable noise, so the location of the peak is not an accurate way to locate the surface position in this case. A good characteristic to use for surface position measurement may be the rising edge of the signal, which is steep and provides a repeatable and precise measure of the surface location, to within about 1 micron for example. In this case, a more elaborate calculation is required in order to have an accurate measurement of the surface location which is somewhere along the rising edge of the signal, compared to the simplicity of finding the center of a sharp peak in the case of a specular signal or a highly scattering signal.

The model developed to address diffuse scattering here is based on Gaussian beam optics, in which case the axial intensity profile has the mathematical form of a Lorentzian curve. The peak height of the Lorentzian coincides with the maximum intensity at the laser beam focus, and at Z positions away from the focus, the shoulders of the curve define how the axial intensity decreases. The half width at half maximum of the axial intensity for a Gaussian beam is also known as the Rayleigh range of the beam. A second component of the diffuse scattering model, in some embodiments, may be that the beam is attenuated exponentially in passing through the medium, i.e., it follows Beer's law. The model then can simulate the observed signal as the convolution of the Lorentzian and exponential, with the inclusion of vertical scale and offset factors to account for amplification and background level. By de-convolving the data, the start position of the exponential component will correspond to the precise surface location at which the scattering signal begins. The de-convolved Lorentzian width separately provides a measurement of the Rayleigh range of the LSCM beam.

The mathematical de-convolution operation is in general difficult to use with experimental data because it is notoriously sensitive to noise or other minor defects in the data. A preferred method to analyze the data, in accordance with some embodiments may be to employ iterative forward convolution as a replacement for de-convolution. In the iterative forward convolution method, some initial estimates are made for the Lorentzian width, the exponential decay constant, and the starting position of the exponential, as well as the vertical scale and DC offset factors, for a total of 5 adjustable parameters. At each step, the convolution of components is numerically computed and the resulting curve is compared point by point with the data to compute the Chi squared as the sum of the squared deviations between data and model. Based on some optimization algorithm, the parameters are adjusted so that the model reaches a least-squares best fit to the data. For example, the downhill simplex method is a robust and simple to implement optimization algorithm if computation time is not a critical factor. FIG. 25 illustrates the results of this fitting method in a particular example, showing the fit and the component functions resulting from the fitting process, especially the edge of the exponential function corresponding to the surface location. Thus, the surface location may be accurately measured directly in the coordinate system of the laser delivery system. This inherent calibration advantage is not available when using a different beam source to perform spatial measurements, as in OCT and 3D scanning.

Figure 26:
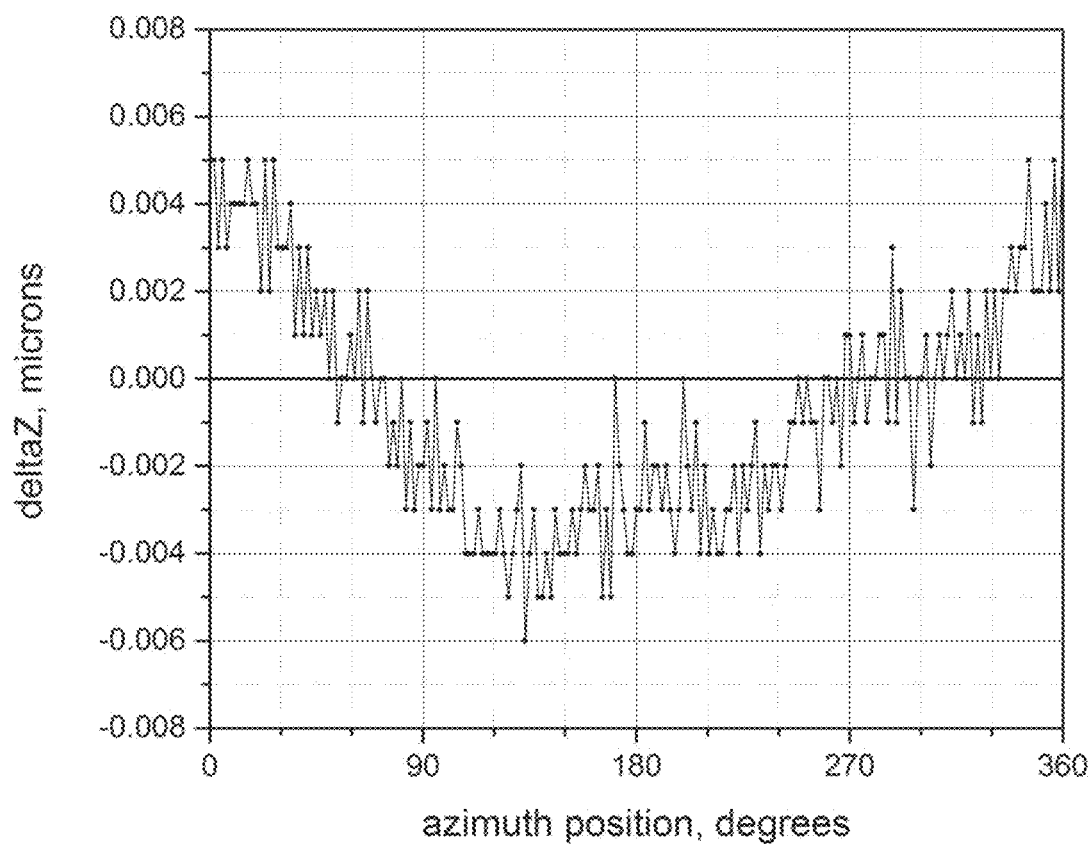
FIG. 26 is an illustration of the results of a spiral LSCM measurement, in accordance with an embodiment.

Turning now to FIG. 26, the results of a spiral IRz scan are shown for diffuse reflection calibration of a Contact Interface. Each point is the Z offset at a particular radial position where the measured surface position is compared to the expected surface position. The scatter in the data is quite low, in the range on 1 micron. There is an overall variation of about 8 microns corresponding to tilt in the cutting depth. This small amount of tilt is below the Rayleigh range of the beam, and yet it is easily quantified by the LSCM method, showing that the LSCM method is suitable to calibrate a laser delivery system Z control to a tighter accuracy than the depth of focus of the beam itself (n.b., depth of focus is typically defined as the Rayleigh range for a Gaussian beam).

System Alignment Using the LSCM Functionality

As the focus module moves over its adjustment range, the radius of curvature of the laser wavefront may go through various ranges at different locations in the optical system. In some embodiments, it may be possible to match the laser wavefront radius of curvature to a value equal to the lens surface radius of curvature, when this equality is in effect then a Center of Curvature (CoC) image is formed on the far field detector by the light reflected back from that surface. The CoC image position on the far field detector is a function of the alignment of the LSCM beam onto that particular lens surface. In some embodiments the LSCM beam may be exactly centered on the surface, where the CoC image on the detector may then coincide with the location of the confocal imaging signal. When there is a decenter of the LSCM beam axis with respect to the CoC surface, then the return image spot will move across the far field. In some embodiments where the far field detector is a CCD or other array type detector, it may be capable to measure the off-axis position of the CoC image, providing a very precise auto-collimator-type measurement of the CoC surface alignment with respect to the LSCM beam. This may be useful in production while optimizing alignment of the optical system, or also as a self-diagnostic function for systems deployed in the field to monitor system alignment shifts over time. Such as diagnostic function could potentially produce an early warning service request in case the system optical alignment starts to drift, enabling preventive maintenance to be scheduled before the alignment drift can degrade system performance. In the case of using an SED, there is no capability of measuring any off axis light.

In other embodiments, system alignment may be achieved by installing a wire crosshair (or cross hairs) with precise centration on the input or output aperture of selected optical modules. In accordance with an embodiment, at least some of the optical modules are equipped with very fine wire crosshairs to facilitate system alignment procedures in the factory and/or system alignment verification in the field. Cross hair targets are commonly used as temporary alignment fixtures, but in some embodiments the cross hairs may be permanently installed on selected modules. By using extremely fine wire, such as 10 micron diameter tungsten, such a small proportion of the laser light is scattered that the effect on the final focus is negligible, and it is advantageous for the crosshair wires to remain in place so that alignment can be easily checked and adjusted even when the laser has left the factory and is installed with an end user simply by mounting a spot size measuring camera at the laser output. A spot size camera is a test instrument frequently used in the factory and in field service to re-image the final laser focus onto a CCD with sufficient magnification to resolve the features of the ~2 um laser focus. When the spot camera is imaging the smallest region of the laser output focus, there is no measurable effect from the presence of the wires because the camera is imaging a location at infinity. However, by moving the spot camera below the laser focus, the conjugate image plane moves in from infinity and in some cases the spot camera focus can be adjusted to form an image of the cross hairs with relatively high magnification, using the laser beam itself to provide the illumination. In such embodiments, the centration of the laser beam with respect to the cross hairs is easily determined from the spot camera image of the cross hairs illuminated by the beam. Because of the high magnification of the spot camera, it is useful to aperture down the size of the laser beam for this measurement so that the entire beam is within the spot camera field of view. In some cases, the spot camera magnification may be high enough that the minimum available beam aperture size will not fit into the field of view. In case the laser beam cannot be fit into the field of view, it is advantageous to use the Fresnel rings created by the minimum beam aperture setting of the variable iris in the beam shaper 300 in order to locate the center position of the laser beam and making suitable alignment adjustments to center the Fresnel ring pattern on the cross hairs.

Although the description above contains many specificities, these should not be construed as limiting the scope of the disclosure but as merely providing illustrations of some of the presently preferred embodiments of the disclosure. Various other embodiments are possible within its scope. Accordingly, the scope of the disclosure should be determined not by the embodiments illustrated, but by the appended claims and their equivalents.

Reference throughout the specification to "one embodiment" or "an embodiment" or the like means that a particular feature, structure, or characteristic described in connection with an embodiment is included in at least one embodiment of the subject matter disclosed. Thus, the appearance of the phrases "in one embodiment" or "in an embodiment" or the like in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

While the principles of the disclosure have been made clear in the illustrative embodiments set forth above, it will be apparent to those skilled in the art that various modifications may be made to the structure, arrangement, proportion, elements, materials, and components used in the practice of the disclosure.

It will thus be seen that the features of this disclosure have been fully and effectively accomplished. It will be realized, however, that the foregoing preferred specific embodiments have been shown and described for the purpose of illustrating the functional and structural principles of this disclosure and are subject to change without departure from such principles. Therefore, this disclosure includes all modifications encompassed within the spirit and scope of the following claims.

What is claimed is:

1. An ophthalmic laser system comprising:
    a laser engine capable of generating a femtosecond laser beam;
    a laser delivery system comprising:
    a laser beam shaper module that shapes the generated femtosecond laser beam to generate a shaped laser beam; and
    a laser guide having a scanning module, a focus module, and an objective module,
    wherein the scanning module has a first lens at a receiving end and a second lens at a transmitting end, wherein the second lens is a plano-convex lens and the receiving end receives the shaped laser beam and brings the shaped laser beam into focus thereby creating a focused beam that is transmitted from the transmitting end into the focus module,
    wherein the focus module receives the focused beam from the scanning module and revert the focused beam into a parallel light stream and further directs the parallel light stream into the objective module, the focus module having a first lens and a second lens, wherein the first lens is a meniscus lens and the second lens is a plano-convex lens,
    wherein the objective module directs the parallel light stream from an input end thereof to an output end and into a focal point within a three dimensional target space to enable eye surgery of the human anterior segment, and the objective module comprises a plurality of lenses having no less than four lenses, and no more than five lenses, of which three lenses are plano convex lenses.

2. The ophthalmic laser system according to claim 1, wherein the first lens of the scanning module is a positive optical power lens.

3. The ophthalmic laser system according to claim 1, wherein the plurality of lenses of the objective module includes a plano convex lens, and the plano convex and plano concave lenses in the objective are oriented with each plane surface facing the output end of the objective.

4. The ophthalmic laser system according to claim 1, wherein the laser beam guide comprises a three-mirror galvo group configured to reduce an angle of incidence to 35 degrees on a second mirror and on a third minor of the three-mirror galvo group, and wherein a first distance between a first minor and the second mirror in the three-mirror galvo group is greater than a second distance between the second mirror and the third mirror.

5. The ophthalmic laser system according to claim 1, further comprising a counter balance system configured to maintain stability of the laser delivery system such that the focal point is controlled within the target space during movement of the focus module, wherein the counter balance system comprises a pair of weights configured to move in an opposite direction of the focus module, wherein said pair of weights is configured to position a center of mass of the counter balance system on a same axis as a center of mass of the focus module.

6. The ophthalmic laser system according to claim 1, wherein the laser delivery system further comprises a beam splitter optically positioned between the focus module and the objective.

7. The ophthalmic laser system according to claim 1, wherein the plurality of lenses of the objective module includes a doublet.

8. The ophthalmic laser system according to claim 1, wherein the laser delivery system has a numerical aperture of 0.2.

9. The ophthalmic laser system according to claim 1, wherein the laser delivery system has a numerical aperture of 0.30.

10. The ophthalmic laser system according to claim 1, wherein the laser delivery system has a numerical aperture of 0.35.

11. The ophthalmic laser system according to claim 10, wherein the patient interface further comprises a patient interface lens.

12. The ophthalmic laser system according to claim 1, wherein the laser beam shaper module includes a variable iris for adjusting a clip level of the shaped laser beam.

13. The ophthalmic laser system according to claim 12, wherein the clip level corresponds to a numerical aperture of the laser delivery system.

14. The ophthalmic laser system according to claim 1, further comprising:
    a patient interface between the output end of the objective module and a patient's eye.

15. An ophthalmic laser surgery system comprising:
    a laser engine capable of generating a femtosecond laser beam for surgical procedure;
    an integrated 3D laser scanning system;
    a laser scanning confocal microscope (LSCM) subsystem, comprising:
    (a) a laser source capable of delivering a low peak power laser beam for LSCM measurements, wherein the femtosecond laser beam has an engine wavelength and the low peak power laser beam has a scan wavelength, and the scan wavelength is substantially the same as the engine wavelength;
(b) a beamsplitter in line with the lower peak power laser beam;
(c) a first, far field diagnostics module configured to receive back-reflected light from a patient's eye or other target directed by said beamsplitter;
(d) a second, near field laser beam diagnostics module;
a laser beam guide configured to focus a received laser beam for output;
a fixed mirror and, said second, near field diagnostic module being in communication with said fixed minor; and
a reconfigurable optical device being configured for positioning in a first position and in a second position in order to selectively engage either the generated femtosecond laser beam of the femtosecond laser engine or the low peak power laser beam of the LSCM subsystem,
wherein the reconfigurable optical device is configured such that, in the first position, the reconfigurable optical device optically engages with the generated femtosecond laser beam such that said reconfigurable optical device is in line with a path of the generated femtosecond laser beam generated by the femtosecond laser engine which is configured to direct the generated femtosecond laser beam into the laser beam guide, and wherein the reconfigurable optical device is configured to deny entry of the low peak power laser beam of the laser source into the laser beam guide; wherein, in the second position, the reconfigurable optical device is configured such that the reconfigurable optical device is out of alignment with the generated femtosecond laser beam and thus the generated femtosecond laser beam is denied entry into the laser beam guide and wherein, in the second position, the low peak power laser beam is directed into the laser beam guide so that at least some of the back-reflected light from the patient's eye or other target which returns back through the laser beam guide is directed onto said first, far field diagnostics module to at least measure an intensity of the back-reflected light from the low peak power laser beam;
wherein the second, near field laser beam diagnostics module is configured to be in optical communication with the laser engine such that when the reconfigurable optical device is in the first position, at least a small portion of the generated femtosecond laser beam engages with said second, near field laser beam diagnostics module and provides real time information on operational status of the generated femtosecond laser engine during the surgical procedure; and
wherein said second, near field diagnostic module is positioned to receive a first beam sample which leaks through the reconfigurable optical device in its first position and said fixed minor also being configured to partially reflect a second beam sample onto the reconfigurable optical device in its first position such that the reconfigurable optical device reflects the second beam sample to the first, far field diagnostics module, such that data from said reflected second beam sample is utilized during the surgical procedure.

* * * * *